US012751457B2

(12) United States Patent
Dimopoulos et al.

(10) Patent No.: US 12,751,457 B2
(45) Date of Patent: Oct. 6, 2026

(54) **METHODS FOR THE PREPARATION OF NON-LIVE *CHROMOBACTERIUM* BIOPESTICIDE**

(71) Applicant: The Johns Hopkins University, Baltimore, MD (US)

(72) Inventors: George Dimopoulos, Baltimore, MD (US); Eric Caragata, Baltimore, MD (US); Raul Saraiva, Leca da Palmeira (PT)

(73) Assignee: The Johns Hopkins University, Baltimore, MD (US)

( * ) Notice: Subject to any disclaimer, the term of this patent is extended or adjusted under 35 U.S.C. 154(b) by 297 days.

(21) Appl. No.: 18/249,293

(22) PCT Filed: Oct. 18, 2021

(86) PCT No.: PCT/US2021/055361
§ 371 (c)(1),
(2) Date: Apr. 17, 2023

(87) PCT Pub. No.: WO2022/082088
PCT Pub. Date: Apr. 21, 2022

(65) Prior Publication Data

US 2023/0389554 A1 Dec. 7, 2023

Related U.S. Application Data

(60) Provisional application No. 63/092,857, filed on Oct. 16, 2020.

(51) Int. Cl.
*A01N 63/20* (2020.01)
*A01P 7/04* (2006.01)
*C12N 1/20* (2006.01)

(52) U.S. Cl.
CPC ................ *A01N 63/20* (2020.01); *A01P 7/04* (2021.08); *C12N 1/20* (2013.01)

(58) Field of Classification Search
CPC ...................................................... A01N 63/20
See application file for complete search history.

(56) References Cited

U.S. PATENT DOCUMENTS

2014/0227228 A1* 8/2014 Asolkar ................... C12N 1/20 424/93.4

FOREIGN PATENT DOCUMENTS

WO 2016033396 A1 3/2016

OTHER PUBLICATIONS

World Malaria Report., WHO., (2018).
Malaria Fact Sheets., WHO., (2019).
Dengue and Severe Dengue Fact Sheets., WHO., (2019).
Chikungunya Fact Sheets., WHO., (2017).
Yellow Fever Fact Sheets., WHO., (2019).
Zika Virus Fact Sheets., WHO., (2018).
Bhatt et al. The global distribution and burden of dengue., Nature., (2013), pp. 504-507, vol. 496.
Gould et al. Impact of climate change and other factors on emerging arbovirus diseases., Trans R Soc Trop Med Hyg., (2009), pp. 109-121, vol. 103.
Gubler, D. Dengue, urbanization, and globalization: the unholy trinity of the 21st century., Trop Med Health., (2011), pp. 3-11, vol. 39.
Weaver et al. Present and future arboviral threats., Antiviral Res., (2010), pp. 328-345, vol. 85.
Dutra et al. The re-emerging arboviral threat: hidden enemies: the emergence of obscure arboviral diseases, and the potential use of Wolbachia in their control., Bioessays., (2017).
Conrad et al. Antimalarial drug resistance in Africa: the calm before the storm? Lancet Infect Dis., (2019), pp. 338-351, vol. 19.
Global insecticide use for vector-borne disease control., WHO., (2011), ed. 5.
Killeen et al. Preventing childhood malaria in Africa by protecting adults from mosquitoes with insecticide-treated nets., PLoS Med., (2007), vol. 4.
Du et al. Molecular evidence for dual pyrethroid-receptor sites on a mosquito sodium channel., PNAS., (2013), pp. 11785-11790, vol. 110.
Miller et al. Experimental hut trials of bednets impregnated with synthetic pyrethroid or organophosphate insecticide for mosquito-control in the gambia., Med and Vet Entomology., (1991), pp. 465-476, vol. 5.
Rose, R. Pesticides and public health: integrated methods of mosquito management., Emerging Infec Diseases., (2001), pp. 17-23, vol. 7.
Nishiura et al. Methoprene interferes with mosquito midgut remodeling during metamorphosis., J Med Entomology., (2003), pp. 498-507, vol. 40.
Chandler et al. The development, regulation and use of biopesticides for integrated pest management., Philos Trans R Soc Lond B Biol Sci., (2011), pp. 1987-1998.

(Continued)

*Primary Examiner* — Albert M Navarro
(74) *Attorney, Agent, or Firm* — Johns Hopkins Technology Ventures

(57) ABSTRACT

The present invention relates to the field of pesticides. More specifically, the present invention provides compositions and methods for the preparation of non-live *Chromobacterium* pesticides. In a specific embodiment, a method for producing a non-live *Chromobacterium* biopesticide comprises the steps of (a) growing the *Chromobacterium* in a bioreactor with culture medium; (b) oxygenating the *Chromobacterium* during step (a); (c) adding an antibiotic to the *Chromobacterium* culture; (d) incubating the *Chromobacterium* culture under hypoxic conditions; (e) pouring the *Chromobacterium* culture on to a substrate; (f) air drying the *Chromobacterium*; and (g) crushing the dried *Chromobacterium* into a powder.

13 Claims, 30 Drawing Sheets

Specification includes a Sequence Listing.

(56) References Cited

OTHER PUBLICATIONS

Berry, C. The bacterium, lysinibacillus sphaericus, as an insect pathogen., J Invertebrate Pthology., (2012), pp. 1-10. vol. 109.
Lacey, L. Bacillus thuringiensis serovariety israelensis and bacillus sphaericus for mosquito control., J Am Mosq Control Assoc., (2007), pp. 133-163, vol. 23.
Scholte et al. An entomopathogenic fungus for control of adult African malaria mosquitos., Science., (2005), pp. 1641-1642, vol. 308.
Macoris et al. Resistance of Aedes aegypti from the state of Sao Paulo, Brazil, to organophosphates insecticides., Memorias Do Instituto Oswaldo Cruz., (2003), pp. 703-708, vol. 98.
Protopooff et al. High level of resistance in the mosquito Anopheles gambiae to pyrethroid insecticides and reduced susceptibility to bendiocarb in north-western Tanzanaia., Malaria J., (2013), vol. 12.
Ranson et al. Insecticide resistance in African Anopheles mosquitos: a worsening situation that needs urgent action to maintain malaria control., Trends Parasitology., (2016), pp. 187-196, vol. 32.
Beier et al. Integrated vector management for malaria control., Malar J., (2008).
Ramirez et al. Chromobacterium Csp_P reudces malaria and dengue infection in vector mosquitos and has entomopathogenic and in vitro anti-pathogen activities., PLoS Pathog., (2014), vol. 10.
Saraiva et al. Chromobacterium spp. mediate their anti-plasmodium activity through secretion of the histone deacetylase inhibitor romidepsin., Sci Reports., (2018), vol. 8.
Saraiva et al. Aminopeptidase secreted by *Chromobacterium* sp. Panama inhibits dengue virus infection by degrading the E protein., PLoS Negl Trop Dis., (2018), vol. 12.
Shot et al. Hydrogen cyanide produced by the soil bacterium *Chromobacterium* sp. Panama contributes to mortality in Anopheles gambiae mosquito larvae., Sci Rep., (2018), vol. 8.
Shot et al. The mosquito adulticidal *Chromobacterium* sp. Panama causes transgenerational impacts on fitness parameters and elicits xenobiotic gene responses., Parasit Vectors., (2018), vol. 11.
Smith et al. Pyrethroid resistance in Aedes aegypti and Aedes albopictus: important mosquito vectors of human diseases., Pest Biochem and Physiology., (2016), p. 1-12, vol. 133.
Vontas et al. Insecticide resistance in the major dengue vectors Aedes albopictus and Aedes aegypti., Pest Biochem and Physiology., (2012), pp. 126-131, vol. 104.
Ray et al. Effects of reduced risk insecticides on three orchid pests and two predacious natural enemies., Florida Entomologist., (2014), pp. 972-978, vol. 97.
Shapiro-Ilan et al. Control of Pecan Weevil with microbial biopesticides., Environ Entomol., (2017), pp. 1299-1304, vol. 46.
Beier et al. Attractive toxic sugar bait (ATSB) methods decimate populations of Anopheles malaria vectors in arid environments regardless of the local availability of favoured sugar-source blossoms., Malar J., (2012), vol. 11.
Muller et al. Control of Culex quinquefasciatus in a storm drain system in Florida using attractive toxic sugar baits., Med Vet Entomol., (2010), pp. 346-351, vol. 24.
Stewart et al. Indoor application of attractive toxic sugar bait (ATSB) in combination with mosquito nets for control of pyrethroid-resistant mosquitos., PLoS One., (2013), vol. 8.
Blackburn et al. *Chromobacterium sphagni* sp. nov., an insecticidial bacterium isolated from Sphagnum bogs., Int J Syst Evol Micrbiol., (2017), pp. 3417-3422, vol. 67.
Blackburn et al. *Chromobacterium phragmitis* sp. nov., isolated from estuarine marshes., Int J Syst Evol Microbiol., (2019), pp. 2681-2686, vol. 69.
Lima-Bittencourt et al. Analysis of *Chromobacterium* sp. natural isolates from different Brazilian ecosystems., BMC Microbiol., (2007), vol. 7.
Lima-Bittencourt et al. Characterization of a Chromobacterium haemolyticum population from a natural tropical lake., Lett Appl Microbiol., (2011), pp. 642-650, vol. 52.
Santini et al. Genetic variability in isolates of Chromobacterium violacceum from pulmonary secretion, water, and soil., Genet Mol Res., (2016), vol. 15.
Soby et al. Chromobacterium vaccinii sp. nov., isolated from native and cultivated cranberry (Vaccinium macrocarpon Ait.) bogs and irrigation ponds., Int J Syst Evol Micrbiol., (2013), pp. 1840-1846, vol. 63.
Barrera et al. A novel autocidal ovitrap for the surveillance and control of Aedes aegypti., J Am Mosq Control Assoc., (2013), pp. 293-296, vol. 29.
Poole-Smith et al. Comparison of vector competence of Aedes mediovittatus and Aedes aegypti for dengue virus: Implications for dengue control in the Caribbean., PLoS Negl Trop Dis., (2015), vol. 9.
Bahia et al. Exploring Anopheles gut bacteria for Plasmodium blocking activity., Env Microbiol., (2014), pp. 2980-2994, vol. 16.
OPPTS 830.6317 storage stability., EPA., (2002).
Strelkova et al. Role of extracellular polymer matrix in resistance of bacterial films to extreme environmental factors., Microbiology., (2015), pp. 131-138, vol. 82.

* cited by examiner

| | from 1 Liter of *Csp_P* liquid culture | | | | | | | | 500 mg *Csp_P* powder | | | | | |
|---|---|---|---|---|---|---|---|---|---|---|---|---|---|---|
| *Csp_P culture and air dried powder 1* | Dry Weight *(g)/L* | OD600 of 3d-culture | Cells of 3d culture */OD600* | Total Cells of 3d culture */L* | Total-Protein *(g)/L* | % of Protein | Total-Lipids *(mg)/L* | % of Lipids | From liquid culture *(mL)*[a] | From 3d culture Total Cells[b] | Total Protein *(mg)*[c] | % of Total Protein[e] | Total Lipids *(µg)*[d] | % of Total Lipids |
| *Average* | 16.829[f] | 6.99 | $3.9 \times 10^{8}$ | $1.95 \times 10^{12}$ | 2.59 | 15.40% | 0.021 | 0.0001% | 29.71 | $5.78 \times 10^{10}$ | 76.90 | 15.40% | 0.61 | 0.0001% |
| *S.E.* | 0.59 | 1.36 | $0.43 \times 10^{8}$ | $0.41 \times 10^{12}$ | 0.08 | 0.50% | 0.003 | $1.13 \times 10^{-7}$ | 1.21 | $0.19 \times 10^{10}$ | 2.27 | 0.50% | 0.057 | $1.13 \times 10^{-7}$ |

a: 500 mg of *Csp_P* air-dried powder 1 from the original volume of the *Csp_P* liquid culture (based on 5 L large scale liquid cultures)

b: The total live cells enumerated from CFU assays with 3d-old culture (1 L, 225 rpm 30°C for 3 days), right before the liquid culture was placed on the bench for the biofilm production c: The total protein measured through Micro BCA Protein Assay Kit (Thermo Fisher Scientific) using serially diluted BSA to establish Standard Curve d: The toal lipids measured through Lipids Quantification Kit (Colorimetric) (Cell Biolabs, Inc.) using serially diluted Purified Lipid Standard to establish Standard Curve with DMSO as solvent e: The total protein from YEB medium is within the range of 11%~14% f: 1 L of YEB medium is about 20.75 g, after cultural and drying process ~20% of the total contents were lost; not all dried mass was recovered.

FIG. 23

SEQUENCE LISTING

```
<160> NUMBER OF SEQ ID NOS: 1

<210> SEQ ID NO 1
<211> LENGTH: 1476
<212> TYPE: DNA
<213> ORGANISM: Unknown
<220> FEATURE:
<223> OTHER INFORMATION: Chromobacterium spp. (Csp_P), new species

<400> SEQUENCE: 1

gggaaagggg gcctgcttta ccatgcaagt cgaacggtaa cagggtgctt gcaccgctga      60

cgagtggcga acgggtgagt aatgcatcgg aatgtaccgt gtaatggggg atagctcggc     120

gaaagccgga ttaataccgc atacgccctg agggggaaag tgggggaccg aaaggcctca     180

cgttatacga gcagccgatg tctgattagc tagttggtga ggtaaaggct caccaaggcg     240

tcgatcagta gcgggtctga gaggatgatc cgccacactg ggactgagac acggcccaga     300

ctcctacggg aggcagcagt ggggaatttt ggacaatggg cgcaagcctg atccagccat     360

gccgcgtgtc tgaagaaggc cttcgggttg taaaggactt ttgtccggga gcaaatccta     420

gtggttaata accgctgggt ctgagagtac cggaagaata agcaccggct aactacgtgc     480
```

-continued

```
cagcagccgc ggtaatacgt agggtgcaag cgttaatcgg aattactggg cgtaaagcgt    540

gcgcaggcgg ttgtgcaagt ctgatgtgaa agccccgggc ttaacctggg aacggcattg    600

gagactgcac gactagagtg cgtcagaggg gggtagaatt ccgcgtgtag cagtgaaatg    660

cgtagagatg cggaggaata ccgatggcga aggcagcccc ctgggatgac actgacgctc    720

atgcacgaaa gcgtggggag caaacaggat tagataccct ggtagtccac gccctaaacg    780

atgtcaacta gctgttgggg gtttgaatcc ttggtagcgt agctaacgcg agaagttgac    840

cgcctgggga gtacggccgc aaggttaaaa ctcaaaggaa ttgacgggga cccgcacaag    900

cggtggatga tgtggattaa ttcgatgcaa cgcgaaaaac cttacctggt cttgacatgt    960

aacgaacgct gcagagatgt ggtggtgccc gaaagggagc gttaacacag gtgctgcatg   1020

gctgtcgtca gctcgtgtcg tgagatgttg ggttaagtcc cgcaacgagc gcaacccttg   1080

ccattagttg ccatcattaa gttgggcact ctaatgggac tgccggtgac aaaccggagg   1140

aaggtgggga tgacgtcaag tcctcatggc ccttatgacc agggcttcac acgtcataca   1200

atggtcggta cagagggtcg cgaagccgcg aggtggagcc aatctcataa aaccgatcgt   1260

agtccggatc gcactctgca actcgagtgc gtgaagtcgg aatcgctagt aatcgcagat   1320

cagcatgctg cggtgaatac gttcccgggt cttgtacaca ccgcccgtca caccatggga   1380

gtgagtttca ccagaagtgg gtaggctaac cgtaaggagg ccgcttacca cggtgggatt   1440

catgactggg ggaagtcgt aacaagggca agcccc                               1476
```

METHODS FOR THE PREPARATION OF NON-LIVE *CHROMOBACTERIUM* BIOPESTICIDE

CROSS-REFERENCE TO RELATED APPLICATIONS

This application is a 35 U.S.C. § 371 U.S. national entry of International Application PCT/US2021/055361, having an international filing date of Oct. 18, 2021, which claims the benefit of U.S. Provisional Application No. 63/092,857, filed Oct. 16, 2020, which is incorporated herein by reference in its entirety.

GOVERNMENT SUPPORT CLAUSE

This invention was made with government support under grant number AID-OAA-F-16-00096, awarded by the United States Agency for International Development, and grant number 200-2017-93143, awarded by the Centers for Disease Control and Prevention. The government has certain rights in the invention.

FIELD OF THE INVENTION

The present invention relates to the field of pesticides. More specifically, the present invention provides compositions and methods for the preparation of non-live *Chromobacterium* pesticides.

INCORPORATION-BY-REFERENCE OF MATERIAL SUBMITTED ELECTRONICALLY

This application contains a sequence listing. It has been submitted electronically via EFS-Web as an ASCII text file entitled "P16318-02_ST25.txt." The sequence listing is 2,355 bytes in size, and was created on Oct. 4, 2021. It is hereby incorporated by reference in its entirety.

BACKGROUND OF THE INVENTION

Parasites, viruses and filarial worms that can be transmitted from person to person when mosquitoes feed on human blood represent a clear and present threat to human health around the world. The burden of malaria, a febrile illness caused by *Plasmodium* parasites that are transmitted by mosquitoes from the genus *Anopheles*, is particularly high. Unfortunately, even though unprecedented disease control efforts over the last 15 years have reduced the burden of disease (1), the human cost still remains high. Recent data suggests that there were an estimated 219 million cases of malaria, and approximately 435,000 deaths in 2017, many of which were young children (2).

Mosquito-transmitted arboviral diseases also have a major impact on human health, with key viruses such as dengue virus, transmitted by mosquitoes from the genera *Aedes* and *Culex*, responsible for millions of infections each year (3-6). Critically, the incidence of arboviral disease has risen greatly over the last 20 years (7), as changes in climate, mosquito distribution and human behavior have brought humans and mosquitoes into contact more frequently (8-10). These factors have also helped to promote the emergence of novel mosquito-transmitted viruses such as chikungunya and Zika (11), which have caused hundreds of thousands of infections during major outbreaks (4, 6).

Unfortunately, there are no effective, commercially available vaccines for most mosquito-transmitted diseases, and crucially, malaria parasites are rapidly developing resistance to drugs (12), while drugs for arboviruses do not currently exist. For this reason, mosquito control has long been the most common strategy employed to limit disease transmission, and historically the most common approach has been to utilize different chemical insecticides to rapidly, and effectively kill mosquitoes (13). These insecticides can be used to target both larval and adult mosquito stages, and can be used synergistically with mosquito bite prevention strategies (14). Many commonly used insecticides, including pyrethroids and organophosphates, kill by targeting the mosquito central nervous system (15-17). Others, including chitin synthesis inhibitors and juvenile hormone analogues like methoprene, act to prevent development beyond larval stages (17, 18). Concerns about the environmental impacts of chemical insecticides have sharpened focus on the development of environment-friendly mosquitocidals (19). There are also a variety biologically-derived insecticides, or biopesticides, used in mosquito control. These include the bacteria *Bacillus thuringiensis* subsp. *israelensis* (Bti) and *Lysinibacillus sphaericus*, which produce highly durable spores that form a crystal protein which shreds the mosquito gut after ingestion (20, 21). There are also entomopathogenic fungi, such as Metarhizium anisopliae, which can target and kill specific mosquito species (22).

Regular exposure to chemical insecticides has led to genetic resistance becoming increasingly prevalent in mosquito populations (23, 24), complicating mosquito control efforts (25). The implication of insecticide resistance is that no single insecticide will offer perfect, long-term control of any mosquito population. Instead, effective, long-term control will likely come through multi-faceted strategies that exploit synergies between different insecticides, thereby providing a greater chance of limiting or overcoming potential mechanisms of resistance (26). Consequently, novel mosquitocidal chemicals, and biopesticides must continue to be developed, as they will provide new options to improve or supplement existing mosquito control programs.

SUMMARY OF THE INVENTION

Given the continued high prevalence of mosquito-transmitted diseases there is a clear need to develop novel disease and vector control strategies. Biopesticides of microbial origin represent a promising source of new approaches to target disease transmitting mosquito populations. As described herein, in particular embodiments, the present inventors have developed and characterized a novel mosquito biopesticide derived from an air-dried, non-live preparation of the bacterium *Chromobacterium* sp. Panama (Family: Neisseriaceae). This preparation rapidly and effectively kills the larvae of prominent mosquito vectors including the dengue and Zika vector *Aedes aegypti*, and the human malaria vector *Anopheles gambiae*. During semi-field trials in Puerto Rico, the present inventors observed high efficacy of the biopesticide against field-derived *Ae. aegypti* populations, and against *Ae. aegypti* and *Culex* spp. larvae in natural breeding water, indicating the suitability of the biopesticide for use under more natural conditions. In addition to high efficacy, the non-live Csp_P biopesticide has a low effective dose, a long shelf life, high heat stability, and can be incorporated into attractive larval baits, all of which are desirable characteristics for a biopesticide.

Accordingly, in one aspect, the present invention provides methods for producing a non-live *Chromobacterium* biopesticide. In one embodiment, the method comprises the steps of (a) growing the *Chromobacterium* in a bioreactor with culture medium; (b) oxygenating the *Chromobacterium* during step (a); (c) adding an antibiotic to the *Chromobacterium* culture; (d) incubating the *Chromobacterium* culture under hypoxic conditions; (e) pouring the *Chromobacterium* culture on to a substrate; (f) air drying the *Chromobacterium*; and (g) crushing the dried *Chromobacterium* into a powder.

In a specific embodiment, oxygenating step (b) is accomplished by shaking the *Chromobacterium* in the bioreactor. In particular embodiments, the antibiotic is hygromycin B. In another embodiment, step (d) is performed at room temperature. In yet another embodiment, step (e) is performed at room temperature. In certain embodiments, the *Chromobacterium* is *Chromobacterium* sp. Panama. The present invention also provides a composition comprising the non-live *Chromobacterium* biopesticide produced by the methods described herein.

In another embodiment, a method for producing a non-live *Chromobacterium* biopesticide comprises the steps of (a) growing the *Chromobacterium* in a bioreactor with culture medium; (b) oxygenating the *Chromobacterium* during step (a); (c) adding an antibiotic to the *Chromobacterium* culture; (d) incubating the *Chromobacterium* culture under hypoxic conditions; (e) performing an organic extraction of the *Chromobacterium*; and (f) collecting the organic phase comprising the *Chromobacterium.*

In yet another embodiment, the method further comprises the step of evaporating the organic phase of step (f). In a more specific embodiment, the method further comprises the step of sonicating the dried *Chromobacterium*. In certain embodiments, oxygenating step (b) is accomplished by shaking the *Chromobacterium* in the bioreactor. In another specific embodiment, the antibiotic is hygromycin B. In particular embodiments, step (d) is performed at room temperature. In a further embodiment, the *Chromobacterium* is *Chromobacterium* sp. Panama. The present invention also provides compositions comprising the non-live *Chromobacterium* biopesticide produced by the methods described herein.

In another aspect, the present invention provides compositions comprising a non-live *Chromobacterium* powder. In particular embodiments, the non-live *Chromobacterium* powder is free of cyanide. In other embodiments, the non-live *Chromobacterium* was grown under hypoxic conditions. In certain embodiments, the non-live *Chromobacterium* is cultured with hygromycin B. In further embodiments, the hygromycin B does not kill the *Chromobacterium.*

BRIEF DESCRIPTION OF THE FIGURES

(FIG. 3B) and in independent experiments, at room temperature (22° C.) or 70° C. (FIG. 3C) in accelerated shelf life tests in order to assess the durability of the active ingredient. The 30° C., 37° C. and 54° C. treatments did not differ in efficacy from the room temperature treatment (Cox regression; P>0.05), while the 70° C. still killed 100% of the larvae exposed but took significantly longer to do so (Cox Regression: P<0.0001), with these results suggesting that the active ingredient was highly heat-stable, and likely to have a long shelf life. Three other common mosquito-associated bacteria were cultured, and dried according to the same protocol used to produce non-live Csp_P powder. 100 mg of each of these powders was added to attractive pellets and provided to ROCK larvae (FIG. 3D). None of these three preparations caused mortality that was significantly different to larvae treated with no bacteria control pellets (Cox Regression: P>0.05), suggesting that the larvicidal effect the present inventors observed in the present inventors' results was not due to the culturing methods, and not universal amongst all bacteria. In all experiments, larvae were reared in groups of 30 in 300 ml de-ionized water. Lines depict the percentage of larvae surviving at each day post-treatment (±s.e.m.) for three experimental replicates, with each containing three cages per treatment.

FIG. 18A: Mortality assays with 500 mg/ml unfiltered and centrifuged/filtered (to remove cell debris) Csp_P airdried powder in 50% and 100% ASB, and 10% sucrose (sugar). Mosquitoes also fed efficiently on 100% ASB through plastic and parafilm pouches (shown in FIG. 19). FIG. 18B: The vials contain 500 mg/ml unfiltered Csp_P airdried powder in 50% (left) and 100% (right) ASB, and the Csp_P remains in solution, does not settle upon several days' storage without agitation.

FIG. 22A: Accelerated shelf life-assays of 500 mg/ml Csp_P airdried powder in the 50% ASB incubated at 52° C. and 70° C. for two weeks prior to mortality assays. FIG. 22B: Shelf life-assays of 500 mg/ml Csp_P airdried powder in the 100% ASB incubated at room temperature for two weeks prior to mortality assays.

FIG. 23. Quantification of liquid culture (after the final 3 days shaking step) and airdried powder in terms of dry weight, OD, numbers of cells, protein and lipid content.

DETAILED DESCRIPTION OF THE INVENTION

Figures 1A, 1B, 1C, 1D, 1E, 1F, 1G, 1H:
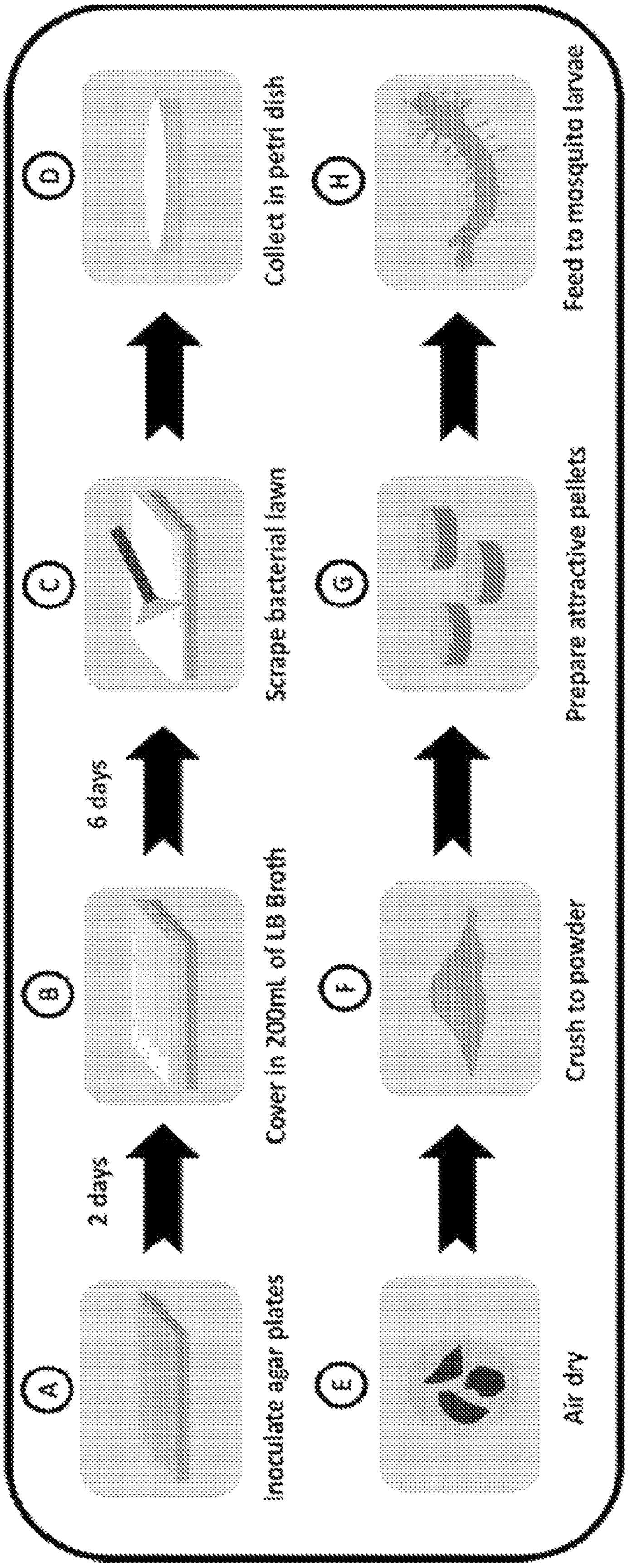
FIG. 1A-1H. Workflow for preparing the non-live Csp_P biopesticide. Prepare large plates with 200 ml of LB agar, then inoculate each with 200 μL of Csp_P culture (FIG. 1A). Allow plates to grow for 2 days at 30° C., and then inoculate with 200 ml of LB broth (FIG. 1B). Grow for 5 days, then decant the liquid phase, let plates sit for 24 hours and then scrape off the bacterial lawn (FIG. 1C). Collect bacterial lawn in a petri dish (FIG. 1D). Air dry preparation in fume hood (FIG. 1E). Once dry, crush preparation to powder with a mortar and pestle (FIG. 1F). Incorporate non-live Csp_P powder into gelatin/fishmeal attractive pellets (FIG. 1G). Feed pellets containing 100 mg of powder to target mosquito larvae (FIG. 1H).

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The present inventors have developed a novel preparation to kill mosquitoes from an abundant soil bacterium, *Chromobacterium* sp. Panama. In certain embodiments, this preparation is an air-dried powder containing no live bacteria, which can be incorporated into an attractive bait and fed directly to mosquito larvae. The present inventors demonstrated that the preparation has broad spectrum activity against the larval form of the mosquitoes responsible for the transmission of malaria and the dengue, chikungunya, Yellow Fever, West Nile and Zika viruses, as well as mosquito larvae that are already resistant to commonly used mosquitocidal chemicals. The present invention possesses many favorable traits: it kills at a low dosage, and does not lose activity when exposed to high temperatures, all of which suggest it could eventually become an effective new tool for controlling mosquitoes and the diseases they spread.

I. Definitions

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, within 4-fold, within 3-fold, or within 2-fold, of a value. Where particular values are described in the application and claims, unless otherwise stated the term "about" meaning within an acceptable error range for the particular value should be assumed.

The term “substantially,” as used herein, means at least about 80%, at least about 85%, at least about 90%, at least about 91%, at least about 92%, at least about 93%, at least about 94%, at least about 95%, at least about 96%, at least about 97%, at least about 98%, at least about, or at least about 99%, including, for example, at least about 99.9%. In some embodiments, the term “substantially” can mean completely, or about 100%.

The term “whole broth culture” refers to a liquid culture containing both cells and media. If bacteria are grown on a plate, the cells can be harvested in water or other liquid, whole culture.

The term “supernatant” refers to the liquid remaining when cells grown in broth or are harvested in another liquid from an agar plate and are removed by centrifugation, filtration, sedimentation, or other means well known in the art.

The term “filtrate” refers to liquid from a whole culture that has passed through a membrane.

The term “extract” refers to liquid substance removed from cells by a solvent (water, detergent, and buffer) and separated from the cells by centrifugation, filtration or other method.

The term “metabolite” refers to a compound, substance or byproduct of a fermentation of a microorganism, or supernatant, filtrate, or extract obtained from a microorganism that has insecticidal activity.

The term “insecticidal activity” means that a substance has a detrimental effect on an insect, including but not limited to killing a target insect, increasing mortality, or inhibiting the incidence, growth, development or reproduction of a target insect.

As used herein, the term “pest” refers to organisms that cause damage to plants or other organisms, are present where they are not wanted, or otherwise are detrimental to humans, for example, by impacting human agricultural methods or products. Pests may include, for example, invertebrates (e.g., insects, nematodes, or mollusks), microorganisms (e.g., phytopathogens, endophytes, obligate parasites, facultative parasites, or facultative saprophytes), such as bacteria, fungi, or viruses; or weeds.

As used herein the term “additional agent” refers to a small molecule, chemical, organic, or inorganic molecule that can be administered to or otherwise used to treat insects, pests and the like, including insects that compete with humans for food, destroy property, spread disease, or are a nuisance. In one embodiment, the “additional agent” is a pesticide. The term “additional agent” further encompasses other bioactive molecules such as antivirals pesticides, antifungals, antihelminthics, nutrients, sucrose and/or agents that stun or slow insect movement.

As used herein, the term “pesticide” refers to any an agent, composition, or substance therein, that controls or decreases the fitness (e.g., kills or inhibits the growth, proliferation, division, reproduction, or spread) of an agricultural, environmental, or domestic/household pest, such as an insect, mollusk, nematode, fungus, bacterium, or virus. Pesticides are understood to encompass naturally occurring or synthetic insecticides (larvicides or adulticides), insect growth regulators, acaricides (miticides), molluscicides, nematicides, ectoparasiticides, bactericides, fungicides, or herbicides. The term “pesticide” or “pesticidal agent” may further encompass other bioactive molecules such as antibiotics, antivirals, pesticides, antifungals, antihelminthics, nutrients, and/or agents that stun or slow insect movement. In some embodiments, the pesticide is an allelochemical. As used herein, “allelochemical” or “allelochemical agent” is a substance produced by an organism (e.g., a plant) that can effect a physiological function (e.g., the germination, growth, survival, or reproduction) of another organism (e.g., a pest).

As used herein, the term “untreated” refers to a plant or plant pest that has not been contacted with or delivered a biopesticide composition including a separate plant that has not been delivered biopesticide composition, the same plant undergoing treatment assessed at a time point prior to delivery of the biopesticide composition, or the same plant undergoing treatment assessed at an untreated part of the plant.

As used herein, the term “administering” encompasses any method by which an insect can come into contact with a composition comprising a biopesticide described herein. An insect or pest can be exposed to a composition by direct uptake (e.g., by feeding). Alternatively, an insect can come into direct contact with a composition comprising the biopesticide. For example, an insect, pest and the like, can come into contact with a surface or material treated with a composition comprising the biopesticide. In certain embodiments, the terms can be used interchangeably with the term “treating” or “treatment.”

As used herein, “delivering” or “contacting” refers to applying to a plant or plant pest, a biopesticide composition either directly on the plant or plant pest, or adjacent to the plant or plant pest, in a region where the composition is effective to alter the fitness of the plant or plant pest. In methods where the composition is directly contacted with a plant, the composition may be contacted with the entire plant or with only a portion of the plant.

As used herein, “decreasing the fitness of a pest” refers to any disruption to pest physiology, or any activity carried out by the pest, as a consequence of administration of a biopesticide composition described herein, including, but not limited to, any one or more of the following desired effects: (1) decreasing a population of a pest by about 10%, 20%, 30%, 40%, 50%, 60%, 70%, 80%, 90%, 95%, 99%, 100% or more; (2) decreasing the reproductive rate of a pest (e.g., insect) by about 10%, 20%, 30%, 40%, 50%, 60%, 70%, 80%, 90%, 95%, 99%, 100% or more; (3) decreasing the mobility of a pest by about 10%, 20%, 30%, 40%, 50%, 60%, 70%, 80%, 90%, 95%, 99%, 100% or more; (4) decreasing the body weight of a pest by about 10%, 20%, 30%, 40%, 50%, 60%, 70%, 80%, 90%, 95%, 99%, 100% or more; (5) decreasing the metabolic rate or activity of a pest by about 10%, 20%, 30%, 40%, 50%, 60%, 70%, 80%, 90%, 95%, 99%, 100% or more; or (6) decreasing plant infestation by a pest by about 10%, 20%, 30%, 40%, 50%, 60%, 70%, 80%, 90%, 95%, 99%, 100% or more. A decrease in pest fitness can be determined in comparison to a pest to which the biopesticide composition has not been administered.

As used herein, the term “formulated for delivery to a plant or a plant pest” refers to a biopesticide composition that includes an agriculturally acceptable carrier.

As used herein, the term “infestation” refers to the presence of unwanted pests on a plant, e.g., colonization or infection of a plant, a part thereof, or the habitat surrounding a plant, by a plant pest, particularly where the infestation decreases the fitness of the plant. A “decrease in infestation” or “treatment of an infestation” refers to a decrease in the number of pests on or around the plant (e.g., by about 1%, 2%, 5%, 10%, 20%, 30%, 40%, 50%, 60%, 70%, 80%, 90%, or %100) or a decrease in symptoms or signs in the plant that are directly or indirectly caused by the pest (e.g., by about 1%, 2%, 5%, 10%, 20%, 30%, 40%, 50%, 60%, 70%, 80%, 90%, or %100) relative to an untreated plant.

Infestation or associated symptoms can be identified by any means of identifying infestation or related symptoms. For example, the decrease in infestation in one or more parts of the plant may be in an amount sufficient to "substantially eliminate" an infestation, which refers to a decrease in the infestation in an amount sufficient to sustainably resolve symptoms and/or increase plant fitness relative to an untreated plant.

As used herein, "increasing the fitness of a plant" refers to an increase in the production of the plant, for example, an improved yield, improved vigor of the plant or quality of the harvested product from the plant. An improved yield of a plant relates to an increase in the yield of a product (e.g., as measured by plant biomass, grain, seed or fruit yield, protein content, carbohydrate or oil content or leaf area) of the plant by a measurable amount over the yield of the same product of the plant produced under the same conditions, but without the application of the instant compositions or compared with application of conventional pesticides. For example, yield can be increased by at least about 0.5%, about 1%, about 2%, about 3%, about 4%, about 5%, about 10%, about 20%, about 30%, about 40%, about 50%, about 60%, about 70%, about 80%, about 90%, about 100%, or more than 100%. Yield can be expressed in terms of an amount by weight or volume of the plant or a product of the plant on some basis. The basis can be expressed in terms of time, growing area, weight of plants produced, or amount of a raw material used. An increase in the fitness of plant can also be measured by other means, such as an increase or improvement of the vigor rating, the stand (the number of plants per unit of area), plant height, stalk circumference, plant canopy, visual appearance (such as greener leaf color), root rating, emergence, protein content, increased tillering, bigger leaves, more leaves, less dead basal leaves, stronger tillers, less fertilizer needed, less seeds needed, more productive tillers, earlier flowering, early grain or seed maturity, less plant verse (lodging), increased shoot growth, earlier germination, or any combination of these factors, by a measurable or noticeable amount over the same factor of the plant produced under the same conditions, but without the administration of the instant compositions or with application of conventional pesticides.

II. *Chromobacterium* sp_Panamam (Csp_P)

The present inventors previously discovered a new species of *Chromobacterium* bacterium, which exhibits insecticidal activity against mosquitoes such as *Anopheles* and *Aedes* mosquitoes. The species was designated as *Chromobacterium* sp_Panamam (Csp_P).

The unique strain of the invention mediates insecticidal activity upon exposure to either larval or adult mosquito stages through the breeding water or nectar meal, respectively. Without being limited by any particular theory or mechanism, these studies suggest that Csp_P mediated mortality may be the result of a mosquitocidal factor or systemic infection through dissemination into the hemolymph; alternatively, its colonization of the midgut (or other tissues) might in some other way interfere with vital functions of the mosquito.

The full length Csp_P 16S rDNA gene sequence is shown in SEQ ID NO:1. The present invention is also directed to *Chromobacterium* strains which have a 16S rDNA gene sequence of SEQ ID NO:1. Such strains may be isolated for example using appropriate nucleotide primers and identified using the full length 16S rDNA gene sequence (SEQ ID NO:1).

III. Methods for the Preparation of Non-Live *Chromobacterium* Csp_P-Based Biopesticide for Targeting Mosquitoes and Other Insects A. Preparation of Liquid Culture-Based Csp_P Powder Biopesticide In particular embodiments, the materials for the production protocol include:

1. Csp_P stock in 50% glycerol, 1:1 in LB broth stored at −80° C.
2. Yeast Extract Broth (YEB). 10 g tryptone, 5 g yeast extract, 5 g sucrose, 5 g sodium chloride, 0.25 g $MgSO_4{*}7H_2O$ in 1 L DI $H_2O$. Autoclave for 30 mins at 121° C.
3. Hygromycin B (Sigma H3274)—stored in 500 μL aliquots at 5 mg/ml, at −30° C.
4. 10% sucrose
5. 500 ml Erlenmeyer flask
6. Aluminium foil
7. Shaker set to 30° C. and 200 rpm
8. 1.5 ml sterile plastic tubes
9. Fume hood
10. 45 mm diameter sterile filter paper
11. 22.5 cm×22.5 cm large plastic plates (Corning)
12. Glass petri dishes
13. Mortar and pestle In certain embodiments, the method comprises:

1. Add 150 ml of sterile YEB to a sterile 500 ml flask, and inoculate with 100 μL of frozen Csp_P stock. Cover mouth of flask with aluminium foil.
2. Grow on a shaker at 30° C. and 200 rpm for 72 hours.
3. Move flask to lab bench at room temperature 22° C. Add 150 μL of Hygromycin B and swirl flask to mix and seal to create a hypoxic environment. Leave undisturbed for a further 72 hours.
4. Pour into a large plastic culturing plate. Leave plate at room temperature for 7 days.
5. Pour into glass petri dishes and leave uncovered to air dry in a fume hood for 2-3 days.
6. Manually crush the air-dried biofilm into a powder using a mortar and pestle.

Figure 10:
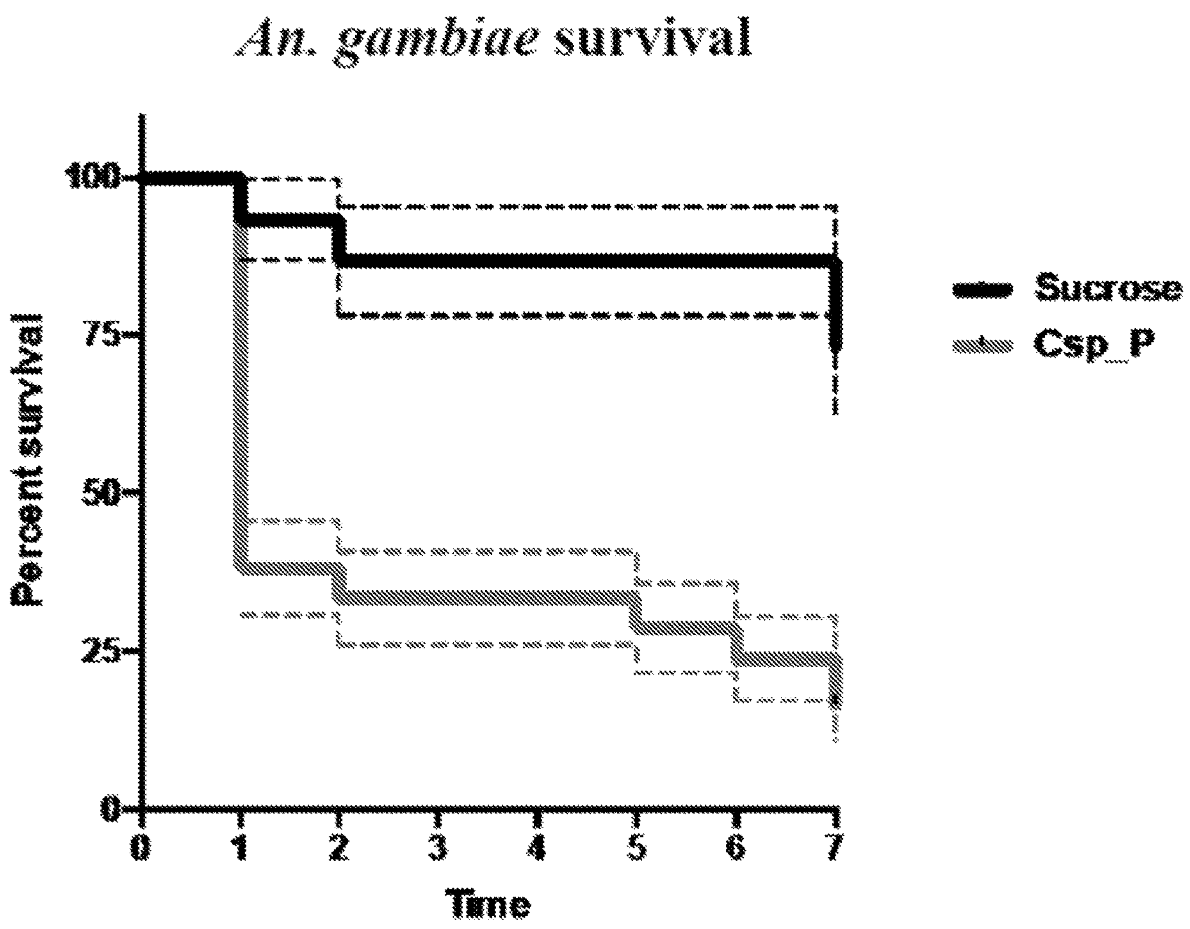
FIG. 10. Survival of adult *An. gambiae* exposed to liquid culture-based Csp_P. Liquid culture-based Csp_P powder was mixed with 10% sucrose to a final concentration of 200 mg/ml. Adult *Anopheles gambiae* (Keele) mosquitoes were exposed for 24 hours (blue line) and then provided with 10% sucrose thereafter. Control mosquitoes (black line) were fed only 10% sucrose. Survival was monitored daily. Csp_P-exposed mosquitoes experienced significant mortality compared to unexposed mosquitoes (Mantel-Cox: $X^2$-15.95, P<0.0001). One experimental replicate was performed involving three cups of 15 mosquitoes per treatment.
Figure 11:
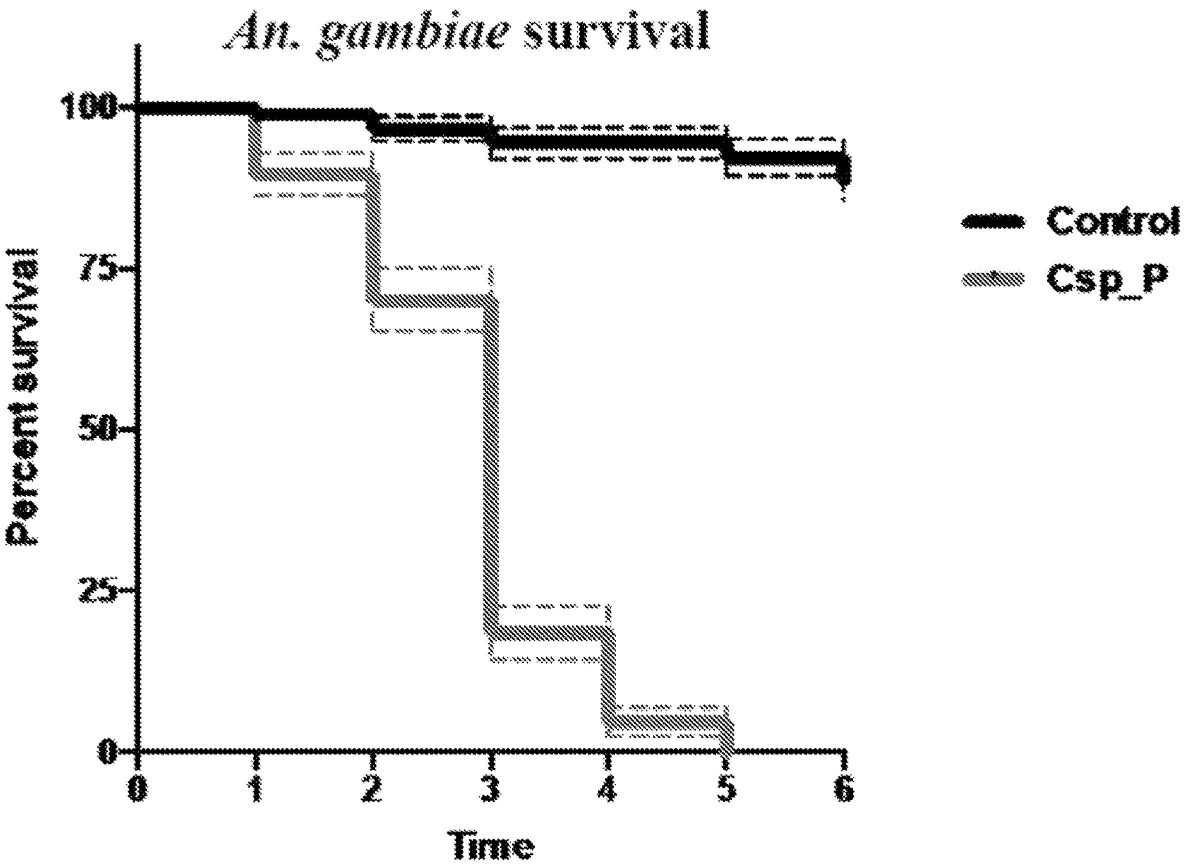
FIG. 11. Survival of larval *An. gambiae* exposed to liquid culture-based Csp_P. Agar-based attractive pellets containing 100 mg of liquid culture-based Csp_P powder (blue line) were provided to larval *Anopheles gambiae* (Keele) mosquitoes in mosquito breeders (bioquip) containing 300 ml of DI water. Control mosquitoes were fed pellets that contained no bacteria (black line). Larval survival was monitored daily. Csp_P-exposed larvae experienced significant mortality compared to unexposed mosquitoes (Mantel-Cox: $X^2$-15.95, P<0.0001). One experimental replicate was performed involving three mosquito breeders containing 30 larvae per treatment.
Figures 12A, 12B, 12C, 12D, 12E, 12F:
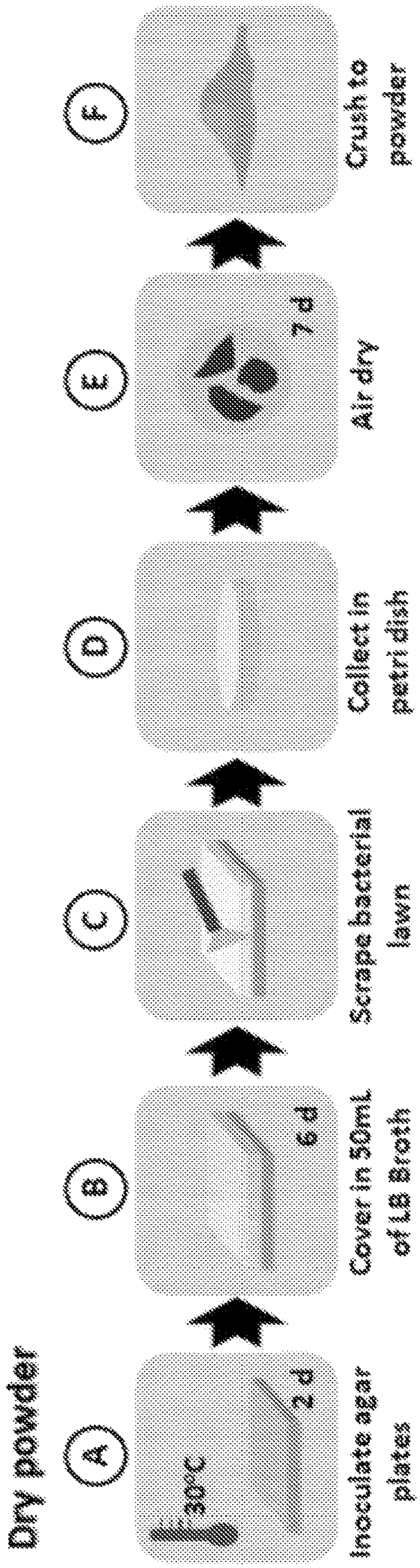
FIG. 12A-12F. Visual protocol for preparing solid-state-based Csp_P powder biopesticide.

In a further embodiment, the powder is stored in an airtight container at room temperature. See the visual protocol depicted in FIG. 9A-9F. FIG. 10 shows the results from the adulticidal assays. FIG. 11 shows the results from larvicidal assays.

B. Preparation of Solid-State-Based Csp_P Powder Biopesticide

In particular embodiments, the materials for the production protocol include:

1. Csp_P stock in 50% glycerol, 1:1 in LB broth stored at −80° C.
2. LB agar (Sigma L2897) (35 g/L in deionized water, sterilized at 121° C. for 30 mins)
3. LB broth (Sigma L3022) (20 g/L in deionized water, sterilized at 121° C. for 30 mins)
4. 20% Gelatin (Fluka 53028) (microwave until boiling) or 1.5% Agar (Sigma A1296) (20 g/L in deionized water, sterilized at 121° C. for 30 inns)
5. 22.5 cm×22.5 cm large plastic plates (Corning)
6. Sterile glass beads
7. Incubator set to 30° C.
8. Cell culture scrapers
9. Mortar and pestle In certain embodiments, the method comprises:

1. Prepare large plates with 200 ml of LB agar. Inoculate each plate with 2 ml of Csp_P stock (in 50% glycerol, stored at −80° C. and thawed just prior to inoculation), and spread across the plate surface with sterile 4 mm glass beads. Culture plates at 30° C. for 48 hours to allow biofilm to form on the surface of the LB agar.
2. Add 50 ml of sterile LB broth (20 g/L in deionized water, sterilized at 121° C. for 30 mins) to the surface of each plate using a serological pipet. Incubate plates at room temperature (22-24° C.) for a further 120 hours, then decant the liquid phase from the surface of the plates.
3. Let plates dry for a further 24 hours, then harvest the biofilm from each plate into a sterile 100 mm petri dish using a plastic scraper.
4. Collect approximately 7.5 plates worth of biofilm to fill one petri dish.
5. Air dry the collected biofilm in a fume hood over approximately 7 days.
6. Manually crush the air-dried biofilm into a powder using a mortar and pestle.

Figure 13:
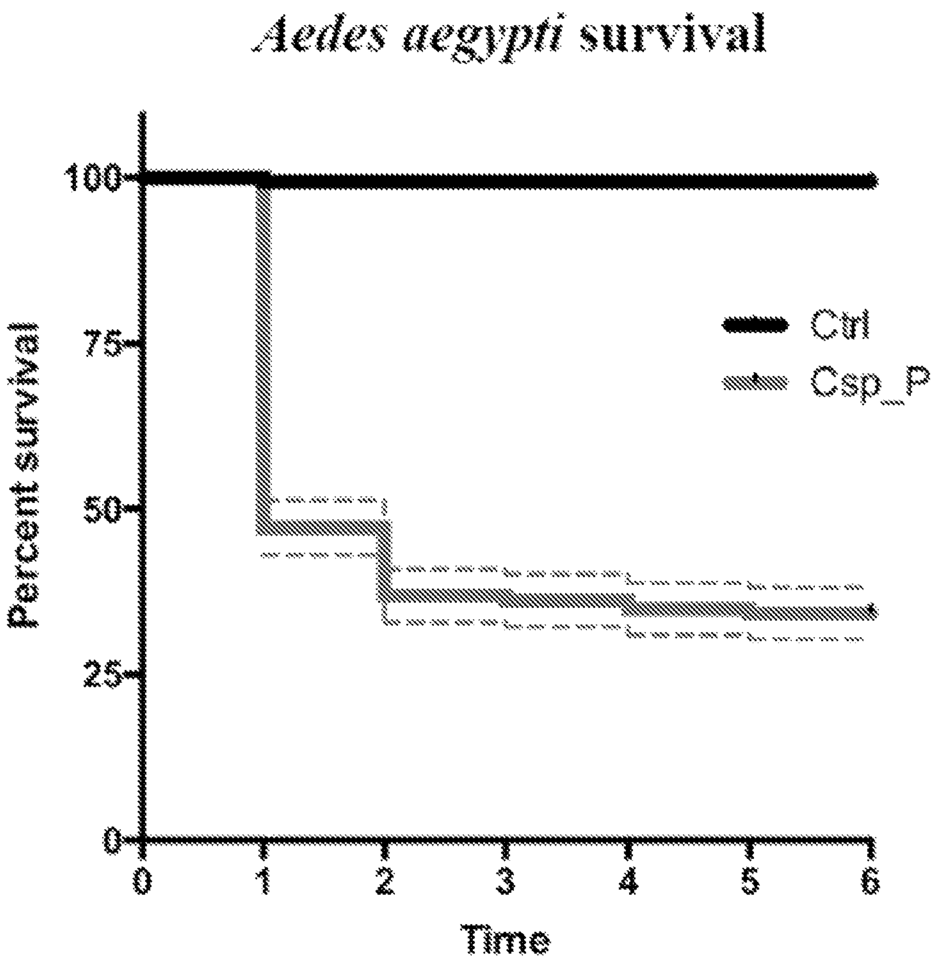
FIG. 13. Survival of adult *Ae. aegypti* exposed to solid-state-based Csp_P. Solid-state-based Csp_P powder was mixed with 10% sucrose to a final concentration of 200 mg/ml. Adult *Aedes aegypti* (Rockefeller) mosquitoes were exposed for 24 hours (blue line) and then provided with 10% sucrose thereafter. Control mosquitoes (black line) were fed only 10% sucrose. Adult survival was monitored daily. Csp_P-exposed mosquitoes experienced significant mortality compared to unexposed mosquitoes (Mantel-Cox: $X^2$-161.80, P<0.0001). Three experimental replicates were performed, each involving three cups of 15 mosquitoes per treatment.
Figures 14A, 14B, 14C, 14D, 14E, 14F, 14G, 14H, 14I:
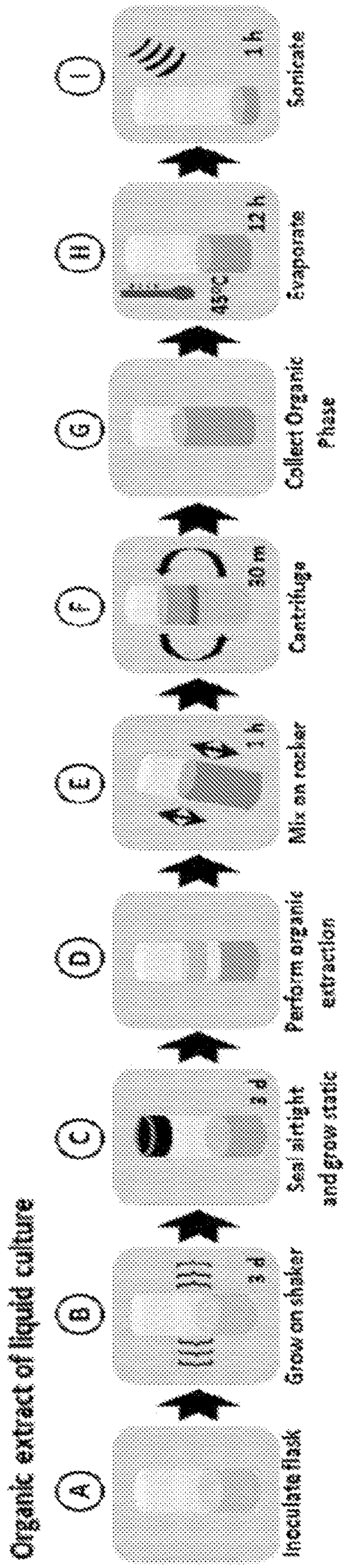
FIG. 14A-14I. Visual protocol for organic extraction-based insecticidal enrichment of Csp_P liquid and solid state culture.

Powder can be stored in an airtight container at room temperature for at least 12 months. See the visual protocol depicted in FIG. 12A-12F. See also FIG. 13 for the results from the adulticidal assays.

Figure 2A:
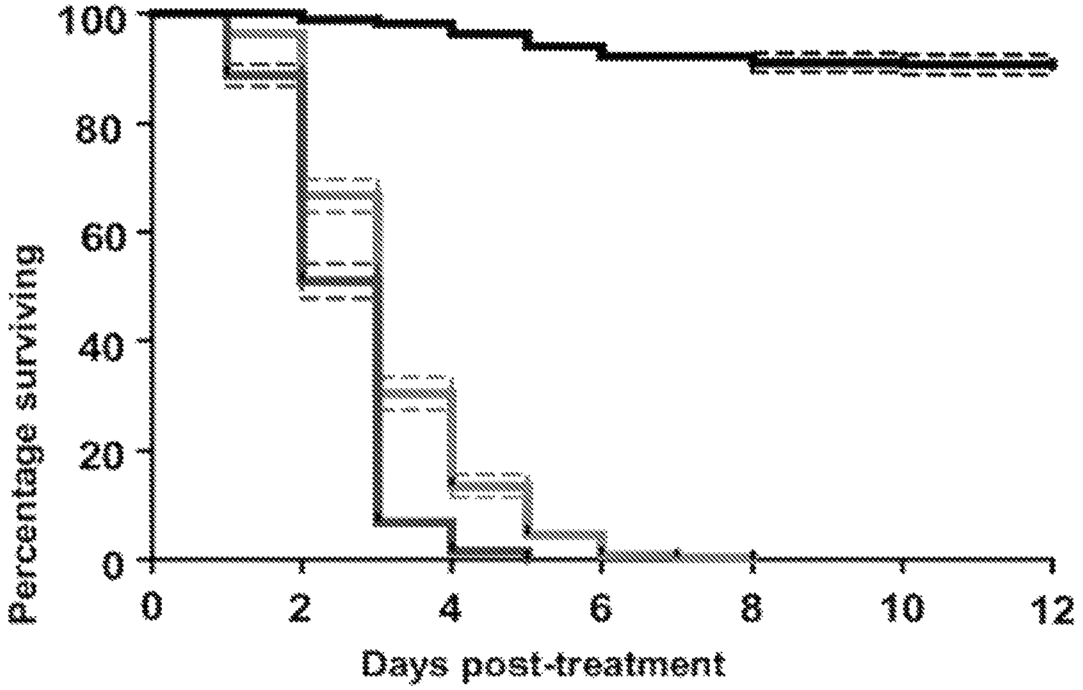
FIG. 2A-2D. Non-live Csp_P effectively kills the larvae of important mosquito vector species, including those resistant to common chemical insecticides. At 3 days post-hatching, larvae from *Ae. aegypti* ROCK strain (FIG. 2A), pyrethroid-resistant *Ae. aegypti* strain NR-48830 (FIG. 2B), *An. gambiae* Keele strain (FIG. 2C), and *Cx. quinquefasciatus* JHB strain (FIG. 2D) were fed with an attractive pellet containing fishmeal and 20% gelatin. Larvae were treated with one of three different types of pellets: no bacteria controls (black lines), live *Chromobacterium* Csp_P (red lines), or non-live *Chromobacterium* Csp_P (blue lines). Non-live Csp_P was an effective larvicide for each line, with an average time to death of 3.13±0.08 days (±s.e.m.) for ROCK, 3.40±0.13 days for NR-48830, 2.25±0.09 days for Keele, and 1.68±0.05 days for JHB. Larvae were reared in groups of 25-30 in 300 ml de-ionized water. Lines depict the percentage of larvae surviving at each day post-treatment (±s.e.m.) for three experimental replicates, with each containing three cages per treatment.
Figure 2B:
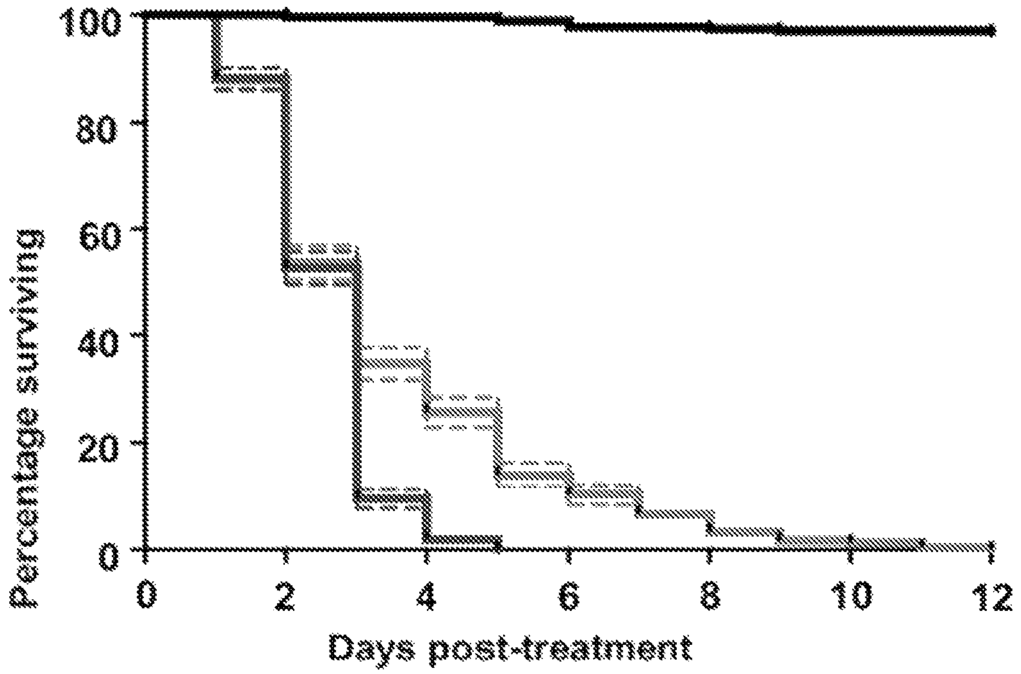
Figure 2C:
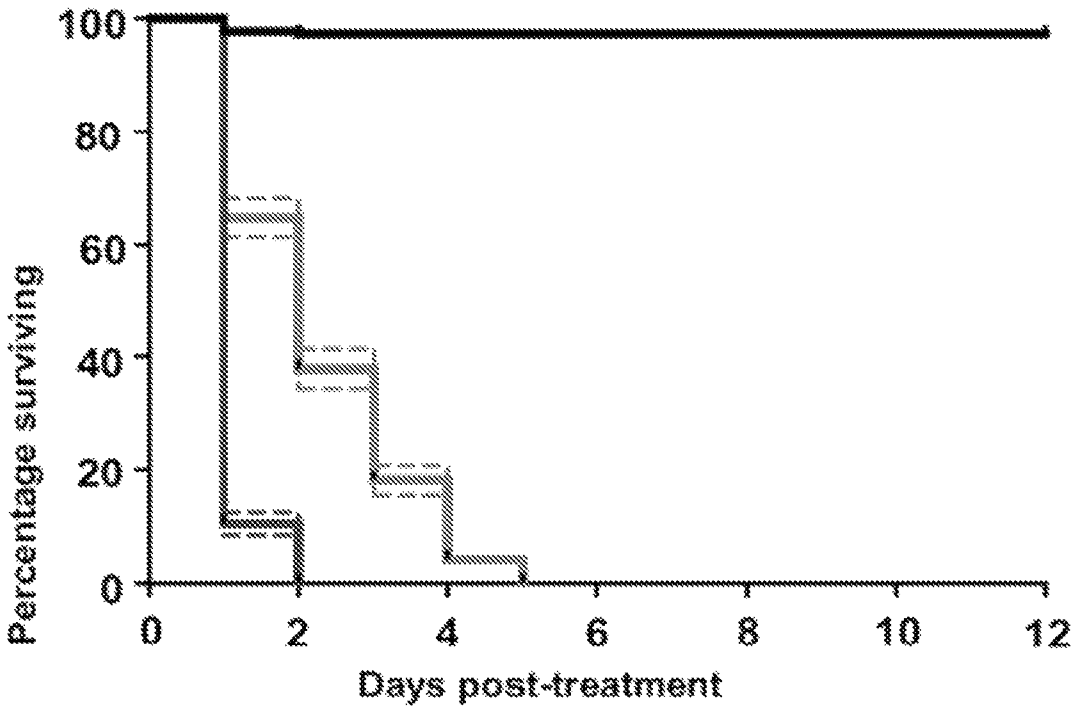
Figure 2D:
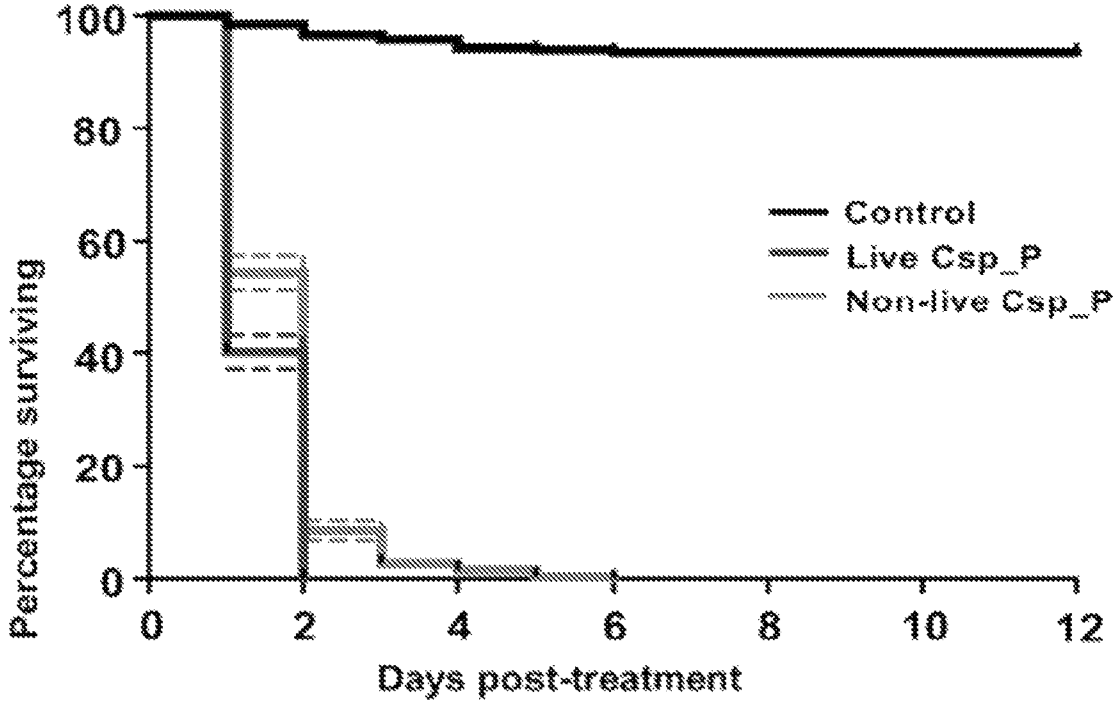

FIG. 2A-2D show the results from larvicidal assays. Survival of larval mosquitoes exposed to solid-state-based Csp_P: Attractive pellets containing 100 mg of solid-state-based Csp_P powder were provided to larvae from major mosquito vectors: *Aedes aegypti* Rockefeller larvae (FIG. 2A), Pyrethroid-resistant *Aedes aegypti* NR-48830 larvae (FIG. 2B), *Anopheles gambiae* Keele larvae (FIG. 2C), and *Culex quinquefasciatus* JHB larvae (FIG. 2D). Larvae were maintained in mosquito breeders (bioquip) containing 300 ml of DI water. Larvae were fed either a no bacteria control pellet (black lines), a pellet containing 1 ml of live Csp_P overnight culture (red lines), or solid-state-based Csp_P powder (blue lines). Survival was monitored daily. In all experiments, mosquito larvae exposed to solid-state-based Csp_P powder-containing pellets experienced significant mortality compared to unexposed mosquitoes. For each mosquito line, three experimental replicates were performed each involving three mosquito breeders containing 30 larvae per treatment.

Figure 3A:
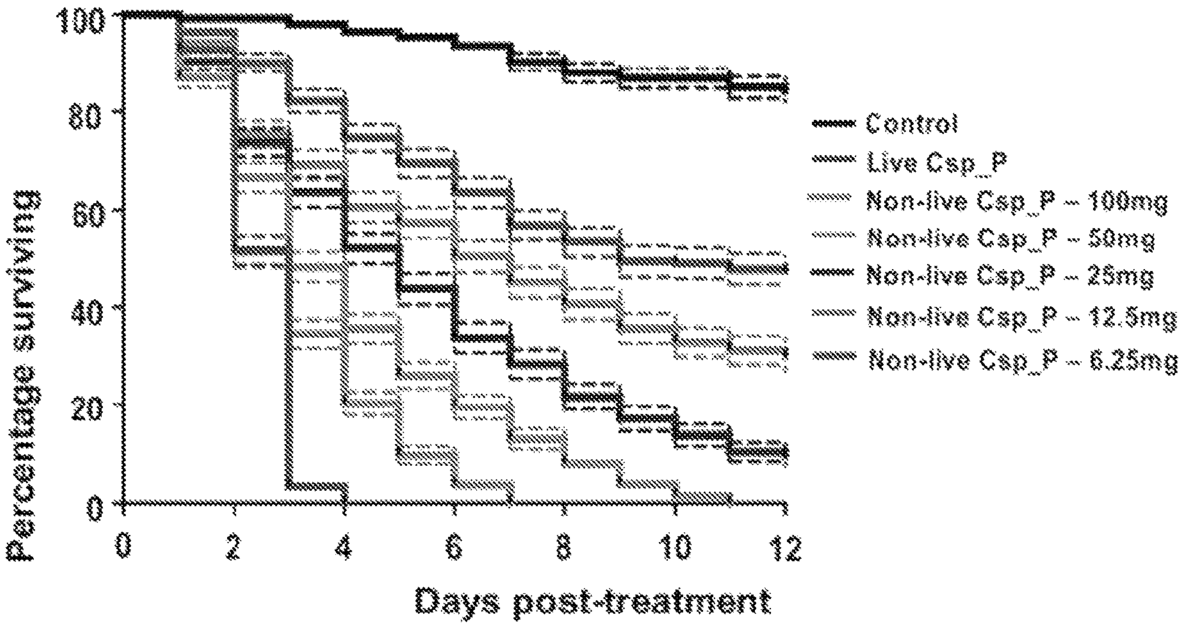
FIG. 3A-3D. The Non-live Csp_P biopesticide has a low effective dose, and a durable active ingredient that is not produced by other common mosquito-associated bacteria. ROCK larvae were fed pellets containing different doses of Non-live Csp_P (FIG. 3A). Doses of 100 mg and 50 mg killed 100% of larvae, while doses of 25 mg, 12.5 mg and 6.25 had partial mortality and delayed pupation. A $LD_{50}$ was calculated at 11.35 mg per liter of water in the larval habitat. Non-live Csp_P powder was heat treated at room temperature (22° C.), 30° C., 37° C. or 54° C.

FIG. 3A shows the results from a dose-response assay for *Ae. aegypti* larvae exposed to solid-state-based Csp_P. Cohorts of *Ae. aegypti* Rockefeller larvae were fed on attractive pellets containing different doses of solid-state-based Csp_P, ranging from 6.25 mg through 100 mg. Larvae were maintained in mosquito breeders (bioquip) containing 300 ml of DI water. Based on the results of these experiments, the present inventors calculated a 50% Lethal Dose (LD50) of 3.40 mg of solid-state-based Csp_P per pellet, or 11.35 mg per liter of breeding site water. Three experimental replicates were performed, with each involving three mosquito breeders containing 30 larvae per treatment.

C. Organic Extraction-Based Insecticidal Enrichment of Csp_P Liquid (A) and Solid State (B) Culture.

In particular embodiments, the materials for the production protocol include:

1. Csp_P stock in 50% glycerol, 1:1 in LB broth stored at −80° C.
2. Yeast Extract Broth (YEB). 10 g tryptone, 5 g yeast extract, 5 g sucrose, 5 g sodium chloride, 0.25 g $MgSO_4*7H_2O$ in 1 L DI $H_2O$. Autoclave for 30 mins at 121° C.
3. Hygromycin B (Sigma H3274)—stored in 500 μL aliquots at 5 mg/ml, at −30° C.
4. N-Butanol (Millipore BX1780-5)
5. Tween80 (Sigma P4780)
6. 10% sucrose
7. 500 ml Erlenmeyer flask
8. Aluminium foil
9. Shaker set to 30° C. and 200 rpm
10. Rocker
11. 1 ml Pipette and tips
12. 10 ml serological pipettes
13. 1.5 ml sterile plastic tubes
14. Heat block set to 45° C.
15. Fume hood
16. Centrifuge with 15 ml tube compatible rotor
17. Sonicator
18. 45 mm diameter sterile filter paper In certain embodiments, the method comprises the steps of bacterial culturing followed by organic extraction. In a specific embodiment, bacterial culturing comprises:

1. Add 150 ml of sterile YEB to a sterile 500 ml flask, and inoculate with 100 μL of frozen Csp_P stock. Cover mouth of flask with aluminium foil.
2. Grow on a shaker at 30° C. and 200 rpm for 72 hours.
3. Move flask to lab bench at room temperature 22° C. Add 150 μL of Hygromycin B and swirl flask to mix and seal to create a hypoxic environment. Leave undisturbed for a further 72 hours.

In another specific embodiment, organic extraction comprises:

1. Prepare in a 15 ml tube. Add 5 ml of N-Butanol, 500 μL of Tween80 and 9.5 ml of Csp_P live culture to tube.
2. Mix on a rocker for 1 hr at room temperature.
3. Centrifuge tube at max speed for 20-30 mins to separate organic phase.
4. Collect the organic phase (the top phase) and remove it to another tube. There should be 4.5-5.5 ml. The organic phase from multiple tubes can be combined and stored at room temperature.
5. Prepare 1 ml aliquots of the organic phase in 1.5 ml tubes. Place on a heat block at 45° C. with lids open. Position heat block under air flow and leave to evaporate overnight.
6. Sonicate for 1 hr.

Figure 15:
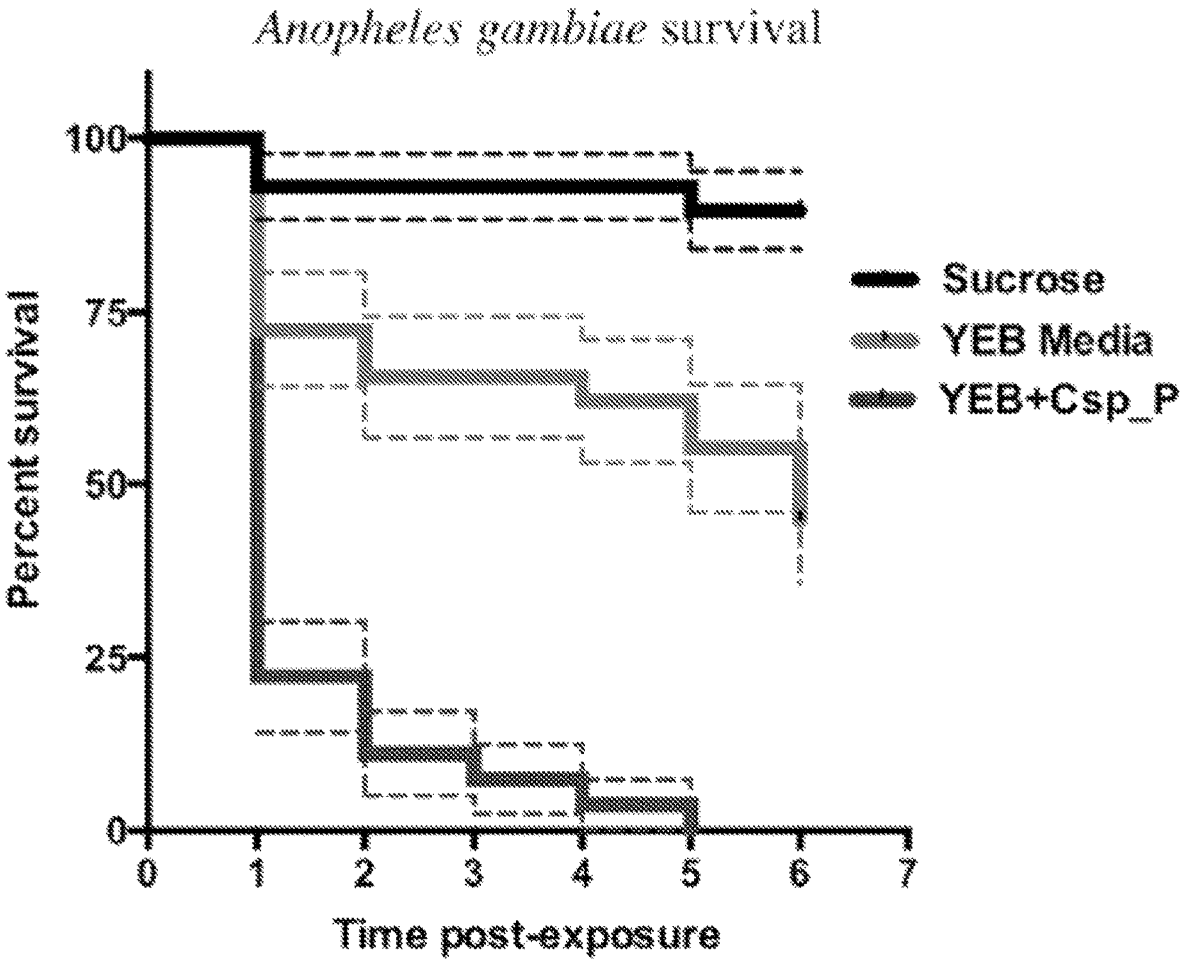
FIG. 15. Survival of adult *An. gambiae* exposed to the enriched Csp_P organic extract. One ml aliquots of Csp_P organic extract were evaporated, mixed with 1 ml of 10% sucrose and then sonicated until they went into solution. Each aliquot was placed inside a cup containing 15 adult *An. gambiae* (Keele) females, with a paper wick to facilitate feeding. Cups were provided with sucrose containing either the Csp_P enriched extract (dark blue line), or the organic extraction of the YEB media used to culture Csp_P (light blue line), or were provided only sucrose (black line) as a control. Mosquitoes were exposed for 24 hours. Mosquitoes exposed to the Csp_P organic extract experienced significant mortality compared to unexposed mosquitoes or mosquitoes that were provided with the media control (Mantel-Cox: $X^2$ —62.39, P<0.0001). Two experimental replicates were performed each involving three cups of 15 mosquitoes per treatment.
Figure 16:
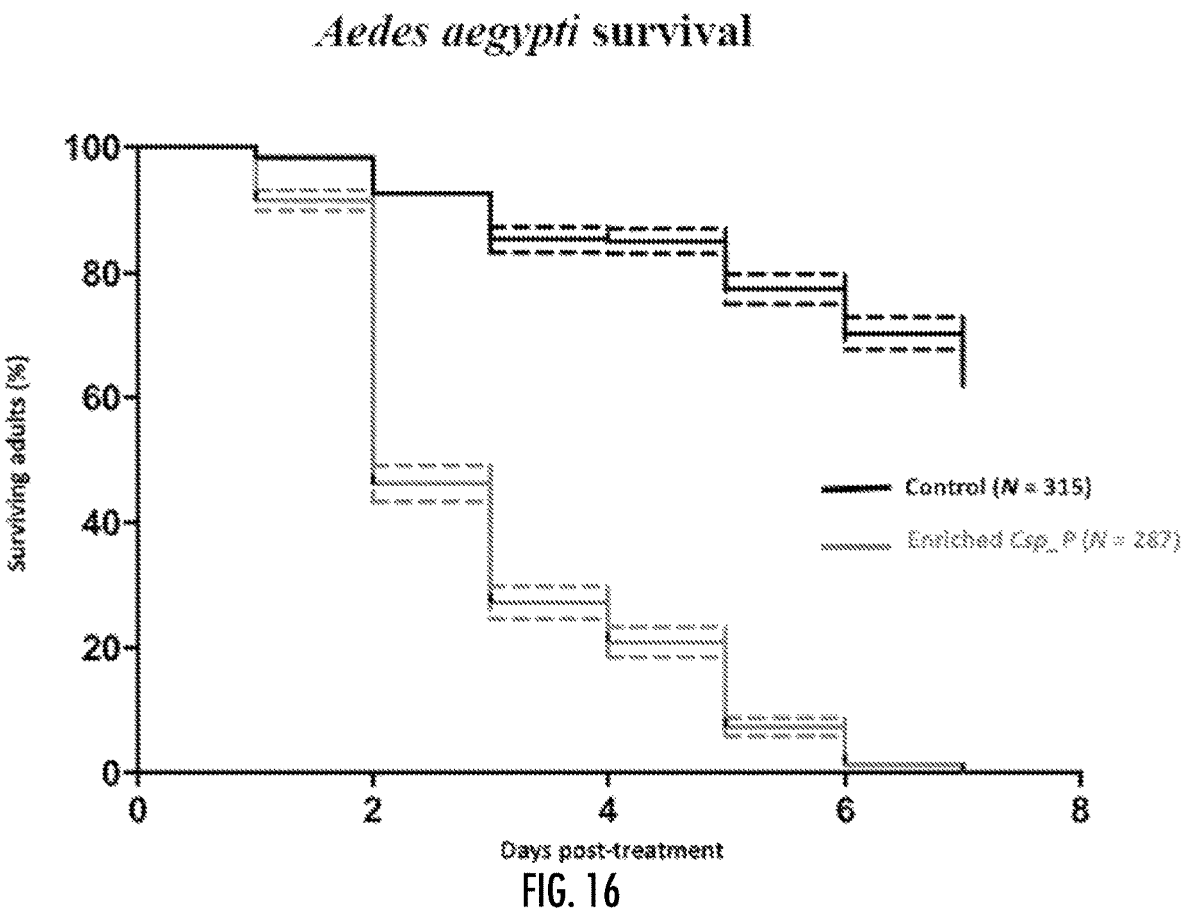
FIG. 16. Survival of adult *Ae. aegypti* exposed to the enriched Csp_P organic extract under semi-field conditions. One ml aliquots of Csp_P organic extract were evaporated, and then shipped to the present inventors' semi-field site in Puerto Rico. On-site, the aliquots were mixed with 1 ml of 10% sucrose and two aliquots were provided to cohorts of 40-70 adult female *Aedes aegypti* (Patillas) mosquitoes (blue line) in Bug Dorm 2 cages (Bioquip, dimensions 61×61×61 cm). Exposure was for 24 hours and these mosquitoes were fed on 10% sucrose thereafter. Control mosquitoes were maintained on 10% sucrose throughout the experiment. Mosquitoes were left exposed to ambient conditions within the semi-field facility and survival was monitored daily. Mosquitoes exposed to the Csp_P organic extract (Enriched Csp_P) experienced significant mortality compared to unexposed mosquitoes (Control) (Mantel-Cox: $X^2$ —420.27, P<0.0001). Five experimental replicates were performed.
Figure 17:
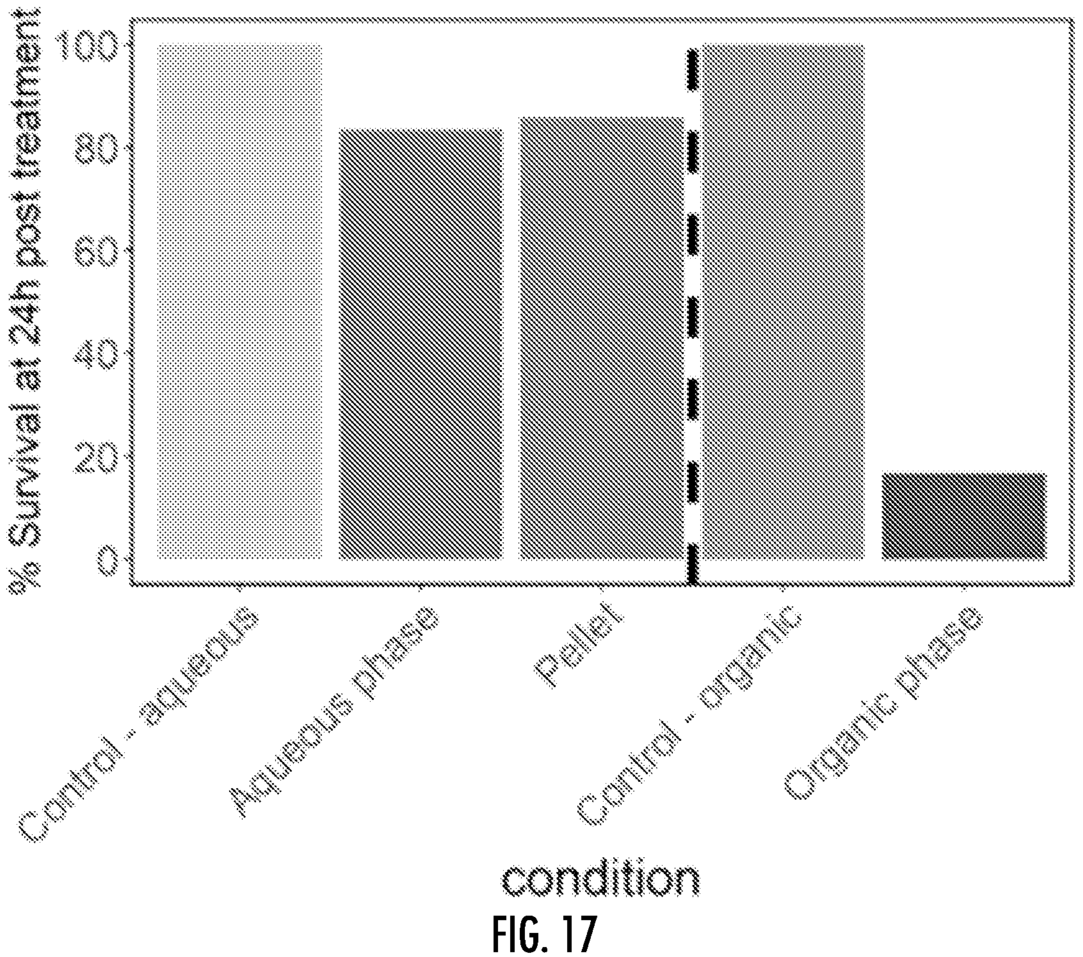
FIG. 17. Survival of *Ae. aegypti* larvae after exposure to different fractions collected from the Csp_P organic extraction. Live Csp_P or sterile media were subject to the organic extraction described above. Tween-80 and N-Butanol were added, the cultures were mixed on a rocker and then centrifuged. The aqueous phase, organic phase and pelleted cellular debris from 9.5 ml of Csp_P culture were collected, evaporated and incorporated into attractive pellets, with 50 mg of these pellets fed to *Aedes aegypti* Rockefeller larvae in 6-well plates. Significant mortality was only observed in larvae fed on pellets containing the organic phase (crimson) of the Tween80/N-Butanol Csp_P extract. Six replicates each involving 10 larvae were completed for each treatment.

The preparation can be stored in an airtight container at room temperature for at least 12 months. See the visual protocol in FIG. 14A-14I. FIGS. 15 and 16 show the results from the adulticidal assays. FIG. 17 shows the results from larvicidal assays.

IV. Preparation of Csp_P Powder Containing Agar Larvicidal Pellets

In particular embodiments, the materials for the production protocol include:

A. 1.5% Agar (Sigma A1296) (20 g/L in deionized water, sterilized at 121° C. for 30 mins)
B. Fish meal (Dirty Gardener)
C. Liquid culture-based Csp_P powder or Solid-state-based Csp_P powder
D. 24-well plate
E. Scale balance
F. Refrigerator
G. Microwave
H. 1 ml pipet and tips In certain embodiments, the method comprises:

A. Weigh out 200 mg of fishmeal using scale balance and add to 24-well plate.
B. Weigh out 200 mg of Csp_P powder using scale balance and add to 24-well plate.
C. Microwave 1.5% agar to melt.
D. Add 2 ml of melted agar to dry ingredients using pipet and mix together well.
E. Move to refrigerator and leave to set for 60-90 mins.
F. Remove from refrigerator.
G. Cut in half and use to treat mosquito larvae.

V. Administration/Application of Biopesticide Compositions

A pest/insect can be exposed to a composition comprising a non-live Csp_P preparation in combination with a delivery agent in any suitable manner that permits administering the composition to the pest/insect. For example, the pest/insect can be contacted with the composition in a pure or substantially pure form, for example a solution containing a non-live Csp_P preparation. In a particular embodiment, the composition comprises a non-live Csp_P preparation and a delivery agent. In another particular embodiment, the pest can be simply "soaked" or "sprayed" with a solution comprising a non-live Csp_P preparation.

Alternatively, the composition comprising a non-live Csp_P preparation can be linked to a food component of the pest, such as artificial nectar or sugar bait, for ease of delivery and/or in order to increase uptake of the composition by the insect. Methods for oral introduction include, for example, directly mixing a composition with the pests' food, spraying the composition in the pests' habitat or field including standing water areas. The composition can also be incorporated into the medium in which the pest grows, lives, reproduces, feeds, or infests.

In another embodiment, the composition is in the form of a bait. The bait is designed to lure the pest/insect to come into contact with the composition. In one embodiment, upon coming into contact therewith, the composition is then internalized by the pest/insect, by ingestion for example. The bait can depend on the species being targeted. An attractant can also be used. The attractant can be a pheromone, such as a male or female pheromone. The attractant acts to lure the pest/insect to the bait, and can be targeted for a particular insect or can attract a whole range of pests/insects. The bait can be in any suitable form, such as a solid, paste, pellet or powdered form.

The bait can also be carried away by the pest/insect back to the colony. The bait can then act as a food source for other members of the colony, thus providing an effective control of a large number of insects and potentially an entire insect pest colony.

The baits can be provided in a suitable "housing" or "trap". Such housings and traps are commercially available and existing traps can be adapted to include the compositions of the invention. The housing or trap can be box-shaped for example, and can be provided in pre-formed condition or can be formed of foldable cardboard for example. Suitable materials for a housing or trap include plastics and cardboard, particularly corrugated cardboard. The inside surfaces of the traps can be lined with a sticky substance in order to restrict movement of the insect once inside the trap. The housing or trap can contain a suitable trough inside which can hold the bait in place. A trap is distinguished from a housing because the insect cannot readily leave a trap following entry, whereas a housing acts as a "feeding station" which provides the insect with a preferred environment in which they can feed and feel safe from predators.

In certain embodiments of the invention, an area can be treated with a composition of the present invention, for example, by using a spray formulation, such as an aerosol or a pump spray. In certain embodiments of the invention, an area can be treated, for example, via aerial delivery, by truck-mounted equipment, or the like. Of course, various treatment methods can be used without departing from the spirit and scope of the present invention. In some embodiments, the composition is sprayed by e.g., backpack spraying, aerial spraying, spraying/dusting etc.

In specific embodiment, treatment can include use of an oil-based formulation, a water-based formulation, a residual formulation, and the like. In some embodiments, combinations of formulations can be employed to achieve the benefits of different formulation types.

A pest/insect described herein can be exposed to any of the compositions described herein in any suitable manner that permits delivering or administering the biopesticide composition to the pest. The biopesticide composition may be delivered either alone or in combination with other active (e.g., pesticidal agents) or inactive substances and may be applied by, for example, spraying, injection (e.g., microinjection), through plants, pouring, dipping, in the form of concentrated liquids, gels, solutions, suspensions, sprays, powders, pellets, briquettes, bricks and the like, formulated to deliver an effective concentration of the biopesticide composition. Amounts and locations for application of the compositions described herein are generally determined by the habits of the pest, the lifecycle stage at which the pest can be targeted by the biopesticide composition, the site where the application is to be made, and the physical and functional characteristics of the biopesticide composition. The biopesticide compositions described herein may be administered to the pest by oral ingestion, but may also be administered by means which permit penetration through the cuticle or penetration of the pest respiratory system.

In some embodiments, the pest can be simply "soaked" or "sprayed" with a solution including the biopesticide composition. Alternatively, the biopesticide composition can be linked to a food component (e.g., comestible) of the pest for ease of delivery and/or in order to increase uptake of the biopesticide composition by the pest. Methods for oral introduction include, for example, directly mixing a biopesticide composition with the pest's food, spraying the biopesticide composition in the pest's habitat or field, and the like In some embodiments, for example, the biopesticide composition can be incorporated into, or overlaid on the top of, the pest's diet. For example, the biopesticide composition can be sprayed onto a field of crops which a pest inhabits.

In some embodiments, the composition is sprayed directly onto a plant e.g., crops, by e.g., backpack spraying, aerial spraying, crop spraying/dusting etc. In embodiments where the biopesticide composition is delivered to a plant, the plant receiving the biopesticide composition may be at any stage of plant growth. For example, formulated biopesticide compositions can be applied as a seed-coating or root treatment in early stages of plant growth or as a total plant treatment at later stages of the crop cycle. In some embodiments, the biopesticide composition may be applied as a topical agent to a plant, such that the pest ingests or otherwise comes in contact with the plant upon interacting with the plant.

Delayed or continuous release can also be accomplished by coating the biopesticide composition with a dissolvable or bioerodable coating layer, such as gelatin, which coating dissolves or erodes in the environment of use, to then make the biopesticide composition available, or by dispersing the agent in a dissolvable or erodable matrix. Such continuous release and/or dispensing means devices may be advantageously employed to consistently maintain an effective concentration of one or more of the biopesticide compositions described herein in a specific pest habitat.

The biopesticide composition can also be incorporated into the medium in which the pest grows, lives, reproduces, feeds, or infests. For example, a biopesticide composition can be incorporated into a food container, feeding station, protective wrapping, or a hive. For some applications the biopesticide composition may be bound to a solid support for application in powder form or in a trap or feeding station. As an example, for applications where the composition is to be used in a trap or as bait for a particular pest, the compositions may also be bound to a solid support or encapsulated in a time-release material. For example, the compositions described herein can be administered by delivering the composition to at least one habitat where an agricultural pest (e.g., aphid) grows, lives, reproduces, or feeds.

Pesticides are often recommended for field application as an amount of pesticide per hectare (g/ha or kg/ha) or the amount of active ingredient or acid equivalent per hectare (kg a.i./ha or g a.i./ha). In some embodiments, a lower amount of biopesticide in the present compositions may be sufficient to be applied to soil, plant media, seeds plant tissue, or plants to achieve the same results as where other pesticides are applied. For example, the amount of biopesticide may be applied at levels about 2, 3, 4, 5, 6, 7, 8, 9, 10, 15, 20, 30, 50, or 100-fold (or any range between about 2 and about 100-fold, for example about 2- to 10-fold; about 5- to 15-fold, about 10- to 20-fold; about 10- to 50-fold) less than other pesticidal agents applied. Biopesticide compositions of the present invention can be applied at a variety of amounts per hectare, for example at about 0.0001, 0.001, 0.005, 0.01, 0.1, 1, 2, 10, 100, 1,000, 2,000, 5,000 (or any range between about 0.0001 and 5,000) kg/ha. For example, about 0.0001 to about 0.01, about 0.01 to about 10, about 10 to about 1,000, about 1,000 to about 5,000 kg/ha.

A. Pest Treatment

Included herein is a method of decreasing a pest infestation in a plant having an infestation, wherein the method includes delivering the biopesticide composition to the plant (e.g., in an effective amount and for an effective duration) to decrease the infestation relative to the infestation in an untreated plant. For example, the method may be effective to decrease the infestation by about 1%, 2%, 5%, 10%, 20%, 30%, 40%, 50%, 60%, 70%, 80%, 90%, 95%, 99%, 100%, or more than 100% relative to an untreated plant. In some embodiments, the method is effective to decrease the infestation by about 2×-fold, 5×-fold, 10×-fold, 25×-fold, 50×-fold, 75×-fold, 100×-fold, or more than 100×-fold relative to an untreated plant. In some embodiments, the method substantially eliminates the infestation relative to the infestation in an untreated plant. Alternatively, the method may slow progression of a plant infestation or decrease the severity of symptoms associated with a plant infestation. The composition may be sufficient to reduce (e.g., kill or repel) the pest, e.g., at least 5%, 10%, 20%, 30%, 40%, 50%, 60%, 70%, 80% or more, compared to a control.

The biopesticide compositions described herein may be useful to promote the growth of plants. For example, by reducing the fitness of harmful pests, the biopesticide compositions provided herein may be effective to promote the growth of plants that are typically harmed by a pest. This may or may not involve direct application of the biopesticide composition to the plant. For example, in instances where the primary pest habitat is different than the region of plant growth, the biopesticide composition may be applied to either the primary pest habitat, the plants of interest, or a combination of both.

In some embodiments, the plant may be an agricultural food crop, such as a cereal, grain, legume, fruit, or vegetable crop, or a non-food crop, e.g., grasses, flowering plants, cotton, hay, hemp. The compositions described herein may be delivered to the crop any time prior to or after harvesting the cereal, grain, legume, fruit, vegetable, or other crop. Crop yield is a measurement often used for crop plants and is normally measured in metric tons per hectare (or kilograms per hectare). Crop yield can also refer to the actual seed generation from the plant. In some embodiments, the biopesticide composition may be effective to increase crop yield (e.g., increase metric tons of cereal, grain, legume, fruit, or vegetable per hectare and/or increase seed generation) by about 2%, 5%, 10%, 20%, 30%, 40%, 50%, 60%, 70%, 80%, 90%, 100%, or more in comparison to a reference level (e.g., a crop to which the biopesticide composition has not been administered).

A decrease in infestation refers to a decrease in the number of pests on or around the plant or a decrease in symptoms or signs in the plant that are directly or indirectly caused by the pest. The degree of infestation may be measured in the plant at any time after treatment and compared to symptoms at or before the time of treatment. The plant may or may not be showing symptoms of the infestation. For example, the plant may be infested with a pest yet not showing signs of the infestation, e.g., a hypersensitive response (HR). An infested plant can be identified through observation of disease symptoms on the plant. The disease symptoms expressed will depend on the disease, but in general the symptoms include lesions, pustules, necrosis, hypersensitive responses, wilt, chlorosis, induction of defense related genes (e.g. SAR genes) and the like.

The skilled artisan will recognize that methods for determining plant infestation and disease by a plant pest depends on the pest and plant being tested. Infestation or associated symptoms can be identified by any means of identifying infestation or related symptoms. Various methods are available to identify infested plants and the associated symptoms. In one aspect, the methods may involve macroscopic or microscopic screening for infection and/or symptoms, quantitative PCR, or the use of microarrays for detection of infection related genes (e.g. Systemic Acquired Resistance genes, defensin genes, and the like). Macroscopic and microscopic methods for determining infestation in a plant are known in the art and include the identification of damage on plant tissue caused by infestation or by the presence of lesions, necrosis, spores, hyphae, growth of fungal mycelium, wilts, blights, spots on fruits, rots, galls and stunts, or the like. Such symptoms can be compared to non-infested plants, photos, or illustrations of infected plants or combinations thereof to determine the presence of an infection or the identity of the pathogen or both. Photos and illustrations of the symptoms of pathogen infection are widely available in the art and are available for example, from the American Phytopathological Society, St. Paul, Minn. 55121-2097. In some embodiments, the symptoms are visible to the naked eye or by a specified magnification (e.g., 2×, 3×, 4×, 5×, 10×, or 50×).

In some embodiments, the infestation or associated symptom can be identified using commercially available test kits to identify pests in plants. Such test kits are available, for example, from local agricultural extensions or cooperatives. In some embodiments, identifying a crop plant in need of treatment is by prediction of weather and environmental conditions conducive for disease development. In some embodiments, persons skilled in scouting fields of crop plants for plant disease identify a crop in need of treatment.

In some instance, an infection or associated symptom can be identified using Polymerase chain reaction (PCR)-based diagnostic assays. PCR-based assays can be used to perform PCR amplification of DNA or RNA sequences specific to the pest, including chromosomal DNA, mitochondrial DNA, or ribosomal RNA. The specific methods of identification will depend on the pathogen.

The plant can be pre-determined to have a pest infestation. Alternatively, the method may also include identifying plants having an infestation. As such, also provided are methods of treating a plant pest infestation by identifying a plant infested by a plant pest (i.e. post-infestation) and contacting the infected plant with an effective amount of a biopesticide composition such that the infestation is treated. Infestation can be measured by any reproducible means of measurement. For example, infestation can be measured by counting the number of lesions on the plant visible to the naked eye, or at a specified magnification (e.g., 2×, 3×, 4×, 5×, 10×, or 50×). In other embodiments, infestation can be measured by measuring the concentration of pests over a provided area of the plant or an area surrounding the plant.

B. Pest Prevention

Included herein is a method of preventing a plant infestation in a plant (e.g., a plant at risk of infestation), wherein the method includes delivering the biopesticide composition to the plant (e.g., in an effective amount and duration) to decrease the likelihood of infestation relative to the likelihood of infestation in an untreated plant. example, the method can decrease the likelihood of infestation by about 1%, 2%, 5%, 10%, 20%, 30%, 40%, 50%, 60%, 70%, 80%, 90%, 95%, 99%, 100%, or more than 100% relative to an untreated plant. In some embodiments, the method can decrease the likelihood of infestation by about 2×-fold, 5×-fold, 10×-fold, 25×-fold, 50×-fold, 75×-fold, 100×-fold, or more than 100×-fold relative to an untreated plant. The pests may be prevented or reduced from causing disease, the associated disease symptoms, or both.

The methods and compositions described herein may be used to reduce or prevent pest infestation in plants at risk of developing an infestation by reducing the fitness of pests that infest the plants. In some embodiments, the biopesticide composition may be effective to reduce infestation (e.g., reduce the number of plants infested, reduce the pest population size, reduce damage to plants) by about 2%, 5%, 10%, 20%, 30%, 40%, 50%, 60%, 70%, 80%, 90%, 100%, or more in comparison to a reference level (e.g., a crop to which the biopesticide composition has not been administered). In other embodiments, the biopesticide composition may be effective to prevent or reduce the likelihood of crop infestation by about 2%, 5%, 10%, 20%, 30%, 40%, 50%, 60%, 70%, 80%, 90%, 100%, or more in comparison to a reference level (e.g., a crop to which the biopesticide composition has not been administered).

These preventive methods can be useful to prevent infestation in a plant at risk of being infested by a plant pest. For example, the plant may be one that has not been exposed to a plant pest, but the plant may be at risk of infection in circumstances where pests are more likely to infest the plant, for example, in pest optimal climate conditions. Plant risk may be further increased in instances where the plant is located in a habitat where weeds in the habitat have been treated with an herbicide and disease crossover from the dying plant to the standing plant is possible. In some embodiments, identifying a crop plant in need of treatment is by prediction of weather and environmental conditions conducive for disease development.

The methods may prevent infestation for a period of time after treatment with the biopesticide composition. For example, the method may prevent infestation of the plant for several weeks after application of the biopesticide composition. For instance, the disease may be prevented for at least about 14, 15, 16, 17, 18, 19, 20, 21, 22, 23, 24, 25, 26, 27, 28, 29, 30, 35 days after treatment with a biopesticide composition. In some embodiments, the disease is prevented for at least about 40 days after delivery of a biopesticide composition to the plant. Prevention of disease may be measured by any reproducible means of measurement. In certain embodiments, infestation is assessed 7, 8, 9, 10, 11, 12, 13, 14, 15, 16, 17, 18, 19, 20, 25, 30 days after delivery of the biopesticide composition.

VI. Target Pests/Insects Using a Non-Live Csp_P Preparation

In particular embodiments, the biopesticides described herein can be used to control mosquitos including, but not limited to, *Anopheles* and *Aedes* mosquitoes.

In further embodiments, the compositions and methods of the present invention can be used to control other insects. As used herein the term "insect" describes any insect, meaning any organism belonging to the Kingdom Animals, more specific to the Phylum Arthropoda, and to the Class Insecta or the Class Arachnida. In specific embodiments of the present invention, the insect can belong to the following orders: *Acari, Araneae, Anoplura, Coleoptera, Collembola, Dermaptera, Dictyoptera, Diplura, Diptera, Embioptera, Ephemeroptera, Grylloblatodea, Hemiptera, Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera*, and *Zoraptera.*

As used herein, the terms "pest" or "insect pests" include but are not limited to the following examples: from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp, *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia Nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; *from the order Coleoptera, for example, Agriotes* spp., *Anthonomus* spp., *Atomaria linearis, Chaetocnema tibialis, Cosmopolites* spp., *Curculio* spp., *Dermestes* spp., *Epilachna* spp., *Eremnus* spp., *Leptinotarsa*

*decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.; from the order *Orthoptera*, for example, *Blatta* spp., *Blattella* spp., *Gryllotalpa* spp., *Leucophaea maderae, Locusta* spp., *Periplaneta* ssp., and *Schistocerca* spp.; from the order *Isoptera*, for spp; from the order *Psocoptera*, for spp.; from the order *Anoplura*, for example *jfaematopinus* spp., *Linognathus* spp., *Pediculus* spp., *Pemphigus* spp. and *Phylloxera* spp.; from the order *Mallophaga*, for example *Trichodectes* spp.; from the order *Thysanoptera*, for spp., *Hercinothrips* spp., *Taeniothrips* spp., *Thrips palmi, Thrips tabaci* and *Scirtothrips aurantii*; from the order *Heteroptera*, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp., *Triatoma* spp., *Miridae* family spp. such as *Lygus hesperus* and *Lygus lineoloris, LygaeidaQ* family spp. such as *Blissus leucopterus*, and *Pentatomidae* family spp.; from the order *Homoptera*, for example, *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lacanium comi, Lepidosaphes* spp., *Macrosiphus* spp., *Myzus* spp., *Nehotettix* spp., *Nilaparvata* spp., *Paratoria* spp., *Pemphigus* spp., *Planococcus* spp., *Pseudaulacaspis* spp., *Pseudococcus* spp., *Psylla* ssp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*; from the order *Hymenoptera*, for example, *Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp, *Solenopsis* spp. and *Vespa* ssp.; from the order *Diptera*, for example, *Aedes* spp., *Anopheles* spp., *Antherigona soccata, Bibio hortulanus, CalHphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomysa* spp., *Lucilia* spp., *Melanagromyza* spp., *Musca* ssp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp., from the order *Siphonaptera*, for example, *Ceratophyllus* spp. and *Xenopsylla cheopis* and from the order *Thysanura*, for example *Lepisma saccharin.*

In other embodiments, a composition comprising a non-live Csp_P preparation can be administered to an insect including, but not limited to, those with piercing-sucking mouthparts, as found in Hemiptera and some *Hymenoptera* and *Diptera* such as mosquitoes, bees, wasps, lice, fleas and ants, as well as members of the Arachnidae such as ticks and mites; order, class or family of Acarina (ticks and mites) e.g., representatives of the families Argasidae, Dermanyssidae, Ixodidae, Psoroptidae or Sarcoptidae and representatives of the species *Amblyomma* spp., *Anocentor* spp., *Argas* spp., *Boophilus* spp., *Cheyletiella* spp., *Chorioptes* spp., *Demodex* spp., *Dermacentor* spp., *Dermanyssus* spp., *Haemophysalis* spp., *Hyalomma* spp., *Ixodes* spp., *Lynxacarus* spp., *Mesostigmata* spp., *Notoedres* spp., *Ornithodoros* spp., *Ornithonyssus* spp., *Otobius* spp., *otodectes* spp., *Pneumonyssus* spp., *Psoroptes* spp., *Rhipicephalus* spp., *Sarcoptes* spp., or *Trombicula* spp.; *Anoplura* (sucking and biting lice) e.g., representatives of the species *Bovicola* spp., *Haematopinus* spp., *Linognathus* spp., *Menopon* spp., *Pediculus* spp., *Pemphigus* spp., *Phylloxera* spp., or *Solenopotes* spp.; *Diptera* (*flies*) e.g., representatives of the species *Aedes* spp., *Anopheles* spp., *Calliphora* spp., *Chrysomyia* spp., *Chrysops* spp., *Cochliomyia* spp., *Cw/ex* spp., *Cuucoides* spp., *Cuterebra* spp., *Dermatobia* spp., *Gastrophilus* spp., *Glossina* spp., *Haematobia* spp., *Haematopota* spp., *Hippobosca* spp., *Hypoderma* spp., *Lucilia* spp., *Lyperosia* spp., *Melophagus* spp., *Oestrus* spp., *Phaenicia* spp., *Phlebotomus* spp., *Phormia* spp., *Sarcophaga* spp., *Simulium* spp., *Stomoxys* spp., *Tabanus* spp., *Tannia* spp. or *Zzpu/alpha* spp.; *Mallophaga* (biting lice) e.g., representatives of the species *Damalina* spp., *Felicola* spp., *Heterodoxus* spp. or *Trichodectes* spp.; or *Siphonaptera*(wingless insects) e.g., representatives of the species *Ceratophyllus* spp., *Xenopsylla* spp; Cimicidae (true bugs) e.g., representatives of the species *Cimex* spp., *Tritominae* spp., *Rhodinius* spp., or *Triatoma* spp.

Embodiments of the present invention can be used to control parasites. As used herein, the term "parasite" includes parasites, such as but not limited to, protozoa, including intestinal protozoa, tissue protozoa, and blood protozoa. Examples of intestinal protozoa include, but are not limited to: *Entamoeba hystolytica, Giardia lamblia, Cryptosporidium muris*, and *Cryptosporidium parvum.* Examples of tissue protozoa include, but are not limited to: *Trypanosomatida gambiense, Trypanosomatida rhodesiense, Trypanosomatida crusi, Leishmania mexicana, Leishmania braziliensis, Leishmania tropica, Leishmania donovani, Toxoplasma gondii*, and *Trichomonas vaginalis.* Examples of blood protozoa include, but are not limited to *Plasmodium vivax, Plasmodium ovale, Plasmodium malariae*, and *Plasmodium falciparum. Histomonas meleagridis* is yet another example of a protozoan parasite.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: A non-live preparation of *Chromobacterium* sp. Panama (Csp_P) is a highly effective larval mosquito biopesticide. *Chromobacterium* species Panama (Csp_P) (Class: Betaproteobacteria, Family: Neisseriaceae) is a soil bacterium first isolated from *Ae. aegypti* midguts (27), which has a number of unique and useful properties for controlling mosquito-transmitted disease and mosquito populations. When *Anopheles gambiae* mosquitoes are fed on low doses of Csp_P they display reduced susceptibility to infection with the human malarial parasite *Plasmodium falciparum*: (27), as Csp_P produces a depsipeptide called romidepsin, which kills the parasite (28). Similarly, Csp_P infection in *Ae. aegypti* reduces susceptibility to dengue virus (27), through production of an aminopeptidase that promotes degradation of the viral envelope protein (29). Critically, higher doses of Csp_P have potent adulticidal activity against many mosquito species when provided in sucrose, and are also a very effective larvicide of *Ae. aegypti* and *An. gambiae* (27, 30).

Given these properties, Csp_P has great potential as an insecticide. However, to overcome potential regulatory, ecological, and epidemiological concerns about using an insecticide containing live bacteria, the present inventors sought to develop a Csp_P preparation that contained no live bacteria, which was easily prepared, and had a long shelf life, while retaining insecticidal activity against a range of important mosquito vectors in the laboratory and the field.

Materials and Methods

Mosquito lines. Multiple mosquito lines were used in the experiments described in this paper. The majority of the laboratory experiments were performed using the *Aedes aegypti* Rockefeller strain. The pyrethroid-resistant *Ae. aegypti* line (BEI resources—NR-48830) was purchased from BEI resources (Manassas, VA, USA). Experiments involving this line were performed using $F_{15}$ generation mosquitoes, one generation post-insecticidal treatment. Additional laboratory experiments were performed using the *Culex quinquefasciatus* JHB strain (originally isolated in Johannesburg, South Africa, BEI resources—NR-43025), and the *Anopheles gambiae* Keele strain, obtained from the Johns Hopkins University Malaria Research Institute Insectary. Laboratory mosquitoes were hatched in DI water mixed with the present inventors' laboratory's *Aedes* diet (1 part tropical fish flakes (Ken's Fish): 1 part rabbit chow (Nature's Promise): 2 parts liver powder (Now Foods)). At 2 days post-hatching, L2 stage larvae were thinned to a density of 250 per 1.5 L DI water, and then maintained on dry cat food pellets until the start of experiments. All laboratory mosquito strains were maintained in a climate-controlled insectary (temperature –27° C.±1° C., RH—80%±10%), with a 14:10 hour day-night cycle.

Experiments in the semi-field facility at Gurabo, Puerto Rico, USA, involved *Ae. aegypti* Patillas strain, and *Ae. mediovitattus*, both derived from previously described CDC San Juan mosquito colonies (45, 46). These colonies were maintained on 10% sucrose, and were kept in an insectary facility at 25-27° C., RH approximately 75%, and a 12-hour light-dark cycle. Eggs from both colonies were hatched in tap water and maintained on rabbit food. At 3 days post-hatching, larvae were transferred to the semi-field facility for experiments. Field-derived *Aedes* and *Culex* mosquitoes were also used in experiments conducted at the present inventors' semi-field facility. Eggs from 11 mosquito populations were collected from different neighborhoods around Puerto Rico (Bayamon, Catano, Guayanilla, Gurabo, Humacao, Juncos, Loiza, Ponce, Toa Alta, Trujillo Alto, and Yauco). At least 3 oviposition cups containing water or hay infusion and paper as an oviposition medium were left at each site. Cups were left out for approximately 7 days, and then collected. Egg papers were returned to the CDC, dried, hatched, and reared on rabbit food until adulthood. Only *Aedes aegypti* mosquitoes from these collections were used in subsequent experiments. In another set of experiments, larvae and water were collected from breeding sites that were discovered during surveys of different neighborhoods in Eastern Puerto Rico. These mosquitoes were transferred directly to the semi-field facility for experiments. Field collected mosquitoes were identified to the genus and/or species level, where possible.

Larvicidal pellet formulation and laboratory experimental design For laboratory experiments, groups of 30 L3 larvae were moved to mosquito breeders (h—19.5 cm, d –11 cm, Bioquip cat: 1425) containing 300 ml of DI water, at three days post-hatching. Three replicate breeders were set up for each treatment. Breeders were treated with either a negative control pellet, live bacterial control pellet, or a pellet containing non-live Csp_P powder, see below. The control pellets contained 100 mg of fishmeal (Dirty Gardener) as an attractant, 500 μL of LB broth (Lennox, Sigma-Aldrich cat: L3022), and 500 μL of 20% gelatin solution (Sigma-Aldrich cat: 53028) as a stabilizing agent. For control pellets, this formulation provided sufficient nutrients for 30 larvae to pupate and eclose. In place of LB broth, the live bacterial control pellets contained 500 μL of Csp_P grown in LB broth for 16 hours on a shaker at 30° C., at a speed of 200 rpm. The non-live Csp_P pellets had the same composition as the negative control pellet, but also contained 100 mg of non-live Csp_P powder. After preparation, pellets were allowed to set at 4° C. for 1-2 hours and then added to a mosquito breeder. Mosquito survival was then monitored daily for 12 days, with adults provided cotton soaked in 10% sucrose, which was refreshed daily. Each experiment was repeated 3 times and involved 3 replicate cages per treatment.

Non-live Csp_P powder preparation. Five different air-dried, non-live Csp_P powders were evaluated for their ability to kill Rockefeller larvae. Three preparations (non-live_1, non-live 2, and non-live_3) were derived from Csp_P cultures on sterile 400 $cm^2$ petri dishes (Coning), each containing approximately 200 ml of LB agar (Sigma-Aldrich cat: L2897). Each plate was inoculated with 2 ml of live Csp_P stock (1:1 in 50% glycerol solution, stored at –80° C.), and then left to grow for 48 hours in an incubator at 30° C. For the non-live_2 preparation, bacterial cells were removed from the agar using a cell scraper (Sarstedt), and then transferred to a petri dish to dry. For the non-live_1 and non-live_3 preparations, 50 ml of LB broth was added to the surface of each plate. Plates were then incubated for a further 120 hours at room temperature. At that point, the liquid on the surface of each plate was decanted and dried down to become the non-live_3 preparation. Plates were left to dry for a further 24 hours, and then the bacterial cells on the surface were removed with a scraper and dried to become the non-live_1 preparation. The final two preparations, non-live_4 and non-live_5, were cultured in sterile 6-well plates (costar cat: 3506). Briefly, each well containing 5 ml of LB broth was inoculated with 5 μL of live Csp_P stock, and the plates were sealed in parafilm and then left to grow for 72 hours at room temperature. For the non-live_5 preparation, biofilm was collected from the surface of each well, mixed with sterile 1×PBS and then dried. The non-live_4 preparation contained the remaining material from the 6-well plate after the surface biofilm was removed. This too was air dried at room temperature. All preparations were dried under continuous air flow in a fume hood. Four preparations, (non-live 2 through 5) were completely dried over the course of 2-3 days. The final preparation (non-live 1) required a longer period to dry completely due to a greater volume of material. After drying, each preparation was manually crushed to a fine powder using a mortar and pestle. Pellets containing the different powders were prepared, as described above, and then fed to Rockefeller larvae to assess their larvicidal activity.

To validate that each of these powders contained no live Csp_P cells, the present inventors collected 100 mg of each preparation immediately after the air-dried bacteria had been crushed to a powder. The powders were moved to sterile 1.5 ml tubes and then mixed with 1 ml of sterile 1×PBS. Three dilutions were prepared for each powder ($10^0$, $10^2$ and $10^4$) through serial dilution in sterile 1×PBS, and 100 μL from each of these tubes was inoculated onto sterile LB agar plates (without antibiotics), and spread using sterile glass beads. The plates were inverted and then placed in an incubator set to 30° C. for 48 hours, with these conditions being optimal for culturing live Csp_P. These experiments were performed three times, each from independent batches of air-dried powders.

The present inventors assayed for the presence of cyanide containing species in each of the 5 non-live powders using the Cyanide Test Kit, Model CYN-3 (Hach, 2010-02). Each preparation was cultured, air-dried and crushed to powder, as described above, and then used for testing within one week after the air drying process was finished. A total of 10 mg of each powder was dissolved in 10 ml of MilliQ water in a 15 ml tube. These tubes were then mixed by hand until the contents went into suspension. 5 ml from each tube was used in the Cyanide test, which was completed according to manufacturer's instructions (30).

Assaying non-live Csp_P activity. Unless specified below, all experiments utilized 100 mg of non-live Csp_P powder, prepared according to the non-live_1 Csp_P protocol, as described above. Pellets containing the biopesticide were prepared and then fed to Rockefeller larvae, pyrethroid-resistant *Ae. aegypti* ROCK larvae, *Cx. quinquefasciatus* larvae, and *An. gambiae* larvae, in order to assay whether the powder could kill multiple mosquito vector species, and mosquitoes that were resistant to commonly used insecticides. In further experiments, pellets containing different quantities of non-live_1 Csp_P powder (100 mg, 50 mg, 25 mg, 12.5 mg and 6.25 mg) were offered to ROCK larvae in order to evaluate the larvicidal properties of lower doses, and calculate the $LD_{50}$ of that preparation. To assess whether the larvicidal activity occurred as a result of culturing method, the present inventors cultured the mosquito-associated bacteria *Acinetobacter baylyi, Pseudomonas rhodesiae* and *Serratia marscecens* using the non-live_1 protocol, and fed these to Rockefeller larvae. These species were grown from frozen stocks that were already present in the present inventors' laboratory, stored at −80° C. in 50% glycerol and LB broth (47).

Accelerated shelf life testing. The EPA guidelines for product development indicate that accelerated shelf life tests be performed to assess stability of the active agents in a product (48). Under the suggested guidelines, a product treated at 54° C. for two weeks is comparable to one year spent at room temperature. Non-live_1 Csp_P powder was transferred to 50 ml plastic tubes (Falcon) and wrapped in one layer of aluminum foil, with this setup serving as a mock commercial packaging. The tubes of powder were then left at room temperature, 30° C., 37° C., 54° C., or 70° C. for two weeks in incubators. Due to incubator availability, the 70° C. treatment was performed independently, however, comparisons in those experiments were made using a separate batch of room temperature non-live_1 Csp_P powder that was prepared during the same period. Pellets were made from each preparation and fed to Rockefeller larvae.

Increasing pellet stability. To improve pellet stability, the present inventors developed a revised pellet formulation with 1.5% agar (Sigma-Aldrich A1296) substituting for gelatin as the stabilizing agent, and LB Broth excluded from the recipe. These agar pellets displayed increased integrity in water, remaining intact for weeks, as opposed to days for gelatin-based pellets. To assess the integrity of the revised formulation the present inventors performed two experiments. In these experiments, control pellets contained 100 mg of fishmeal as an attractant, and 1 ml of 1.5% agar, while non-live Csp_P pellets also contained 125 mg of non-live 1 Csp_P powder. Assay conditions and sample size were as described for gelatin pellet experiments. Each experiment was repeated three times, and these replicates contained two technical replicates of each pellet type/treatment. In the first experiment, the present inventors assessed the residual activity of agar pellets. One batch of agar pellets was prepared and immediately placed into individual mosquito breeders, each containing 300 ml of DI water. These breeders and pellets were left undisturbed for 14 days at room temperature. After this time, a further batch of pellets was prepared and added to mosquito breeders. *Ae. aegypti* larvae were then added to all breeders, and survival was monitored daily, as described above. Secondly, the present inventors assessed the activity of whole agar pellets after heat treatment. Control and non-live Csp_P agar pellets were prepared as described above. Pellets were sealed in plastic wrap to prevent moisture loss, and then left at room temperature, 37° C., or 54° C. for 7 days. Pellets were then fed to *Ae. aegypti* larvae and survival was monitored daily, as described above.

Semi-field trials with CDC colony and field-derived mosquitoes. For semi-field experiments, pellets were made, as above, at the semi-field site, except that LB broth and gelatin stocks were not prepared under sterile conditions. The dose of Csp_P powder in the pellets used in these experiments was increased to 200 mg, to account for high larval numbers in some breeding sites. Non-live Csp_P powder stocks used in these experiments were prepared at Johns Hopkins University and shipped to Puerto Rico. The present inventors first assessed the impact of the powder on *Ae. aegypti* Patillas and *Ae. mediovitattus* colony mosquitoes. Larvae were transported to the field cage at 3 days post-hatching, and then divided into small plastic cups containing 300 ml of tap water, 30 larvae to a cup, with four cups of each treatment used per experiment. Larval survival was then monitored daily for 6 days. Next, the present inventors assessed the efficacy of the non-live Csp_P powder on $G_1$ larvae from 11 *Ae. aegypti* populations collected around Puerto Rico. Eggs from each population were hatched and then taken to the field cage 2 days later. As $G_1$ larval numbers were low, a maximum of 15 per cup were used, with one cup per treatment, per population. In these experiments, survival was monitored every 1-3 days.

For experiments involving larvae and water collected from breeding sites in the field, larvae and water were transferred to sterile plastic cups using sterile pipettes, and then transported to the semi-field cage where experiments were conducted. The volume of water was measured using plastic measuring cups and divided evenly between two plastic containers. Larvae and pupae from each breeding site were divided into these containers. One cup was fed a negative control pellet, while the other was fed a pellet containing non-live Csp_P powder. Cups were then covered in mesh to prevent adults from escaping. In these experiments, adult eclosion was monitored every 1-3 days, by counting and then removing adults in each cup.

Statistical analysis. For all experiments, survival data were compared across replicate experiments using Cox Proportional Hazard Models within SPSS V17 (IBM). For field breeding site experiments, the proportion of mosquitoes that eclosed was compared between treatment and control groups using Fisher's exact test (Prism v6.0h, Graphpad), and Cox Proportional Hazard Models (SPSS V17, IBM). FIG.s were created using Prism v6.0h (Graphpad), and Microsoft PowerPoint for Mac (v 16.19).

TABLE 1

Larvicidal activity of different non-live Csp_P preparations.

| Treatment | N a | Average time to death (±s.e.m.) b $R_1$ | $R_2$ | $R_3$ | Overall | Exp. β c | % Survival d |
|---|---|---|---|---|---|---|---|
| Control | 270 | 5.91 ± 0.39 | 7.56 ± 0.71 | 7.00 ± 1.22 | 6.93 ± 0.44 | NA | 87.78 |
| Live | 260 | 1.90 ± 0.06 | 2.36 ± 0.07 | 2.72 ± 0.09 | 2.32 ± 0.05 | 99.17 | 0.00 |
| Non-live_1 | 253 | 2.52 ± 0.20 | 3.31 ± 0.17 | 2.55 ± 0.09 | 2.80 ± 0.10 | 50.11 | 0.79 |
| Non-live_2 | 254 | 3.97 ± 0.18 | 6.36 ± 0.34 | 5.43 ± 0.30 | 5.19 ± 0.17 | 31.17 | 4.72 |
| Non-live_3 | 262 | 3.98 ± 0.26 | 3.73 ± 0.23 | 3.56 ± 0.18 | 3.76 ± 0.13 | 30.44 | 0.38 |
| Non-live_4 | 247 | 3.73 ± 0.22 | 2.40 ± 0.19 | 3.88 ± 0.21 | 3.31 ± 0.13 | 33.00 | 0.81 |
| Non-live_5 | 255 | 3.09 ± 0.17 | 4.48 ± 0.30 | 1.81 ± 0.08 | 3.08 ± 0.13 | 44.38 | 0.39 |

a - Total larvae counted across three experiments.

b - Average time to death compiled across three replicate cages for replicate experiment 1-3 ($R_1$-$R_3$) ± standard error of mean.

c - Exp. β = Hazard ratio, calculated using Cox Regression.

d - Percentage of larvae surviving at 12 days post-exposure to pellet.

TABLE 2

Characteristics of the 11 breeding sites collected around Puerto Rico.

| Site | Site type | Collection date a | Collection location | Larvae/ pupae (N) | Mosquito genera |
|---|---|---|---|---|---|
| A | Tire | 14th Feb. 2018 | Caguas | 186 | Aedes/ Culex |
| B | Paint Bucket | 15th Mar. 2018 | Cataño | 20 | Aedes |
| C | Water meter | 15th Mar. 2018 | Cataño | 52 | Culex |
| D | Plastic cup | 22nd Mar. 2018 | Cataño | 28 | Aedes |
| E | Plastic bucket | 21st Aug. 2018 | Puerto Nuevo | 70 | Aedes/ Culex |
| F | Trash container | 22nd Aug. 2018 | Cupey | 78 | Aedes/ Culex |
| G | Paint bucket | 22nd Aug. 2018 | Cupey | 38 | Aedes |
| H | Metal pipe | 18th Sep. 2018 | Puerto Nuevo | 24 | Aedes |
| I | Metal bucket | 25th Oct. 2018 | Salinas | 112 | Aedes |
| J | Plastic container | 25th Oct. 2018 | Salinas | 38 | Aedes/ Culex |
| K | Waste water tank | 25th Oct. 2018 | Salinas | 38 | Culex |

a—breeding sites were translocated to the semi-field facility on this date and then treated with the non-live Csp_P biopesticide.

b—Total larvae and pupae observed in the breeding site water.

Results

Pellet design and attractants. In order to facilitate development of a non-live insecticide based on the bacterium *Chromobacterium* species Panama Csp_P, the present inventors first developed an attractive larvicidal bait, in the form of a pellet that could be used to deliver Csp_P to mosquito larvae. This bait needed to induce feeding amongst larvae, and also maintain structural integrity within an aqueous environment so that mosquitoes could feed on it.

In a series of preliminary experiments (Supplementary File 1), the present inventors assessed the attractiveness of fishmeal (Dirty Gardener) and ground tropical fish flakes (Tetramin) when provided to *Ae. aegypti* larvae in pellets made with 20% gelatin as a stabilizing agent. In experiments testing the attractiveness of individual baits, the present inventors observed that 97.5% of larvae responded to fishmeal pellets within 30 mins of exposure. In contrast, only 71.7% of larvae responded to pellets containing tropical flakes, over the same time period. When both fishmeal- and tropical flakes-containing baits were offered to larvae over 30 mins in bait choice assays, an average of 80% responded to fishmeal-containing baits, while 13.33% chose tropical flakes-containing baits, and 6.67% did not respond. Consequently, the present inventors decided to use fishmeal baits in all subsequent assays.

The present inventors then incorporated live Csp_P into pellets and fed it to *Ae. aegypti* Rockefeller (ROCK) larvae in order to examine the efficacy of pellets as a larvicide delivery tool. Pellets containing live Csp_P killed all larvae in a 300 ml container within 6 days, with an average time to death post-exposure of 2.09 (±0.05) days, and an expected hazard ratio of 83.99 in comparison to pellets without bacteria (Cox Regression: W=180.64, df=1, Exp β=83.99, P<0.0001) (FIG. S1).

Development and assessment of non-live Csp_P preparations. The present inventors developed five different culturing methods (non-live_1 through non-live 5) to produce large quantities of non-live, air-dried, powdered Csp_P (see Experimental Procedures section for details on the culturing processes). Immediately after air-drying, each of the non-live powders was mixed with 100 μL of 1×PBS, and 3 different dilutions of these mixtures were inoculated onto LB agar, and incubated at 30° C. for two days. Across three experimental replicates, the present inventors did not observe any bacterial colonies for any of the 5 preparations at any dilution.

The present inventors compared the larvicidal activity of these preparations across three replicate experiments wherein 100 mg of each preparation was incorporated into a gelatin/fishmeal pellet, and then offered to *Ae. aegypti* ROCK larvae. This dose was utilized in all subsequent assays, unless specified. The present inventors again observed that all 5 powders killed larvae, however they were not equally effective (Table 1). Based on the results of these experiments the present inventors selected the non-live_1 preparation (FIG. 1) for further testing as it produced the shortest average time to death for exposed larvae (2.80±0.10 days), and also produced the highest hazard ratio (Cox Regression: W=145.83, df=1, Exp β=50.11, P<0.0001) in comparison to the control treatment. This decision was also based on the consistency of the larvicidal activity that was observed for non-live_1 powder across three replicates, and the high yield of that powder compared to the other four. In the experiments described below, the present inventors refer to the non-live_1 powder as non-live Csp_P.

Non-live Csp_P powder does not contain cyanide. The present inventors tested each of the five powders for the presence of cyanide using the Cyanide Test Kit, Model CYN-3 (Hach, 2010-02), as cyanide toxicity is considered the likely means through which live Csp_P kill larvae when in suspension (30). The present inventors observed that the pH of each powder, resuspended in DI water, was between 5-6. At the completion of the test, the present inventors did not observe a change in color for any sample, indicating that there was no evidence of the presence of cyanide species in any of the non-live Csp_P powders.

Non-live Csp_P powder has a larvicidal effect against different mosquito species. The present inventors examined the larvicidal efficacy of non-live Csp_P powder against *Ae. aegypti* Rockefeller (FIG. 2A), pyrethroid-resistant *Ae. aegypti* (FIG. 2B), *An. gambiae* Keele (FIG. 2C), and *Culex quinquefasciatus* (FIG. 2D). In each of these assays, gelatin/fishmeal pellets containing 100 mg of non-live Csp_P powder were fed to L2 larvae, and mortality rates compared against groups of larvae fed pellets containing either live Csp_P or no-bacteria controls. Rockefeller larvae challenged with live bacteria had an average time to death of 2.48±0.05 days (Cox Regression: W=275.42, df=1, Exp β=67.08, P<0.0001), while those challenged with non-live Csp_P powder had an average time to death of 3.13±0.08 days (Cox Regression: W=233.35, df=1, Exp β=42.68, P<0.0001). Pyrethroid-resistant *Ae. aegypti* challenged with live Csp_P lived 2.52±0.05 days on average post-exposure (Cox Regression: W=202.04, df=1, Exp β=295.64, P<0.0001), while larvae from the same line fed on non-live Csp_P lived 3.40±0.13 days on average (Cox Regression: W=177.81, df=1, Exp β=183.94, P<0.0001). *An. gambiae* larvae fed live Csp_P had an average time to death of 1.10±0.02 days (Cox Regression: W=162.63, df=1, Exp β=272.37, P<0.0001), while those challenged with non-live Csp_P survived for 2.25±0.09 days post-treatment, on average (Cox Regression: W=122.00, df=1, Exp β=113.30, P<0.0001). Finally, *Cx. quinquefasciatus* larvae challenged with live Csp_P lived 1.40±0.03 (Cox Regression: W=199.99, df=1, Exp β=63.02, P<0.0001) days on average, compared to 1.68±0.05 days on average for those challenged with non-live Csp_P (Cox Regression: W=187.76, df=1, Exp β=51.17, P<0.0001). During the course of these experiments, no larvae of any species that were exposed to the Csp_P biopesticide pupated. In contrast, the present inventors observed that pupation amongst larvae fed on control bait occurred from days 3 through 7 after exposure to the bait.

Larvicidal dose-response of non-live Csp_P powder. To assess the efficacy of non-live Csp_P at different doses, the present inventors performed three experiments where the present inventors provided larvae with gelatin/fishmeal pellets containing 100 mg, 50 mg, 25 mg, 12.5 mg or 6.25 mg of non-live Csp_P powder (FIG. 3A). The present inventors observed that larvae treated with all five doses had significantly greater mortality than the control treatment (Cox Regression: P<0.0001 for all comparisons). One hundred percent mortality was observed with the 100 mg treatment, while greater than 99% mortality was observed in the 50 mg treatment at 12 days post-exposure. No pupation was observed in either of these conditions, while control larvae pupated 4-6 days after the start of the experiment. A small number of adults were observed in the 12.5 mg and 6.25 mg treatments, with an average mortality of 70.34% and 56.36% observed in those treatments, respectively, at 12 days post-treatment. Based on the results of these experiments, the present inventors calculated the $LD_{50}$ of non-live Csp_P in the present inventors' experimental setup (30 larvae in 300 ml of water) as 3.40 mg of powder. This equated to an $LD_{50}$ of 11.35 mg of non-live Csp_P powder per liter of water.

Figure 3B:
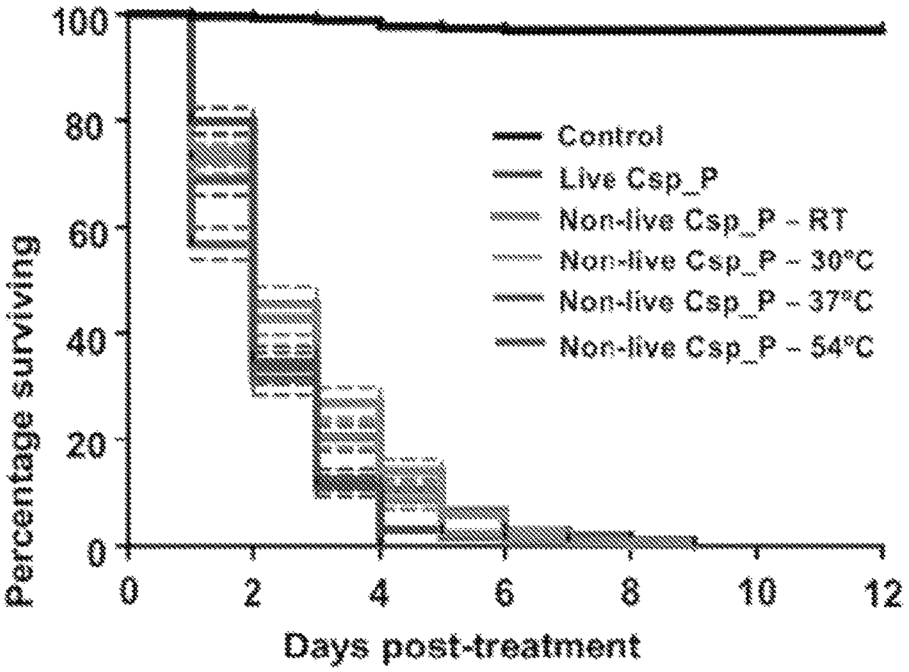
Figure 3C:
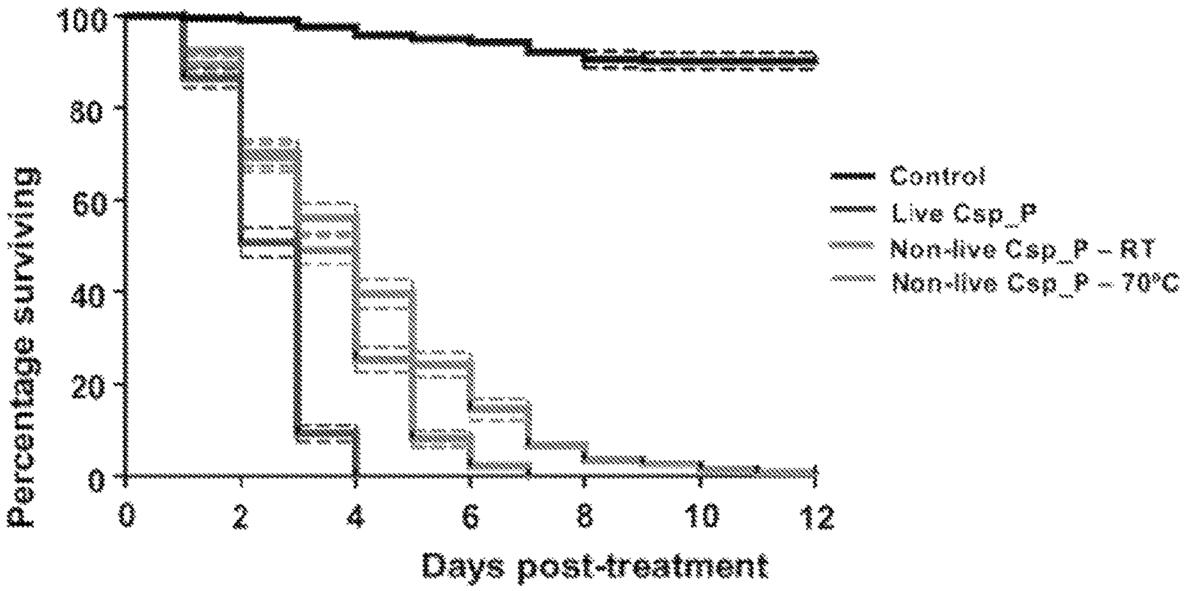

Non-live Csp_P powder is highly heat stable. In order to assess the potential shelf life of non-live Csp_P powder, the present inventors performed accelerated shelf life tests, where the present inventors treated the powder at 30° C., 37° C., 54° C. (FIG. 3B), or 70° C. (FIG. 3C) for two weeks, and then assessed the impact on larvicidal activity by comparing these treatments against powder left at room temperature for two weeks, with powder from each treatment independently incorporated into gelatin/fishmeal pellets. The present inventors observed that the mortality of all of non-live Csp_P treatments was significantly greater than that of the control treatment (Cox Regression: room temperature—W=178.65, df=1, Exp β=140.13, P<0.0001; 30° C.—W=170.88, df=1, Exp β=126.57, P<0.0001; 37° C.—W=185.77, df=1, Exp β=152.63, P<0.0001; 54° C.—W=189.91, df=1, Exp β=164.63, P<0.0001). Critically, the present inventors observed no difference in activity between the heat-treated powders and the powder left at room temperature (Cox Regression: P>0.05).

Experiments with non-live Csp_P powder treated at 70° C. were run independently due to incubator availability. In these experiments, the present inventors observed that both the room temperature and 70° C. treatments had significantly greater mortality than the control treatment (Cox Regression: Room Temperature—W=285.91, df=1, Exp β=44.74, P<0.0001; 70° C.—W=254.31, df=1, Exp β=32.41, P<0.0001). The present inventors also observed a slight loss of larvicidal activity with the 70° C. treatment, although 99.2% of the larvae that were exposed died within 12 days. The average mortality for the 70° C. treatment was 4.03±0.14 days, compared to 3.48±0.09 for the room temperature treatment (Cox Regression: W=12.83, df=1, Exp β=0.72, P<0.0001).

While conducting the above experiments, the present inventors noticed that the present inventors' gelatin-based pellets dissolved within 2-3 days after being added to water. Consequently, the present inventors developed an agar-based pellet formulation that maintained structural integrity when left submerged in water for 14 days (FIG. S2A). Interestingly, when *Ae. aegypti* larvae were added to containers where the water had been pre-exposed to non-live Csp_P agar pellets for 14 days, the present inventors observed significantly higher mortality than for larvae treated with freshly-made non-live Csp_P agar pellets (Cox Regression: W=31.031, df=1, Exp β=2.07, P<0.0001). However, there was no significant effect on mortality due to pre-exposure for non-bacterial control pellets (Cox Regression: W=0.59, df=1, Exp β=0.67, P=0.442). The present inventors then exposed control and non-live Csp_P agar pellets to different temperatures (room temperature, 37° C. or 54° C.) for 7 days in order to see if temperature treatment had an impact on the larvicidal activity of agar pellets (FIG. S2B). The present inventors observed no significant influence of temperature on the larvicidal activity of control pellets (Cox Regression: W=0.15, df=2, P=0.929) or non-live Csp_P pellets (Cox Regression: W=2.80, df=2, P=0.246).

Figure 3D:
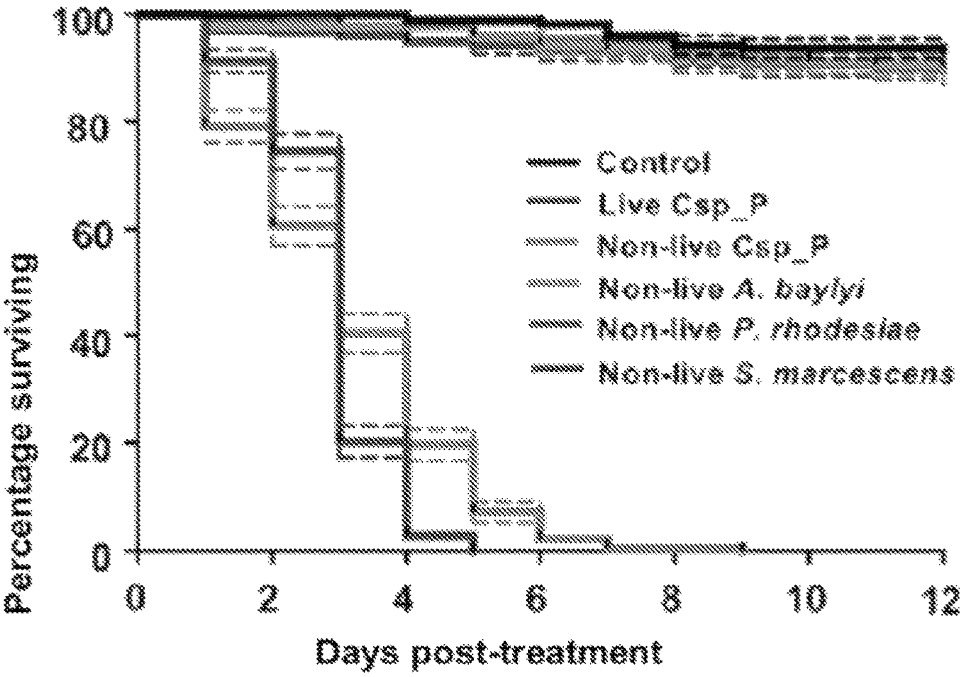

Effect with other bacteria. The present inventors performed the same non-live Csp_P culturing and drying procedure described above, with three other mosquito-associated bacteria: *Acinetobacter* baylyi, *Serratia marcescens*, and *Pseudomonas rhodesiae*, in order to demonstrate that the larvicidal effect the present inventors observed after feeding on non-live Csp_P powder was not due to the culturing and/or drying processes, and was not ubiquitous across all bacteria fed to mosquito larvae in this manner (FIG. 3D). Across three experiments, the present inventors observed that only non-live Csp_P powder had significantly different mortality to the no bacteria control treatment (Cox Regression: W=180.34, df=1, Exp β=75.20, P<0.0001). Hazard ratios associated with feeding powders derived from *A. baylyi, S. marcescens*, and *P. rhodesiae* cultures were 1.46, 1.56, and 1.51, respectively, compared to the control treatment, indicating that there was no significant larvicidal effect associated with powders derived from these three bacteria.

Figure 4A:
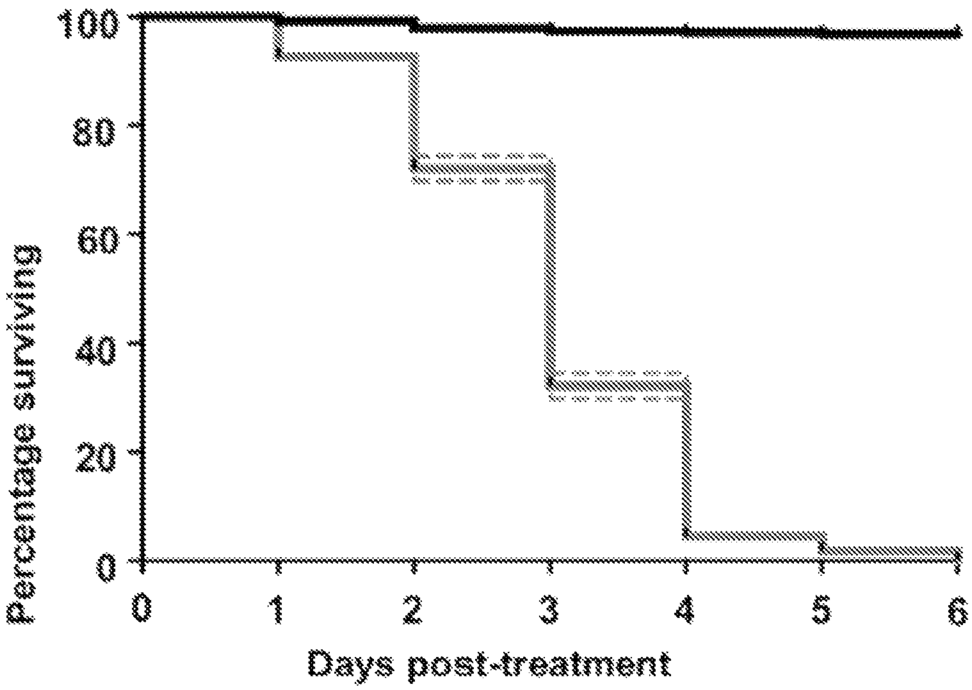
FIG. 4A-4B. Non-live Csp_P powder effectively kills mosquito larvae under semi-field conditions. *Ae. aegypti* Patillas (FIG. 4A) and *Ae. mediovitattus* (FIG. 4B) larvae were reared under insectary conditions for three days, and then transferred to a semi-field facility at Gurabo, Puerto Rico. Larvae were treated with a no bacteria control pellet (black lines), or a pellet containing 200 mg of non-live Csp_P (blue lines), and then left under ambient environmental conditions. The present inventors observed significant mortality induced by Non-live Csp_P for larvae from both species (Cox Regression: P<0.0001) indicating that the larvicide performed effectively under semi-field conditions. Larvae were reared in groups of 30 in 300 ml of tap water. Lines depict the percentage of larvae surviving at each day post-treatment (±s.e.m.).
Figure 4B:
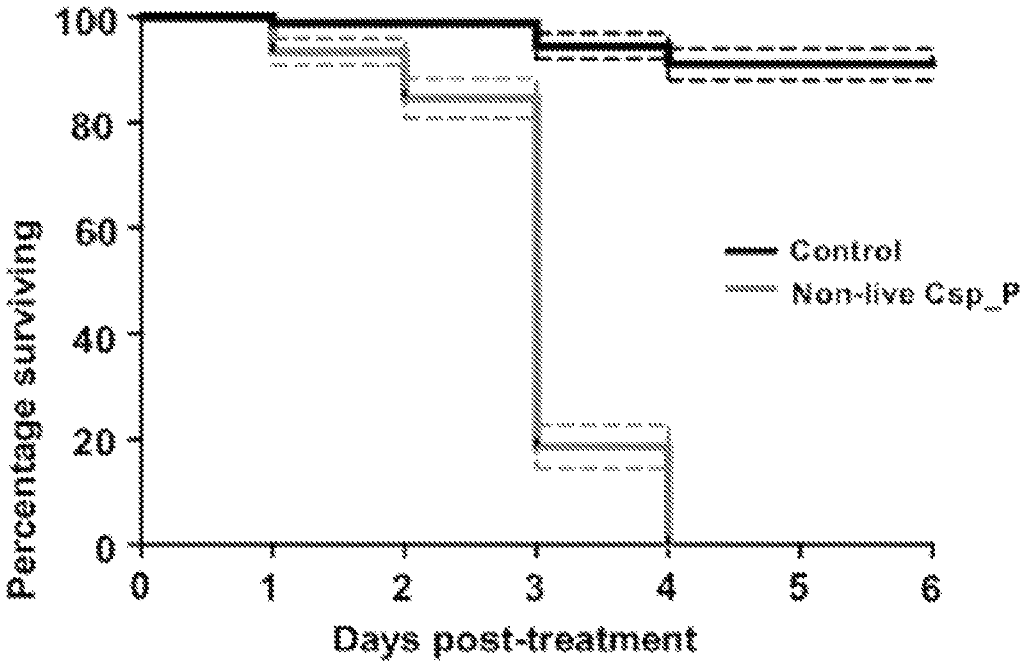

Non-live Csp_P powder exert larvicidal activity under field conditions. The present inventors assessed the efficacy of the non-live Csp_P powder in a semi-field setting. These experiments were conducted at a semi-field facility in Gurabo, Puerto Rico. In the first of three trials, the present inventors tested the non-live Csp_P powder against larvae from the CDC San Juan *Ae. aegypti* colony (Patillas strain) (FIG. 4A). Larvae were moved to small cups containing 300 ml of tap water, treated with gelatin/fishmeal pellets containing 200 mg of non-live Csp_P powder, and the cups left in the semi-field cage, exposed to ambient environmental conditions. The present inventors observed that mortality was significantly increased in the treated cups compared to the control cups (Cox Regression: W=207.85, df=1, Exp β=87.59, P<0.0001), with 100% mortality within 6 days, compared to 2.93% mortality in the control treatment cups over that time. Average time to death for insecticide-treated larvae was 3.03±0.05 days. The present inventors then performed similar experiments with mosquitoes from the CDC *Aedes* mediovitattus colony (FIG. 4B), and observed that all larvae died within four days of treatment, with an average time to death of 2.97±0.08 days (Cox Regression: W=64.39, df=1, Exp β=20.64, P<0.0001).

Figures 5A, 5B, 5C, 5D, 5E, 5F, 5G, 5H, 5I, 5J, 5K:
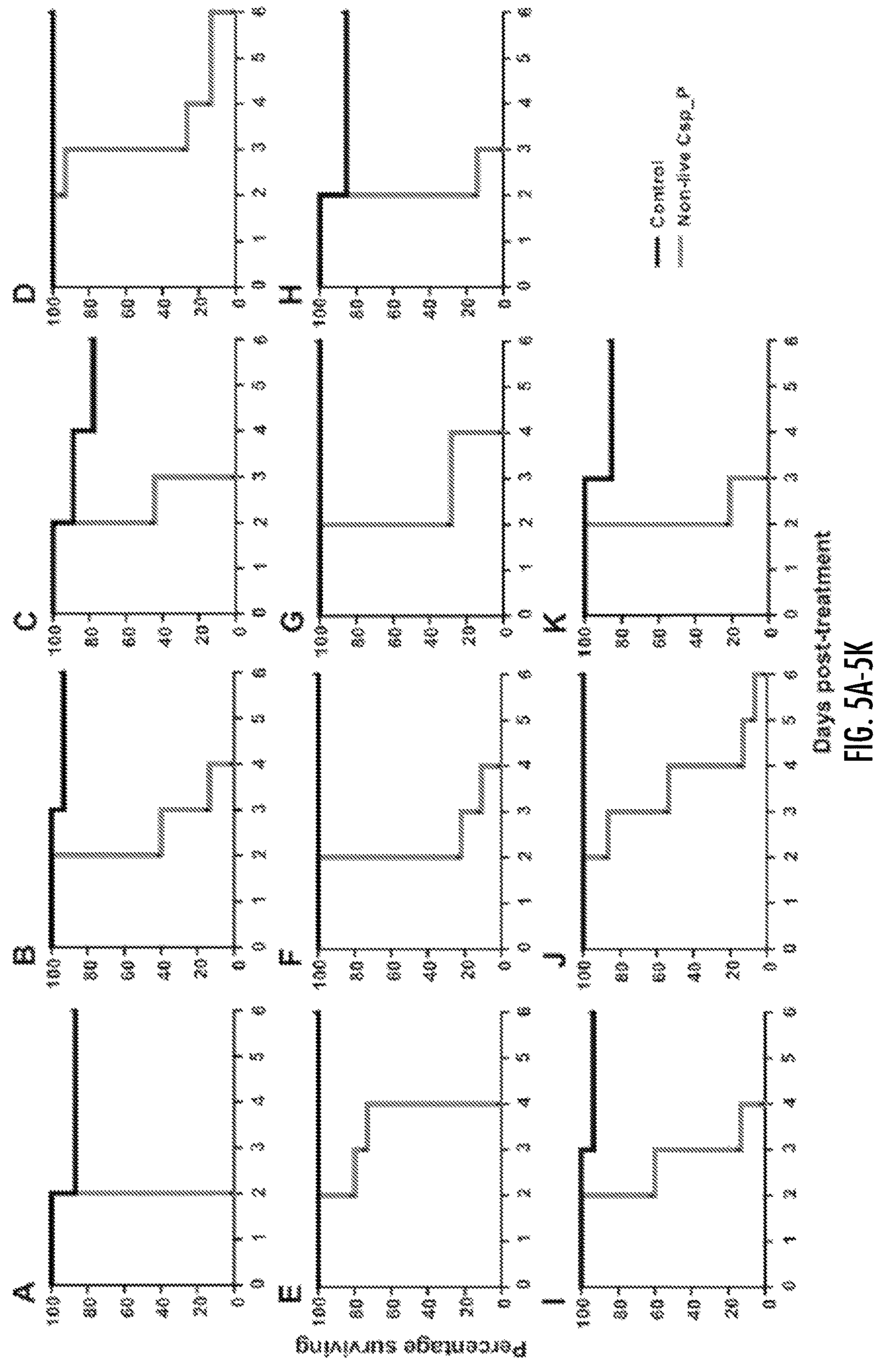
FIG. 5A-5K. Non-live Csp_P powder effectively kills larvae from different *Ae. aegypti* $G_1$ field-derived populations under semi-field conditions. *Ae. aegypti* eggs were collected from 11 different sites around Puerto Rico using oviposition cups. Egg papers were hatched under insectary conditions, typed for mosquito species, and then transferred to the semi-field cage. Larvae from each population were divided in two, with half fed a control pellet (black lines), and half fed a pellet containing 200 mg of non-live Csp_P (blue lines), and then left under ambient environmental conditions. 100% mortality for all Csp_P-treated larvae was achieved in 2-6 days. Each panel depicts a different *Ae. aegypti* population: Bayamon (FIG. 5A), Catano (FIG. 5B), Guayanilla (FIG. 5C), Gurabo (FIG. 5D), Humacao (FIG. 5E), Juncos (FIG. 5F), Loiza (FIG. 5G), Ponce (FIG. 5H), Toa Alta (FIG. 5I), Trujillo Alto (FIG. 5J), Yauco (FIG. 5K). Larvae were reared in groups of 7-15 in 300 ml of tap water. Lines depict the percentage of larvae surviving at each day post-treatment.

Next, the present inventors collected *Ae. aegypti* eggs using oviposition cups deployed at eleven different sites across Puerto Rico. These egg papers were returned to the laboratory, and hatched in tap water. $G_1$ larvae from these populations were transferred to the semi-field cage. The larvae from each population were split into two cups, half were fed a control pellet, and half were fed a non-live Csp_P pellet. Survival was monitored in these cups for 6 days, at which point 100% of the insecticide-treated larvae had died (FIG. 5). Over this time period 9/143 (6.29%) of the control larvae had died (Cox Regression: W=112.61, df=1, Exp β=49.17, P<0.0001). For Csp_P-exposed mosquitoes across all 11 populations, there was an average time to death of 2.73±0.08 days.

Figures 6A, 6B, 6C, 6D, 6E, 6F, 6G, 6H, 6I, 6J, 6K:
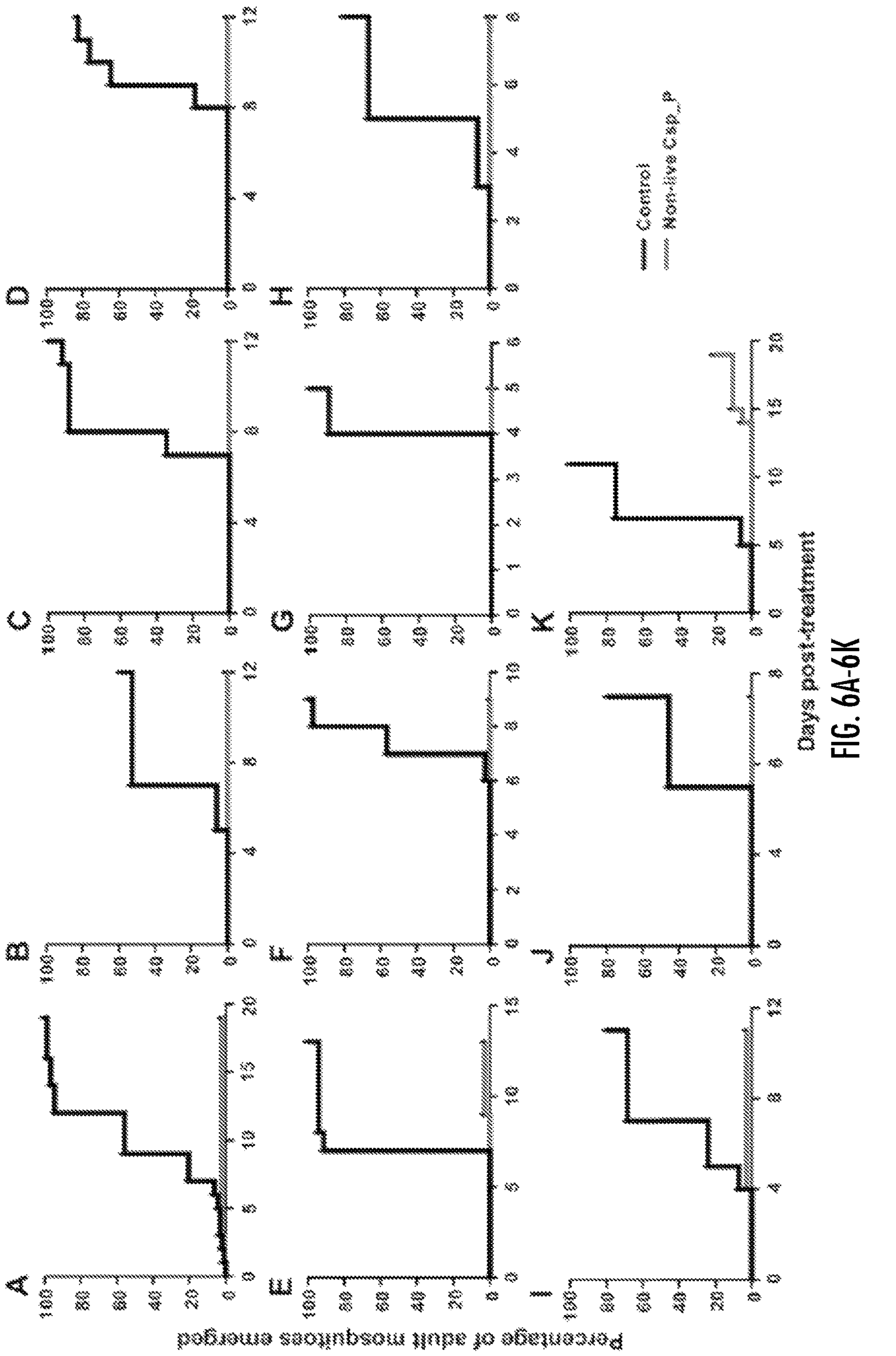
FIG. 6A-6K. Non-live Csp_P powder effectively prevents adult mosquito emergence from translocated breeding sites under semi-field conditions. Mosquito breeding sites were located at various sites around Eastern Puerto Rico. The water and any larvae and pupae were removed from the breeding site and moved to the semi-field cage in sterile containers. Larvae and pupae were counted, and along with the water and any detritus, divided evenly between a control treatment (black lines) and a non-live Csp_P treatment (blue lines). Adult emergence was monitored as it was too difficult to locate dead $L_1$ and $L_2$ larvae in the opaque breeding site water. Across eleven different breeding sites, the present inventors observed that 342/374 adults emerged from the control treatment, compared to 9/374 from the non-live Csp_P treatment (Fisher's exact test: P<0.0001). Breeding sites contained either *Ae. aegypti* larvae (N=5), *Cx. quinquefasciatus* larvae (N=2), or a mix of both (N=4). Breeding sites were collected from the following receptacles: tire (FIG. 6A), paint pail (FIG. 6B), water meter (FIG. 6C), plastic cup (FIG. 6D), bucket (FIG. 6E), container (FIG. 6F), bucket (FIG. 6G), pipe (FIG. 6H), bucket (FIG. 6I), container (FIG. 6J), waste water tank (FIG. 6K). Lines depict the percentage of adults that had emerged from the breeding site water at different intervals post-treatment.
Figure 7:
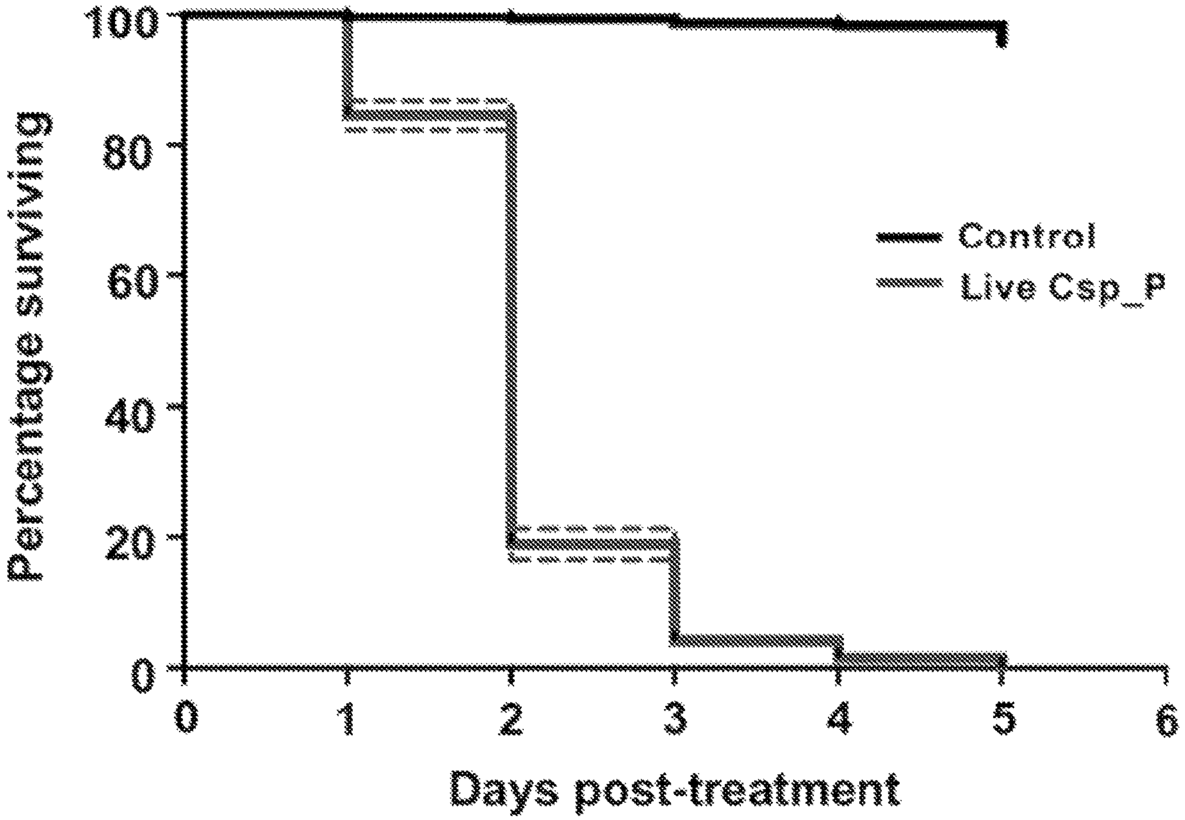
FIG. 7. Live *Chromobacterium* Csp_P effectively kills *Ae. aegypti* ROCK larvae when provided in a pellet. Groups of 30 L2 larvae were provided either a control (black line) or live Csp_P (red line) pellet in 300 ml of deionized water. Pellets contained fishmeal as an attractant, and 20% gelatin as a stabilizing agent. Pellets containing live Csp_P induced a significantly higher rate of mortality than no bacteria control pellets (Cox Regression: P<0.0001). Lines depict the percentage of larvae surviving at each day post-treatment (±s.e.m.) for four experimental replicates, with each containing three cages per treatment.
Figure 8A:
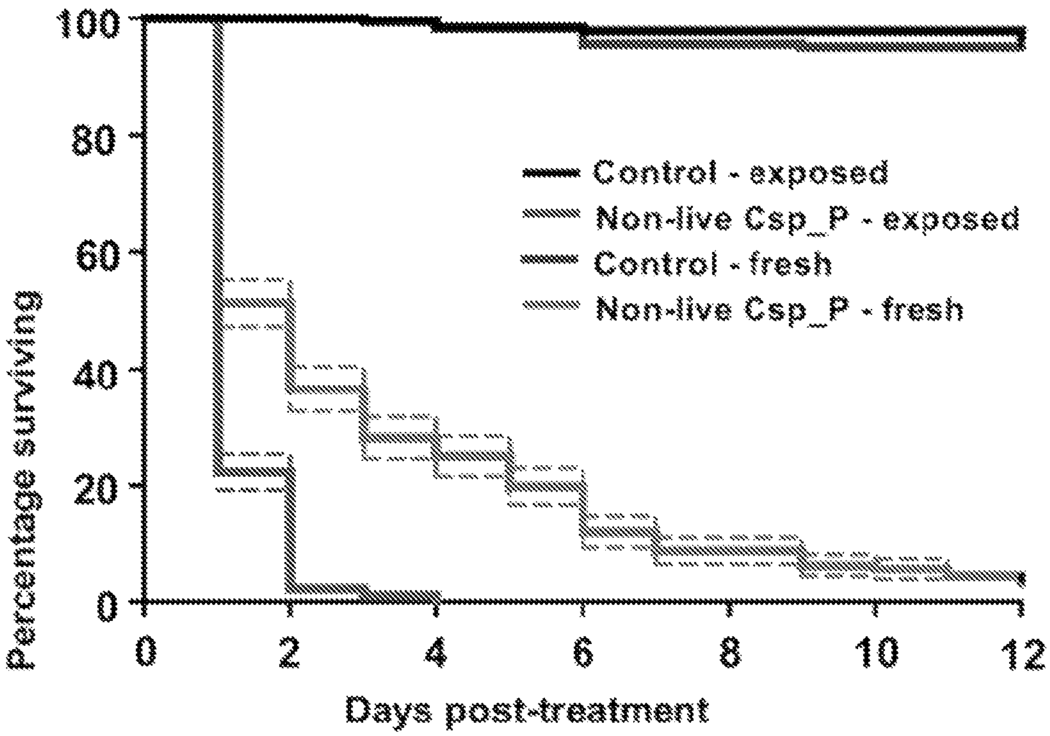
FIG. 8A-8B. Non-live Csp_P agar pellets have lengthy residual activity, and are heat stable. The present inventors developed a revised non-live Csp_P pellet formulation, substituting 1.5% agar for 20% gelatin to improve pellet stability in water. The present inventors examined the efficacy of these pellets against *Ae. aegypti* ROCK larvae where pellets were either freshly prepared and fed to larvae (fresh), or left sitting in a mosquito breeder and 300 ml of water for 2 weeks before larvae were introduced (exposed) (FIG. 8A). The present inventors observed that larvae in the exposed Csp_P agar treatment experienced more rapid death, than those in the fresh Csp_P agar treatments (Cox Regression: P<0.0001). The present inventors then heat-treated whole Csp_P and control agar pellets at room temperature, 37° C. or 54° C. for two weeks, and then fed them to larvae (FIG. 8B), where the present inventors observed that heat treatment had no effect on the larvicidal activity of the Csp_P agar pellets (Cox Regression: P=0.929). In all experiments, groups of 30 ROCK L2 larvae were provided either a control or non-live Csp_P agar pellet in 300 ml of deionized water.
Figure 8B:
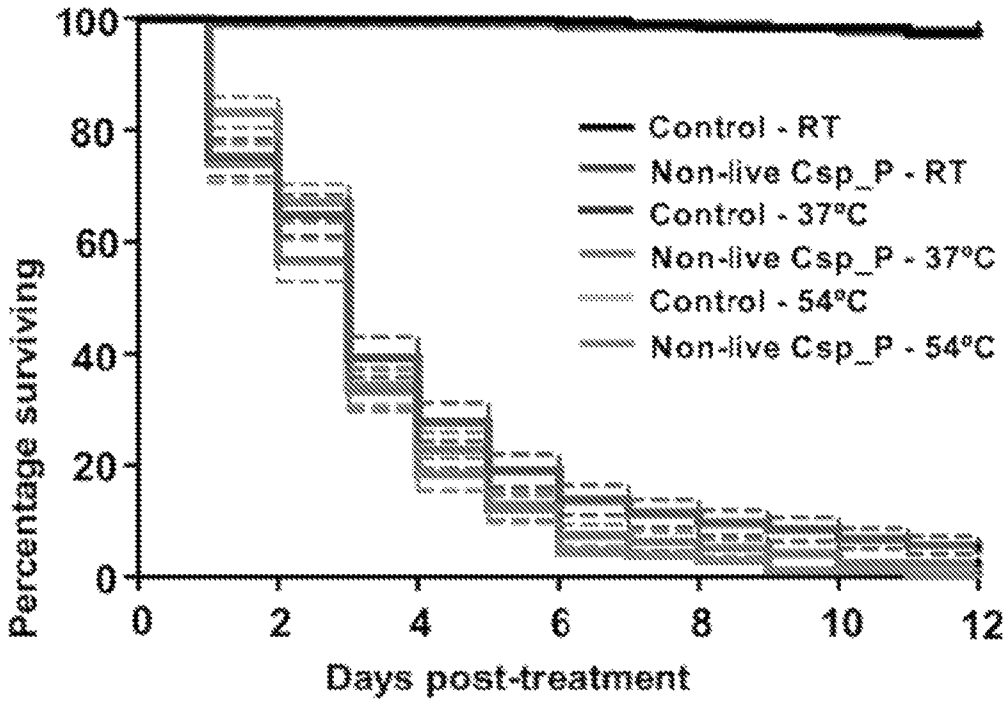
Figures 9A, 9B, 9C, 9D, 9E, 9F:
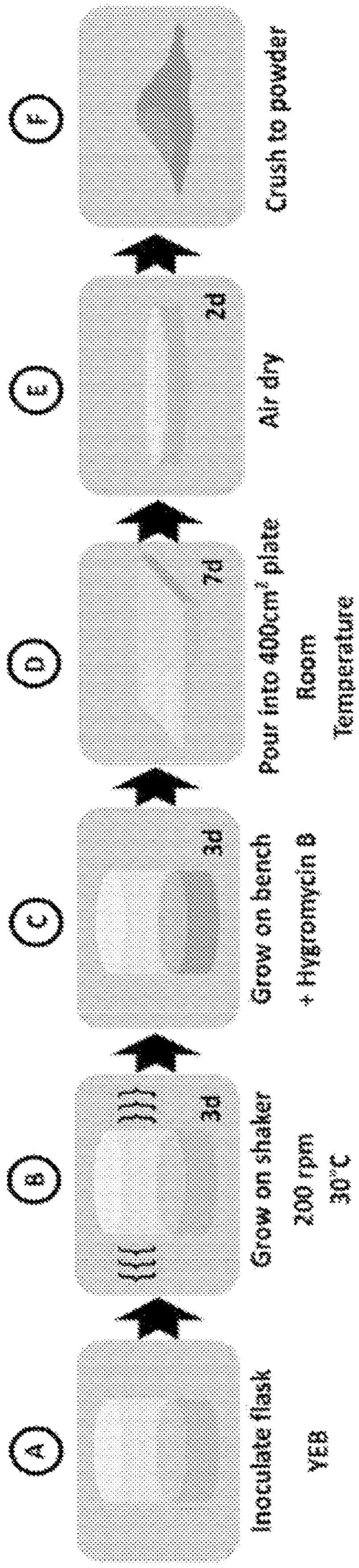
FIG. 9A-9F. Visual protocol for preparing liquid culture-based Csp_P powder biopesticide.

The present inventors then sought to assess the activity of the non-live Csp_P powder against field-collected larvae in their natural breeding habitats. The present inventors collected larvae and water from 11 different breeding sites across Eastern Puerto Rico. The sites included a variety of plastic containers, pails and tires (Table 2). Larvae from these breeding sites were taxonomically identified, and fell into three categories: (1) *Aedes aegypti* only, (2) *Aedes aegypti* and *Culex quinquefasciatus*, and (3) *Culex quinquefasciatus* only. The water and larvae within these breeding sites were transported to the semi-field facility and then divided into two cups, with half fed a control pellet, and half fed a pellet containing non-live Csp_P. In these experiments (FIG. 6), the present inventors monitored adult eclosion rather than larval mortality, as the breeding site water was typically too opaque to perform and accurate assessment of larval mortality. Across all breeding sites, there were 374 larvae involved in each of the control and non-live Csp_P treatments. For the control treatment, 342 larvae eclosed as adults (91.44%) and 32 died during the course of the experiment. For non-live Csp_P treated cups, 9 adult mosquitoes eclosed (2.41%), 5 females and 4 males, and 365 larvae died (Fisher's exact test: Odds Ratio=433.4, P<0.0001). Cox Regression analysis indicated that treatment with non-live Csp_P was a significant factor affecting the likelihood of adult eclosion, with larvae from a non-live Csp_P treated cup 125 times less likely to eclose than untreated larvae (Cox Regression: W=179.11, df=1, Exp β=0.008, P<0.0001).

DISCUSSION

The present inventors have developed a novel insecticide based on a non-live, air-dried preparation of the bacterium *Chromobacterium* species Panama (Csp_P). Previous reports from the present inventors' group have demonstrated that live Csp_P is a highly effective mosquitocidal agent that can rapidly kill the larvae and adults of mosquito vectors of medically important pathogens, including *An. gambiae* and *Ae. aegypti* (27, 30). Given the potential environmental and human/animal health concerns associated with an insecticidal preparation based on live bacteria, as well as complications with storage and shelf-life, the present inventors sought to develop a formulation containing non-live Csp_P that also retained killing activity against mosquito larvae.

Although the development of a potential mosquitocidal formulation involving non-live Csp_P is still in the early stages, the biopesticide that the present inventors have developed possesses many desirable properties for an insecticide. The present inventors' results confirm that no Csp_P cells survive the air-drying process used during preparation, indicating that releasing this product into the field would not spread live bacteria. The current formulation is fast-acting, and capable of killing mosquito larvae within an average of 2-3 days post-exposure. Interestingly, the present inventors observed that exposure to non-live Csp_P halted larval development, which potentially facilitated a greater window of time for larvae to ingest the biopesticide and be killed. This was in line with what the present inventors observed in a previous study, where the larvae of *An. gambiae* females that survived treatment with live Csp_P experienced a developmental delay (31). The present inventors also determined that the powder had an $LD_{50}$ of 11.36 mg per liter of larval rearing water, under laboratory conditions. As mass culturing of bacteria can be quite expensive, such a low effective dose is a highly beneficial trait.

Additionally, the powder had broad larvicidal activity against a broad range of mosquito targets, including those of high epidemiological importance. This included the prominent mosquito vectors *An. gambiae, Ae. aegypti*, and *Cx. quinquefasciatus*, and also *Ae. mediovitattus*. The Csp_P biopesticide was most effective against *Cx. quinquefasciatus* larvae, where the present inventors observed a shorter average time-to-death post-exposure than for the other species. Mosquitoes of the *Culex* genus include prominent vectors of West Nile virus, Japanese encephalitis virus, and the nematodes that cause filariasis. All of these pathogens have significant impacts on human health. Non-live Csp_P powder also effectively kills larvae from the pyrethroid-resistant *Ae. aegypti* NR-48830 line, which was expected given that this line had not previously been exposed to the present inventors' insecticide. Given the widespread usage of pyrethroids in mosquito control programs around the world, there are high levels of pyrethroid resistance amongst mosquito populations (32, 33), and the present inventors' data suggest that the biopesticide could prove to be a good candidate compound for a novel insecticide to target these resistant populations.

Non-live Csp_P powder also appears to be highly temperature stable, with accelerated shelf life assays demonstrating that the larvicidal activity is unaffected by heat treatment at 54° C. for two weeks, which is comparable to storage at room temperature for one year. Interestingly, while treatment at 70° C. for two weeks did lead to slightly reduced activity, more than 95% of the larvae that were exposed were still killed. Additionally, heat-treatment of whole agar pellets for 7 days had no significant impact on larvicidal activity. All of these results indicate that the as-yet-uncharacterized active ingredient in the present inventors' insecticide is highly heat stable, and that non-live Csp_P powder will likely have a shelf life in excess of one year.

The present inventors' data demonstrate that non-live Csp_P powder is an effective larvicide against laboratory- and field-derived mosquitoes, under semi-field conditions. Experiments were conducted at a semi-field facility in Puerto Rico, mosquito larvae were kept in a contained environment, under a tarpaulin, but otherwise exposed to ambient environmental conditions. The present inventors observed that exposure to non-live Csp_P powder was highly effective at killing laboratory-reared *Ae. aegypti* and *Ae. mediovittatus* larvae that were moved to the field site at 3 days post-hatching. The present inventors saw similar efficacy when the biopesticide was trialed against $G_1$ larvae from 11 different field-derived *Ae. aegypti* populations that were collected from around Puerto Rico, where all larvae died within 4 days of exposure. Critically, the Csp_P biopesticide was highly effective at preventing the emergence of adult *Ae. aegypti* and/or *Culex* mosquitoes from natural breeding site water, suggesting that it could be successfully deployed to target a range of different mosquito populations and larval habitats in the field.

The cause of the larvicidal activity observed with the non-live Csp_P powder is still unclear. The present inventors observed larvicidal activity for fishmeal/gelatin pellets containing either live Csp_P or non-live Csp_P. However, larvae that were fed on pellets containing live bacteria died approximately 1-2 days sooner on average than those fed on non-live bacterial powder. It is possible that some factor involved in generating larvicidal activity was lost during the air drying process, that there were differences in concentrations of larvicidal factors between the live and non-live treatments, or even that proliferation of live Csp_P in the larval gut could have led to increased levels of the insecticidal agent(s). Previous data from the present inventors' group indicates that live Csp_P can mediate mosquito death through the production of hydrogen cyanide (30). However, the present inventors did not detect cyanide in any of the 5 non-live, air-dried Csp_P powders that the present inventors tested. This result was not particularly surprising given that cyanide is a volatile compound that is known to be lost from Csp_P cultures during evaporation (30). These observations may indicate that the non-live Csp_P powder might kill mosquito larvae through alternative mechanisms to the live bacteria, or that some factors that mediate mosquito killing in live Csp_P are lost during the air-drying process. To fully elucidate these differences, it will likely be necessary to identify the active ingredient associated with larval killing in the non-live Csp_P powder.

The present inventors' findings suggest that not all bacteria have larvicidal activity when fed to mosquitoes as non-live powders, indicating that the larvicidal effects the present inventors observed with the non-live Csp_P powder were not simply a by-product of the culturing protocol that the present inventors used. At this stage, it is still unclear if this larvicidal active ingredient in the powder is something that is specific to Csp_P or something common amongst members of the genus *Chromobacterium*. The latter could be quite likely, given that many *Chromobacterium* species have larvicidal properties when fed live to mosquitoes (30). Interestingly, there is already a commercially-available insecticide Grandevo (Marrone BioInovations), which was developed from a preparation of the bacterium *Chromobacterium subtsugiae*, and is used to target agricultural pest species (34, 35). It is unclear if Grandevo shares a mechanism of action with non-live Csp_P powder.

CONCLUSIONS

The present inventors have developed a novel biopesticide based on a non-live air-dried preparation of the bacterium *Chromobacterium* sp. Panama, which is highly effective at killing the larvae of multiple mosquito species, including key vectors of malaria, and the dengue and Zika viruses. This insecticide is still in the early stages of development, but displays many beneficial properties for an insecticide, including low effective dosage, and an active ingredient that appears to be highly heat-stable. Critically, the present inventors' data demonstrate that the non-live Csp_P biopesticide is highly effective at preventing the emergence of adult mosquitoes, under semi-field conditions.

REFERENCES

1. WHO. 2018. World Malaria Report. Geneva.
2. WHO. 27 Mar. 2019 2019. Malaria. Fact Sheets.
3. WHO. 15 Apr. 2019 2019. Dengue and severe dengue. Fact Sheets.
4. WHO. 12 Apr. 2017 2017. Chikungunya. Fact Sheets.
5. WHO. 7 May 2019 2019. Yellow fever. Fact Sheets.
6. WHO. 20 Jul. 2018 2018. Zika virus. Fact Sheets.
7. Bhatt S, Gething P W, Brady O J, Messina J P, Farlow A W, Moyes C L, Drake J M, Brownstein J S, Hoen A G, Sankoh O, Myers M F, George D B, Jaenisch T, Wint G R, Simmons C P, Scott T W, Farrar J J, Hay S I. 2013. The global distribution and burden of dengue. Nature 496: 504-7.
8. Gould E A, Higgs S. 2009. Impact of climate change and other factors on emerging arbovirus diseases. Trans R Soc Trop Med Hyg 103:109-21.
9. Gubler D J. 2011. Dengue, Urbanization and Globalization: The Unholy Trinity of the 21(st) Century. Trop Med Health 39:3-11.
10. Weaver S C, Reisen W K. 2010. Present and future arboviral threats. Antiviral Res 85:328-45.
11. Dutra H L, Caragata E P, Moreira L A. 2017. The re-emerging arboviral threat: Hidden enemies: The emergence of obscure arboviral diseases, and the potential use of *Wolbachia* in their control. Bioessays 39.
12. Conrad M D, Rosenthal P J. 2019. Antimalarial drug resistance in Africa: the calm before the storm? Lancet Infect Dis 19:e338-e351.

13. WHO. 2011. Global Insecticide use for Vector-Borne Disease Control, Fifth ed, France.
14. Killeen G F, Smith T A, Ferguson H M, Mshinda H, Abdulla S, Lengeler C, Kachur S P. 2007. Preventing childhood malaria in Africa by protecting adults from mosquitoes with insecticide-treated nets. PLoS Med 4:e229.
15. Du Y Z, Nomura Y, Satar G, Hu Z N, Nauen R, He S Y, Zhorov B S, Dong K. 2013. Molecular evidence for dual pyrethroid-receptor sites on a mosquito sodium channel. Proceedings of the National Academy of Sciences of the United States of America 110:11785-11790.
16. Miller J E, Lindsay S W, Armstrong J R M. 1991. Experimental Hut Trials of Bednets Impregnated with Synthetic Pyrethroid or Organophosphate Insecticide for Mosquito-Control in the Gambia. Medical and Veterinary Entomology 5:465-476.
17. Rose R I. 2001. Pesticides and public health: Integrated methods of mosquito management. Emerging Infectious Diseases 7:17-23.
18. Nishiura J T, Ho P, Ray K. 2003. Methoprene interferes with mosquito midgut remodeling during metamorphosis. J Med Entomol 40:498-507.
19. Chandler D, Bailey A S, Tatchell G M, Davidson G, Greaves J, Grant W P. 2011. The development, regulation and use of biopesticides for integrated pest management. Philos Trans R Soc Lond B Biol Sci 366:1987-98.
20. Berry C. 2012. The bacterium, *Lysinibacillus sphaericus*, as an insect pathogen. Journal of Invertebrate Pathology 109:1-10.
21. Lacey L A. 2007. *Bacillus thuringiensis* serovariety *israelensis* and *Bacillus sphaericus* for mosquito control. J Am Mosq Control Assoc 23:133-63.
22. Scholte E J, Ng'habi K, Kihonda J, Takken W, Paaijmans K, Abdulla S, Killeen G F, Knols B G. 2005. An entomopathogenic fungus for control of adult African malaria mosquitoes. Science 308:1641-2.
23. Macoris M D, Andrighetti M T M, Takaku L, Glasser C M, Garbeloto V C, Bracco J E. 2003. Resistance of *Aedes aegypti* from the State of Sao Paulo, Brazil, to organophosphates insecticides. Memorias Do Instituto Oswaldo Cruz 98:703-708.
24. Protopopoff N, Matowo J, Malima R, Kavishe R, Kaaya R, Wright A, West P A, Kleinschmidt I, Kisinza W, Mosha F W, Rowland M. 2013. High level of resistance in the mosquito *Anopheles gambiae* to pyrethroid insecticides and reduced susceptibility to bendiocarb in north-western Tanzania. Malar J 12:149.
25. Ranson H, Lissenden N. 2016. Insecticide Resistance in African *Anopheles* Mosquitoes: A Worsening Situation that Needs Urgent Action to Maintain Malaria Control. Trends Parasitol 32:187-196.
26. Beier J C, Keating J, Githure J I, Macdonald M B, Impoinvil D E, Novak R J. 2008. Integrated vector management for malaria control. Malar J 7 Suppl 1:S4.
27. Ramirez J L, Short S M, Bahia A C, Saraiva R G, Dong Y, Kang S, Tripathi A, Mlambo G, Dimopoulos G. 2014. *Chromobacterium* Csp_P reduces malaria and dengue infection in vector mosquitoes and has entomopathogenic and in vitro anti-pathogen activities. PLoS Pathog 10:e1004398.
28. Saraiva R G, Huitt-Roehl C R, Tripathi A, Cheng Y Q, Bosch J, Townsend C A, Dimopoulos G. 2018. *Chromobacterium* spp. mediate their anti-*Plasmodium* activity through secretion of the histone deacetylase inhibitor romidepsin. Sci Rep 8:6176.
29. Saraiva R G, Fang J, Kang S, Anglero-Rodriguez Y I, Dong Y, Dimopoulos G. 2018. Aminopeptidase secreted by *Chromobacterium* sp. Panama inhibits dengue virus infection by degrading the E protein. PLoS Negl Trop Dis 12:e0006443.
30. Short S M, van Tol S, MacLeod H J, Dimopoulos G. 2018. Hydrogen cyanide produced by the soil bacterium *Chromobacterium* sp. Panama contributes to mortality in *Anopheles gambiae* mosquito larvae. Sci Rep 8:8358.
31. Short S M, van Tol S, Smith B, Dong Y, Dimopoulos G. 2018. The mosquito adulticidal *Chromobacterium* sp. Panama causes transgenerational impacts on fitness parameters and elicits xenobiotic gene responses. Parasit Vectors 11:229.
32. Smith L B, Kasai S, Scott J G. 2016. Pyrethroid resistance in *Aedes aegypti* and *Aedes albopictus*: Important mosquito vectors of human diseases. Pesticide Biochemistry and Physiology 133:1-12.
33. Vontas J, Kioulos E, Pavlidi N, Morou E, della Torre A, Ranson H. 2012. Insecticide resistance in the major dengue vectors *Aedes albopictus* and *Aedes* aegypti. Pesticide Biochemistry and Physiology 104:126-131.
34. Ray H A, Hoy M A. 2014. Effects of Reduced-Risk Insecticides on Three Orchid Pests and Two Predacious Natural Enemies. Florida Entomologist 97:972-978.
35. Shapiro-Ilan D I, Cottrell T E, Bock C, Mai K, Boykin D, Wells L, Hudson W G, Mizell R F, 3rd. 2017. Control of Pecan Weevil With Microbial Biopesticides. Environ Entomol 46:1299-1304.
36. Beier J C, Muller G C, Gu W, Arheart K L, Schlein Y. 2012. Attractive toxic sugar bait (ATSB) methods decimate populations of *Anopheles* malaria vectors in arid environments regardless of the local availability of favoured sugar-source blossoms. Malar J 11:31.
37. Muller G C, Junnila A, Qualls W, Revay E E, Kline D L, Allan S, Schlein Y, Xue R D. 2010. Control of *Culex quinquefasciatus* in a storm drain system in Florida using attractive toxic sugar baits. Med Vet Entomol 24:346-51.
38. Stewart Z P, Oxborough R M, Tungu P K, Kirby M J, Rowland M W, Irish S R. 2013. Indoor application of attractive toxic sugar bait (ATSB) in combination with mosquito nets for control of pyrethroid-resistant mosquitoes. PLoS One 8:e84168.
39. Blackburn M B, Farrar R R, Jr., Sparks M E, Kuhar D, Mitchell A, Gundersen-Rindal D E. 2017. *Chromobacterium sphagni* sp. nov., an insecticidal bacterium isolated from Sphagnum bogs. Int J Syst Evol Microbiol 67:3417-3422.
40. Blackburn M B, Farrar R R, Jr., Sparks M E, Kuhar D, Mowery J D, Mitchell A, Gundersen-Rindal D E. 2019. *Chromobacterium* phragmitis sp. nov., isolated from estuarine marshes. Int J Syst Evol Microbiol 69:2681-2686.
41. Lima-Bittencourt C I, Astolfi-Filho S, Chartone-Souza E, Santos F R, Nascimento A M. 2007. Analysis of *Chromobacterium* sp. natural isolates from different Brazilian ecosystems. BMC Microbiol 7:58.
42. Lima-Bittencourt C I, Costa P S, Barbosa F A, Chartone-Souza E, Nascimento A M. 2011. Characterization of a *Chromobacterium haemolyticum* population from a natural tropical lake. Lett Appl Microbiol 52:642-50.
43. Santini A C, Magalhaes J T, Cascardo J C, Correa R X. 2016. Genetic variability in isolates of *Chromobacterium violaceum* from pulmonary secretion, water, and soil. Genet Mol Res 15.
44. Soby S D, Gadagkar S R, Contreras C, Caruso F L. 2013. *Chromobacterium vaccinii* sp. nov., isolated from native and cultivated cranberry (*Vaccinium macrocarpon* Ait.) bogs and irrigation ponds. Int J Syst Evol Microbiol 63:1840-6.

45. Barrera R, Mackay A J, Amador M. 2013. A novel autocidal ovitrap for the surveillance and control of *Aedes aegypti*. J Am Mosq Control Assoc 29:293-6.
46. Poole-Smith B K, Hemme R R, Delorey M, Felix G, Gonzalez A L, Amador M, Hunsperger E A, Barrera R. 2015. Comparison of vector competence of *Aedes mediovittatus* and *Aedes aegypti* for dengue virus: implications for dengue control in the Caribbean. PLoS Negl Trop Dis 9:e0003462.
47. Bahia A C, Dong Y M, Blumberg B J, Mlambo G, Tripathi A, BenMarzouk-Hidalgo O J, Chandra R, Dimopoulos G. 2014. Exploring *Anopheles* gut bacteria for *Plasmodium* blocking activity. Environmental Microbiology 16:2980-2994.
48. EPA. 2002. OPPTS 830.6317 Storage Stability. United States Environmental Protection Agency.

Example 2. A scale-up is developed using a compatible culturing protocol that minimizes production time and costs, and maximizes yield of the active ingredient without compromising the stability and the efficacy found in the current formulation.

Example 3. An optimized formulation for producing the biopesticide is developed. In one embodiment, this is based on liquid media, as this would simplify the mass production of the biopesticide using standard fermentation technology.

Example 4. The active ingredient is identified and a method for quantifying the level of the active ingredient in culture is developed, which could expedite the process and allow for improved larvicidal activity. In certain embodiments, the identification of the active ingredient and developed method improves powder yield, while decreasing time costs associated with production.

Example 5. The residual activity of the current formulation is considered. In the experiments described herein, the present inventors observed that gelatin-based pellets dissolved in water quite rapidly, while agar-based pellets had greater structural integrity, and appeared to retain or improve larvicidal activity when left in water for two weeks prior to treatment. In particular embodiments, an effective larvicidal agent must not persist in the environment for too short a time, as it could necessitate more frequent treatment. Consequently, the stability and persistence of the biopesticide in water is evaluated. In certain embodiments, it would not persist for too long, as this risks a loss of activity over time, meaning that larvae would get exposed to lower-than-optimal doses and then be more likely to develop resistance. For these reasons, whether larvae can develop resistance to non-live Csp_P powder is evaluated, and potential mechanisms of resistance are investigated.

Example 6. An optimized formulation against adult mosquitoes, and against other animal species, particularly agricultural pests and other vectors, is developed and tested, as this will indicate whether the non-live Csp_P biopesticide has a broader scope for potential use. Rigorous testing of the biopesticide is performed in line with WHO Pesticide Evaluation Scheme guidelines, to determine if the biopesticide affects non-target species, including beneficial insects such as honeybees. Potential ecological and health and safety concerns associated with deployments into the environment are also investigated by testing the biopesticide against mammals. It should be noted that there are attractive toxic baits used to target mosquitoes, which can be developed in a way that prevents non-target insects from feeding (36-38), and this technology may be utilized for future trials with adult mosquitoes.

Example 7: Solubility of the Csp_P mosquitocidal active ingredient (AI) in a liquid ASB. A method to dilute Csp_P airdried powder in in a highly viscous fruit juice-based attractive sugar bait (ASB) was developed, and solution was then provided to mosquitoes though a micro-punctured membrane which mosquitoes could feed on.

Figure 18A:
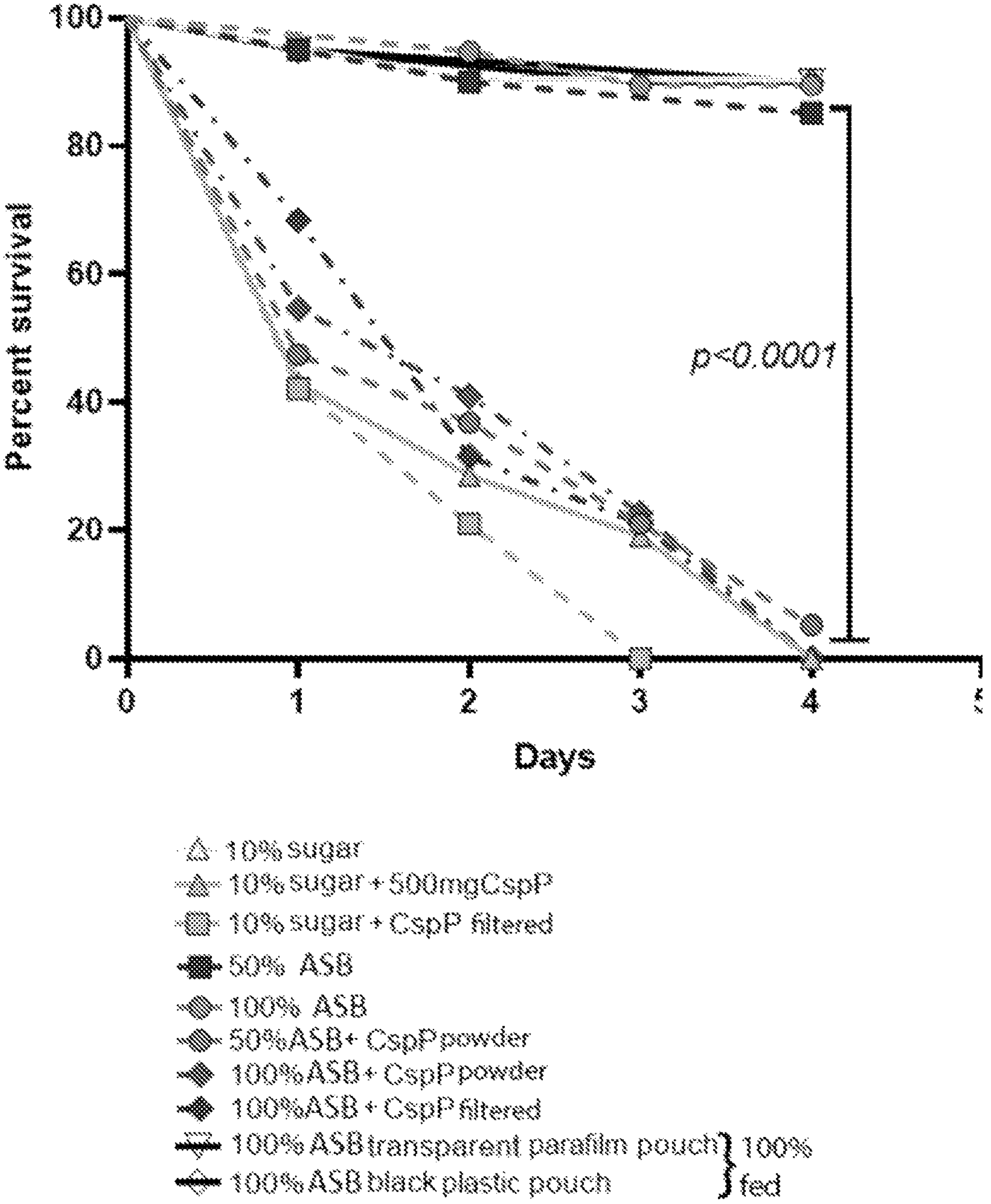
FIG. 18A-18B.

The ASB was heated to 52° C. for 1 hour and 500 mg/ml Csp_P airdried powder was added to the warm ASB in a 1:9. The powder and the ASB were thoroughly mixed using a Pellet Pestle Motor in a tube, resulting in a jelly like mixture. The 100% ASB, containing 500 mg/ml Csp_P airdried powder, showed comparable killing activity to the 50% ASB formulation (FIG. 18A). The Csp_P airdried powder was also dissolved the ASB in a 1:1 ration, and this solution also showed potent killing activity.

Figure 18B:
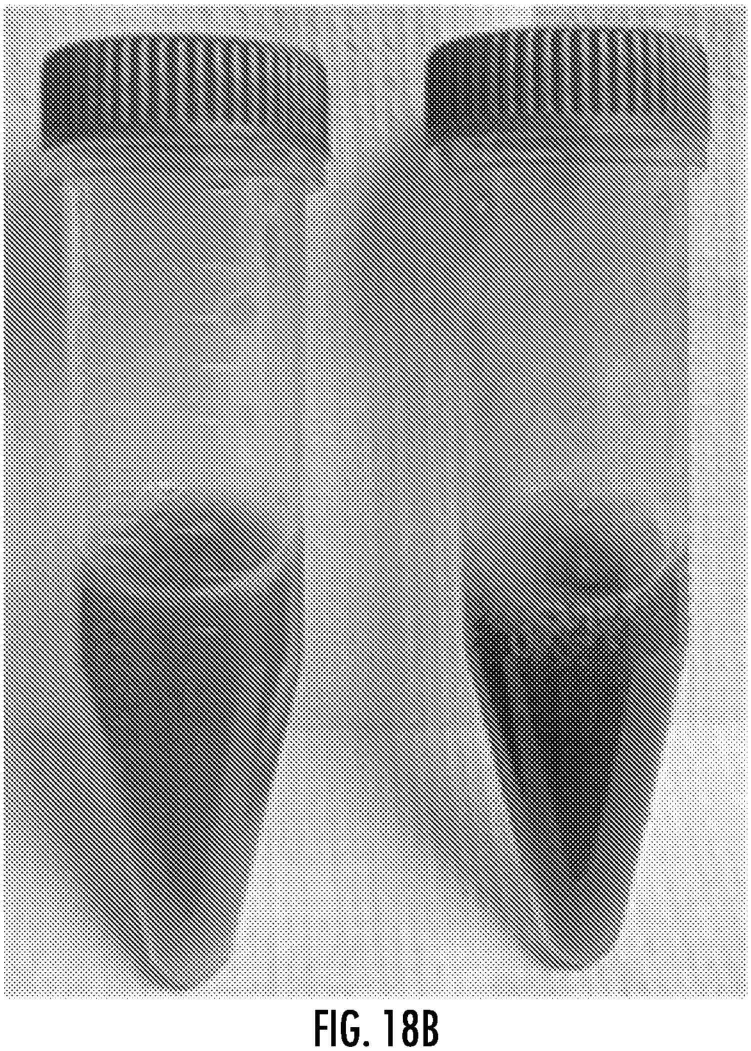
Figure 19A:
FIG. 19A-19C. Mosquitoes feeding on Csp_P—ASB through a parafilm membrane (FIG. 19A and FIG. 19B). A water-soaked cotton ball is included in the assay to prevent dehydration pf mosquitoes (FIG. 19B). Pouches made of parafilm and plastic trash bag filled with Csp_P-ASB (FIG. 19C). Small holes have been made through syringe to enable leakage of ASB as olfactory cue.
Figure 19B:
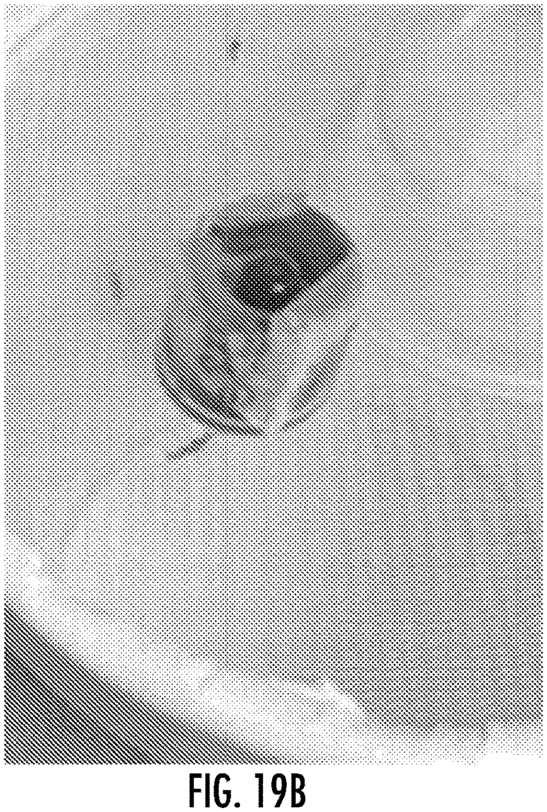
Figure 19C:
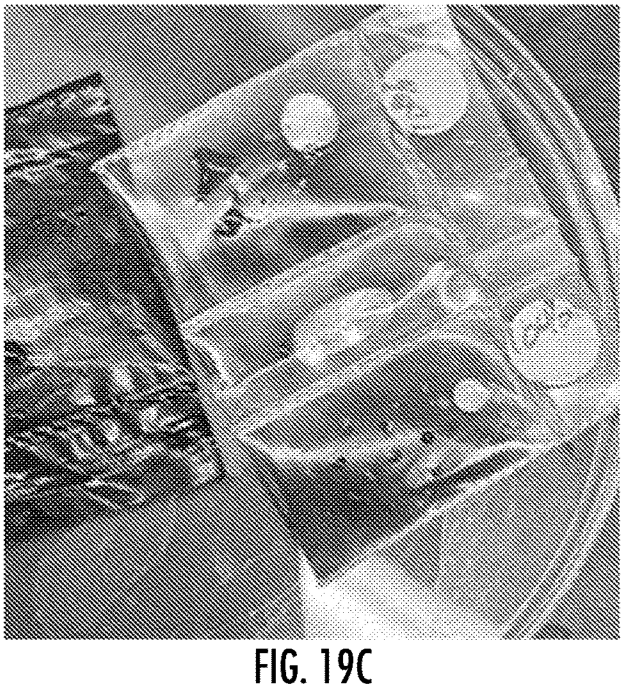

The Csp_P airdried powder is prepared through a method that involves a final step of extensive grinding of a dried bacteria-biofilm lattice. Microscopic examination of the powder did not identify any regulate rod-shaped bacteria, suggesting that the drying and grinding process results in fragmentation of cells. To investigate whether the AI contained in the airdried Csp_P powder is soluble in the ASB, or whether it is associates with cellular debris that could settle in the ATSB feeding station, we performed an assay in which 500 mg airdried Csp_P powder was diluted in 1 ml of sterile 10% sucrose solution, and then centrifuged at 13,000 rpm for 10 minutes to pellet cellular debris. The supernatant was then removed and passed through a 0.22-micron syringe filter to further remove any remaining cellular debris. This filtered supernatant was then diluted 1:1 in either 100% ASB or 20% sucrose solution and provided to mosquitoes using our standard feeding assay, resulting in a mortality comparable to that of the non-filtered Csp_P-ASB formulation (FIG. 18A) (Kaplan-Meier survival analysis, Log-rank (Mantel-Cox) test: $X^2$=179.6, P<0.0001)). The comparison of survival curves between unfiltered and centrifuged/filtered Csp_P mixture showed no difference (FIG. 18A) (Log-rank(Mantel-Cox): P=0.2563). This assay demonstrated that the AI contained in the Csp_P airdried powder is not associated with cellular debris and does not settle, but is rather in suspension in the ASB. We have also observed that the Csp_P powder dissolved in the ASB remains in suspension; there is no settling when the preparation is left for several weeks without agitation (FIG. 18B).

Figure 20A:
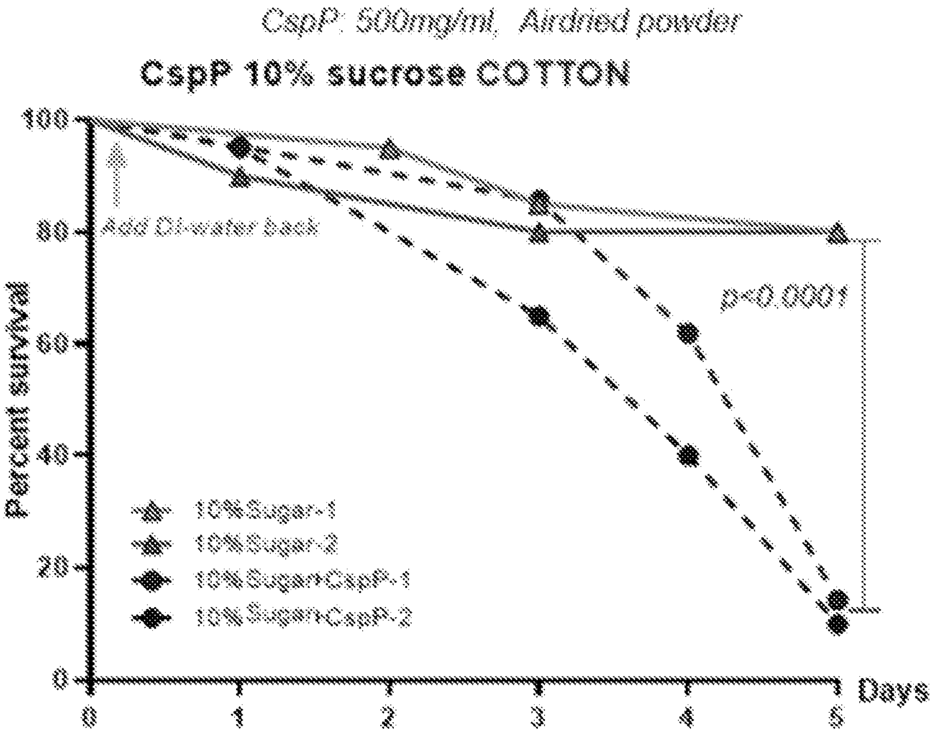
FIG. 20A-20C. Comparison of Csp_P airdried powder (500 mg/ml) delivery through 10% sucrose solution (FIG. 20A) and 50% ASB (FIG. 20B), in either a cotton ball or through a parafilm membrane. Large scale experiment with cages were also assayed with parafilm membrane system developed to mimic semi-field feeding condition (FIG. 20C).
Figure 20B:
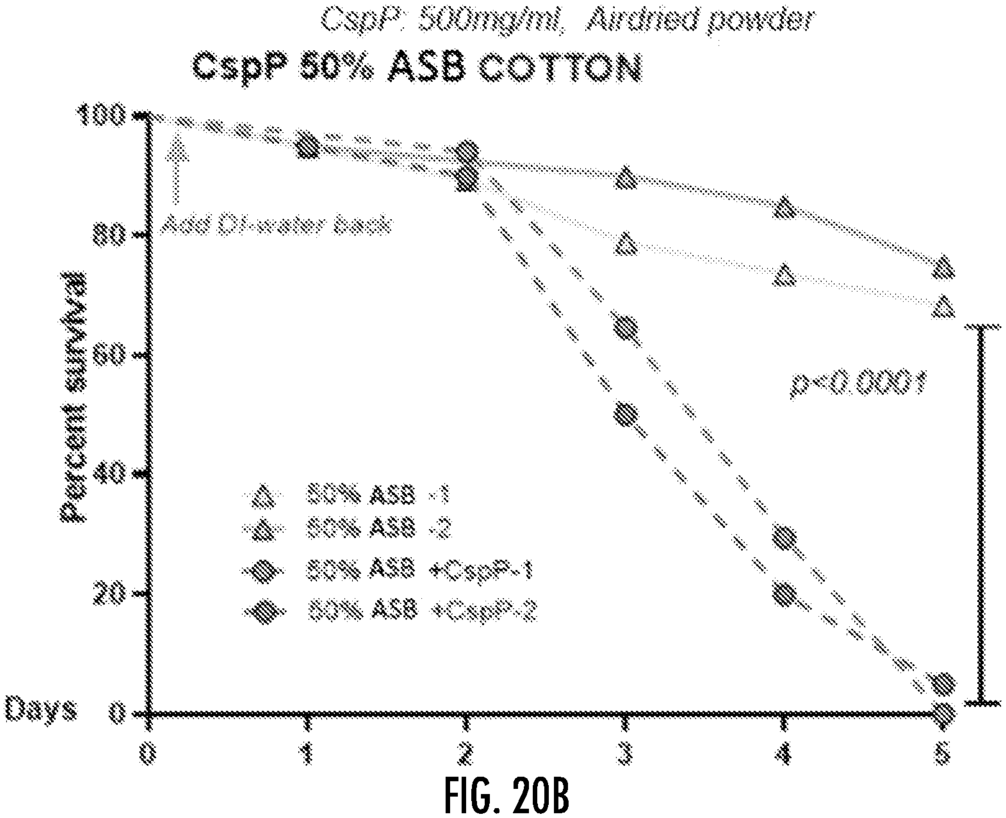
Figure 20C:
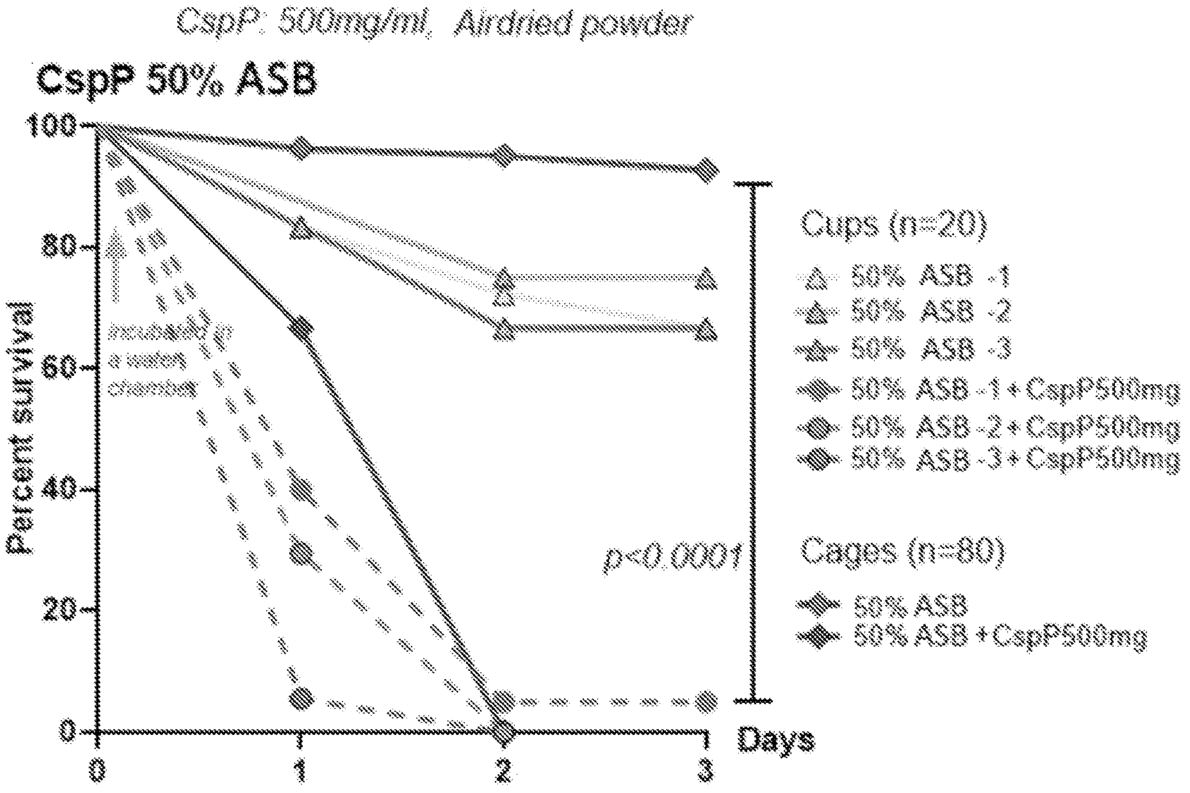

Example 8: Csp_P-ASB delivery method to adult mosquitoes for causing mortality. The Csp_P airdried powder and Csp_P organic extract were dissolved in the ASB in a 1:1 and 1:9 ratio. This solution was then provided to mosquitoes though a micro-punctured membrane which mosquitoes could feed on. Small holes were made with an insulin syringe in the membranes to allow small amounts of the Csp_P-ASB to leak out and provide an olfactory cue. Both parafilm- and plastic (trash bag)—based membranes for both 500 mg/ml Csp_P airdried powder in a 10% sugar solution and the ASB were tested and resulted in mortality (FIG. 18A & 2, Log-rank (Mantel-Cox) test: $X^2$=0.3703, P=0.9463). Delivery of Csp_P-ASB to mosquitoes through a soaked cotton ball resulted in a significant slower mortality compared to membrane (FIG. 20A,B) (Log-rank(Mantel-Cox) test; 10% sucrose with cotton: $X^2$=30.1, P<0.0001, LT50=4.5; ASB with cotton: $X^2$=35.92, P<0.0001, LT50=3.75; 50% ASB with membrane: $X^2$=215.1, P<0.0001, LT50=1), likely because of less efficient feeding since the soaked cotton balls tend to dessicate. To avoid mosquito mortality derived from dehydration an extra cotton ball with water was supplied along with the Csp_P-ASB (FIG. 2B). We have also developed specific ASB-membrane feeding system to deliver Csp_P-ASB to larger numbers of mosquitoes (FIG. 2C), here referred to as a cage. Mortality assays performed in cups or larger cages showed similar killing efficiency when the Csp_P-ASB was delivered through a micropunctured membrane (FIG. 20C; Log-rank (Mantel-Cox) test: $X^2$=35.92, P<0.0001, LT50=2).

Figure 21A:
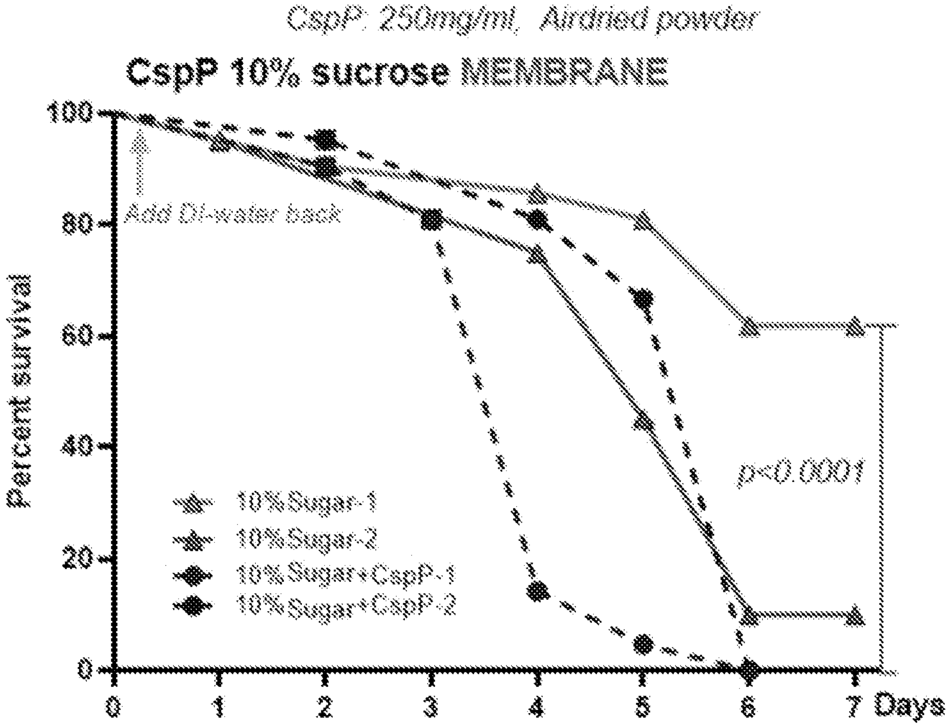
FIG. 21A-21F. Comparison of Csp_P airdried powder delivery through 10% sucrose solution and 50% ASB at concentrations of 250 mg/ml and 500 mg/ml through a parafilm membrane system. The titration of Csp_P-ASB was assayed at various dosage of 100-, 250-, and 500-mg/ml. The organic n-butanol fraction has shown drastic mortality compared to aqueous fraction in the ASB (50%) and compared to control 50% ASB-MeOH.
Figure 21B:
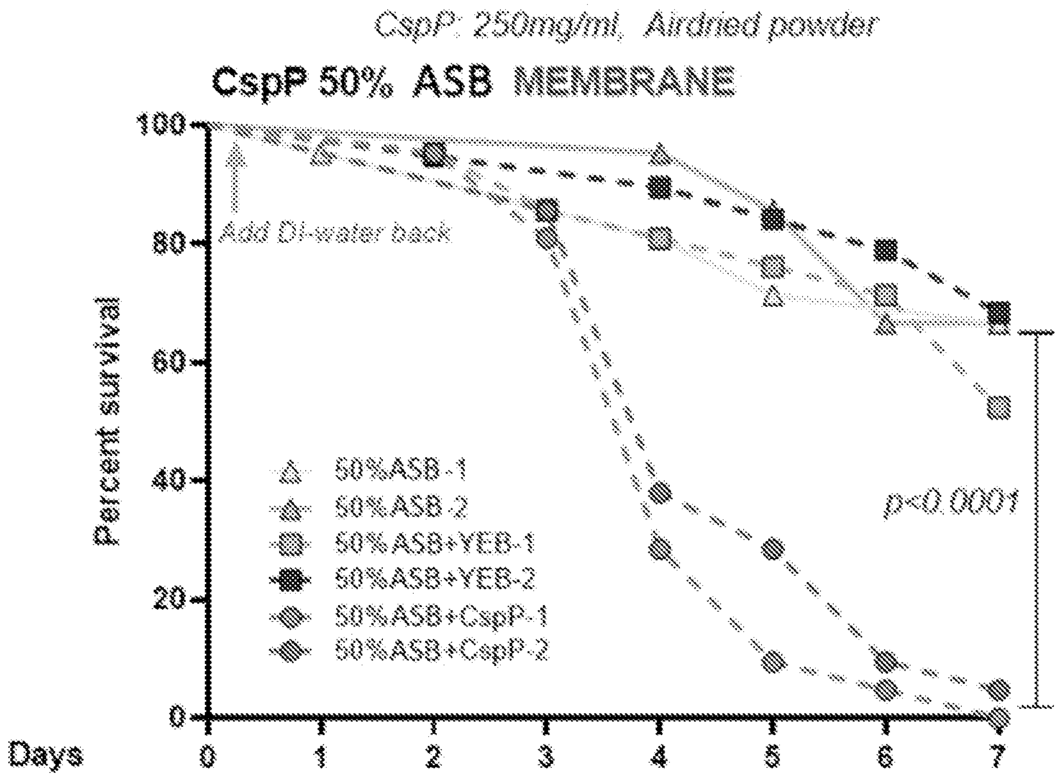
Figure 21C:
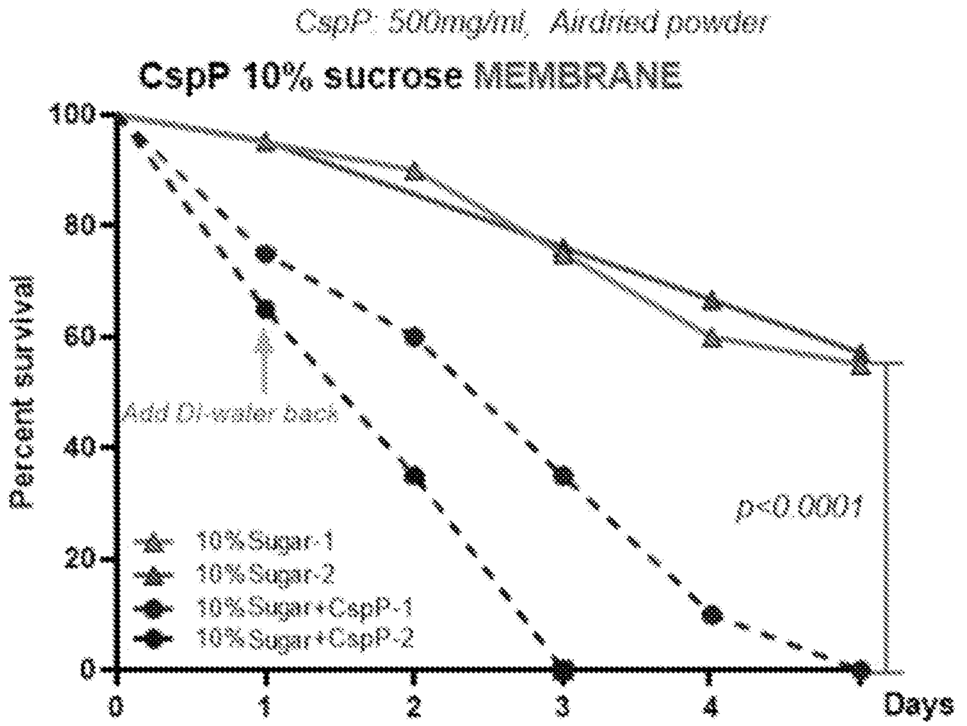
Figure 21D:
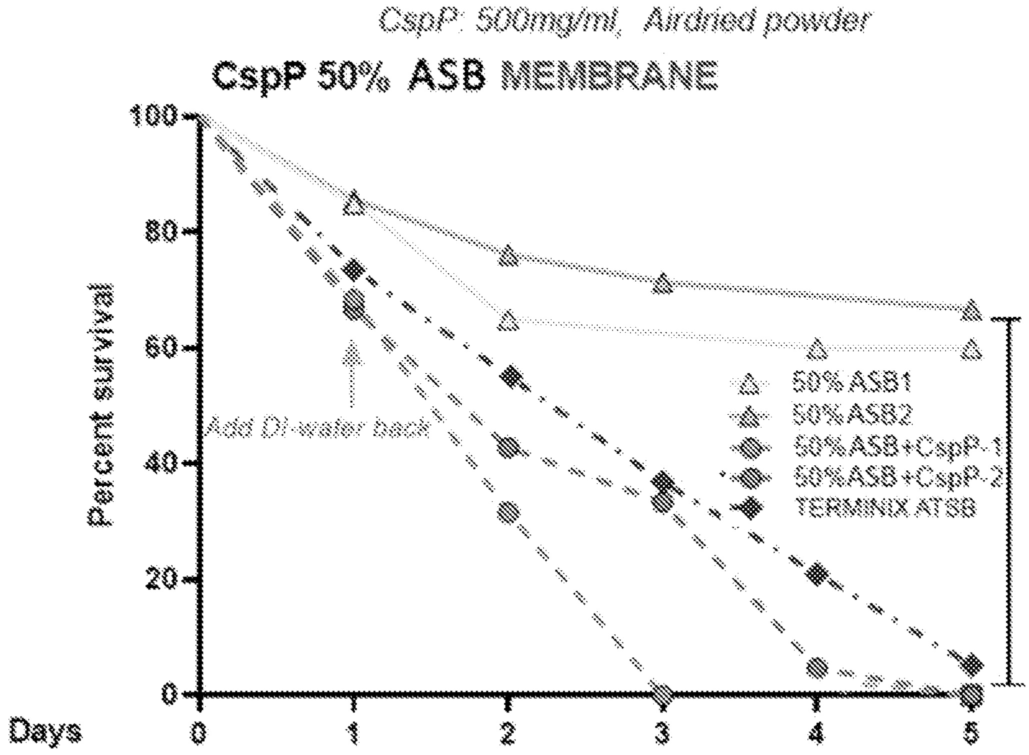
Figure 21E:
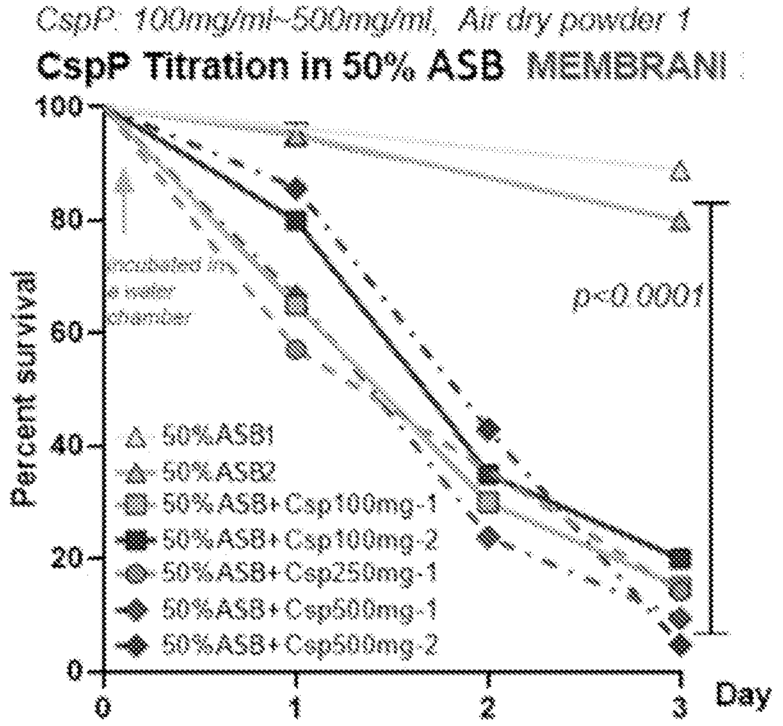

Example 9: Optimal concentrations of Csp_P airdried powder and organic extract in ASB for causing adult *Anopheles gambiae* mortality. To determine an optimal Csp_P airdried powder concentration in the ASB we tested 250 mg/ml and 500 mg/ml concentrations through membrane-based delivery to mosquitoes in either a 10% sucrose solution or a 50% ASB solution. At both concentrations, the Csp_P in the ASB and in the 10% sucrose solution performed equally well (FIG. 21A,B,C,D; Log-rank(Mantel-Cox) test; 250 mg/ml in 10% sucrose: $X^2$=44.93, P<0.0001, LT50=4~6; 50% ASB: $X^2$=48.63, P<0.0001, LT50=4)), and at 500 mg/ml near-complete mortality could be achieved between 3-4 days post exposure (FIG. 21C,D; Mantel-Cox; 10% sucrose: $X^2$=74.5, P<0.0001, LT50=2.5; 50% ASB: $X^2$=84.89, P<0.0001, LT50=2)). Membrane-based assays with either 100 mg/ml, 250 mg/ml and 500 mg/ml in ASB showed a predictable dose-dependent mortality rate, that did not differ greatly between the three concentrations (FIG. 21E). A positive control containing the commercial sprayable TERMINIX ATSB, based on garlic oil, was also tested and delivered to mosquitoes through the parafilm membrane, showing a mortality rate lesser than that of Csp_P-based formulations (FIG. 21D; $X^2$=84.89, P<0.0001, LT50=2 for Csp_P-500 mg/ml and LT50>3 for TERMINIX ASTB).

Figure 21F:
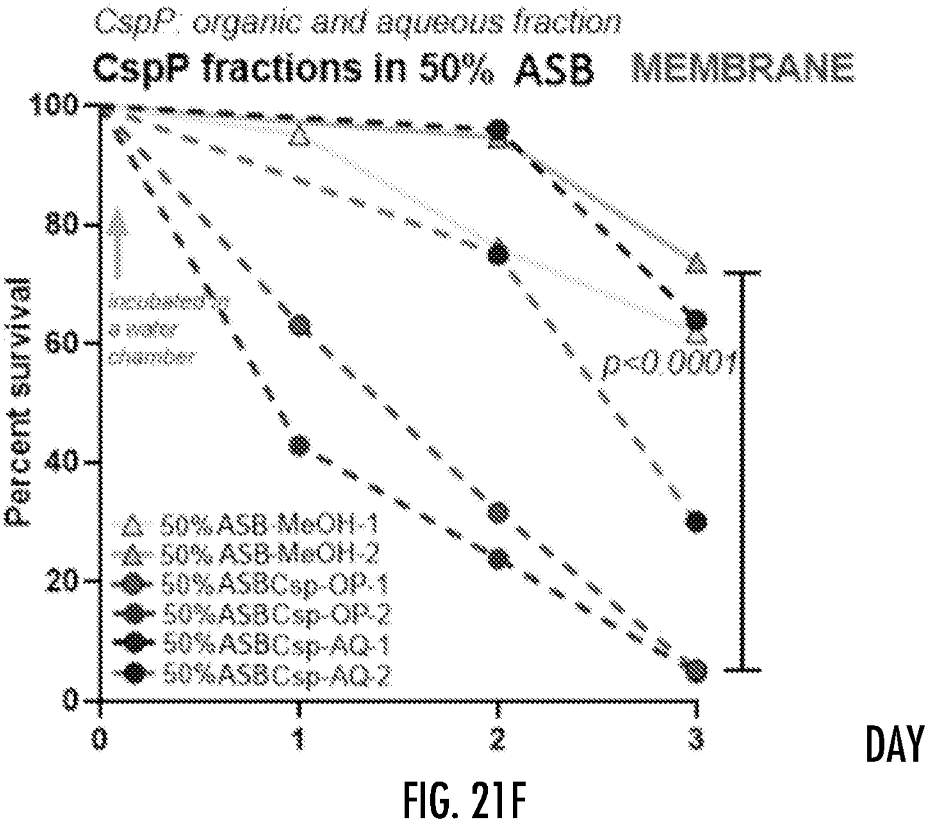

The Csp_P organic extraction preparation was also tested in 50% ASB formulation. Both the organic fraction (containing the AI) and aqueous fraction (control not containing AI) were concentrated using rotor-vapor for a couple of hours and the organic fraction was resuspended in methanol and the aqueous fraction was further concentrated 20 times. A volume of 500 ul of either the organic fraction (FIG. 21F; 50% Csp-OP) or methanol (as control, FIG. 21F; 50% ASB-MeOH) was mixed with the 1 ml of 50% ASB. This mixture was subjected to speed-vac for 20 minutes to evaporate the methanol completely, to avoid the mosquito mortality caused by methanol. For the aqueous fraction, 500 ul of the fraction was directly mixed in the 500 ul of 50% ASB (FIG. 21F; 50% ASB Csp-AQ). The organic fraction in the 50% ASB showed potent mosquitocidal activity, while the aqueous fraction showed marginal killing activity (FIG. 21F; Log-rank (Mantel-Cox) test; organic fraction: $X^2$=68.15, P<0.0001, LT50=1.5; aqueous fraction: LT50>3).

Figure 22A:
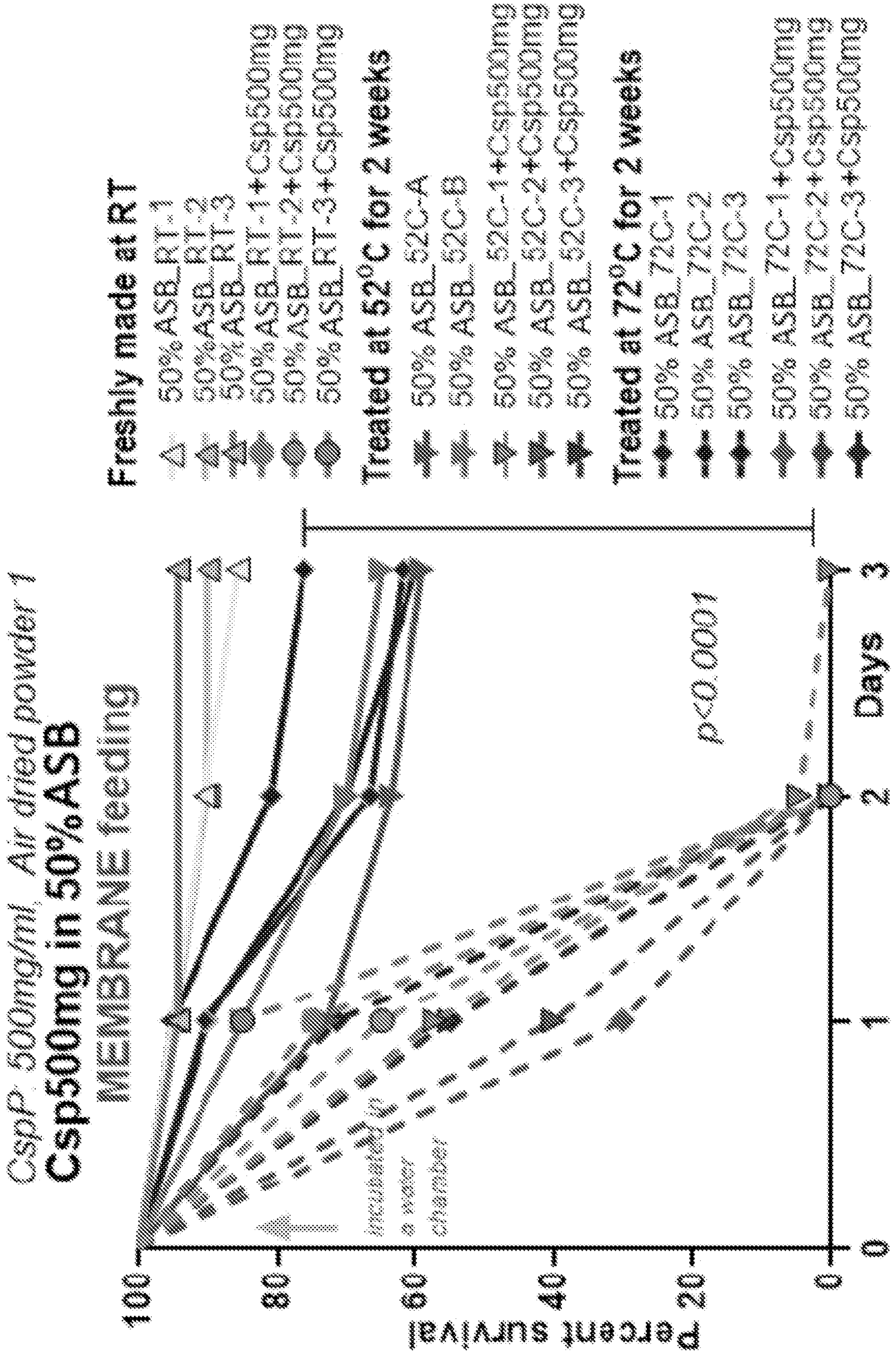
FIG. 22A-22B.
Figure 22B:
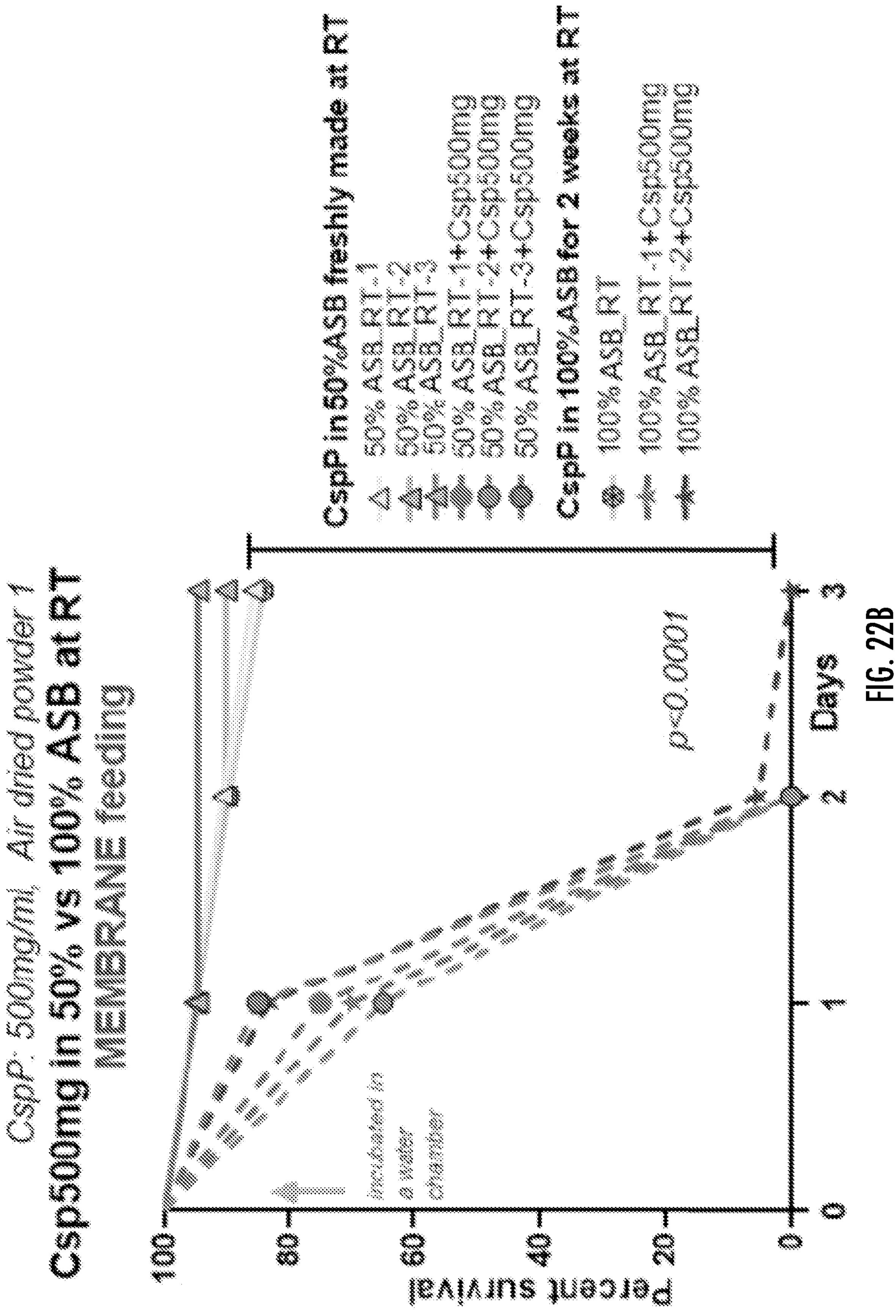

Example 10: Shelf-live and stability of Csp_P airdried powder in ASB. To investigate the stability (shelf life) of the AI in the Csp_P airdried powder when present in the 50% ASB we incubate 500 mg/ml Csp_P airdried powder—ASB solution at 52° C. and 70° C. for two weeks prior to performing mortality assays, using a freshly made Csp_P airdried powder—ASB solution as control. These assays showed no loss of activity of Csp_P airdried powder in 50% ASB after a 14 days incubation at either 52° C. and 70° C. (FIG. 22 A). In a second assay we tested the mosquito killing activity of a 500 mg/ml Csp_P airdried powder—100% ASB solution that had been incubated at RT for two weeks, and observer no difference in activity compared to a freshly made Csp_P-ASB solution (FIG. 22B). Previous accelerated shelf-life assays, with the Csp_P powder alone, has shown exceptional stability, at both 52° C. and 70° C. temperature conditions (Caragata et al., 2000).

Example 11: Quantification of the airdried powder AL, using weight, protein and lipid content as metrics. In order to more precisely quantify the optimal dosage of Csp_P required for the adulticidal activity, we have quantified the Csp_P with several different measures. We have measured the OD600 from different batches of the Csp_P large scale cultures and enumerate the live cells right after the 3-d shaking culture by correlating 1 OD600 with a range of 1.5~5×$10^8$ cells/ml. And we have used the micro BCA kit (ThermoFisher Scientific) to measure the total protein from 10 mg of Csp_P dried powder from different batches of the cultures. Similarly, we are currently measuring the total lipids from 10 mg of the powder (FIG. 23).

That which is claimed:

1. A method for producing a non-live Chromobacterium biopesticide comprising the steps of:

(a) growing the Chromobacterium in a bioreactor with culture medium;

(b) oxygenating the Chromobacterium during step (a);

(c) adding an antibiotic to the Chromobacterium culture;

(d) incubating the Chromobacterium culture under hypoxic conditions;

(e) pouring the Chromobacterium culture on to a substrate;

(f) air drying the Chromobacterium; and (g) crushing the dried Chromobacterium into a powder.

2. The method of claim 1, wherein oxygenating step (b) is accomplished by shaking the Chromobacterium in the bioreactor.

3. The method of claim 1, wherein the antibiotic is hygromycin B.

4. The method of claim 1, wherein step (d) is performed at room temperature.

5. The method of claim 1, wherein step (e) is performed at room temperature.

6. The method of claim 1, wherein the Chromobacterium is *Chromobacterium* sp. Panama.

7. A method for producing a non-live Chromobacterium biopesticide comprising the steps of:

(a) growing the Chromobacterium in a bioreactor with culture medium;

(b) oxygenating the Chromobacterium during step (a);

(c) adding an antibiotic to the Chromobacterium culture;

(d) incubating the Chromobacterium culture under hypoxic conditions;

(e) performing an organic extraction of the Chromobacterium; and (f) collecting the organic phase comprising the Chromobacterium.

8. The method of claim 7, further comprising the step of evaporating the organic phase of step (f).

9. The method of claim 8, further comprising the step of sonicating the dried Chromobacterium.

10. The method of claim 7, wherein oxygenating step (b) is accomplished by shaking the Chromobacterium in the bioreactor.

11. The method of claim 7, wherein the antibiotic is hygromycin B.

12. The method of claim 7, wherein step (d) is performed at room temperature.

13. The method of claim 7, wherein the Chromobacterium is *Chromobacterium* sp. Panama.

* * * * *